(12) United States Patent
Lizée et al.

(10) Patent No.: US 12,178,787 B2
(45) Date of Patent: Dec. 31, 2024

(54) T CELL RECEPTORS FOR IMMUNOTHERAPY

(71) Applicant: Board of Regents, The University of Texas System, Austin, TX (US)

(72) Inventors: Gregory Lizée, Houston, TX (US); Cassian Yee, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1154 days.

(21) Appl. No.: 16/652,932

(22) PCT Filed: Oct. 12, 2018

(86) PCT No.: PCT/US2018/055691
§ 371 (c)(1),
(2) Date: Apr. 1, 2020

(87) PCT Pub. No.: WO2019/075385
PCT Pub. Date: Apr. 18, 2019

(65) Prior Publication Data
US 2020/0237820 A1 Jul. 30, 2020

Related U.S. Application Data

(60) Provisional application No. 62/571,447, filed on Oct. 12, 2017.

(51) Int. Cl.
| | | |
|---|---|---|
| *A61K 39/00* | (2006.01) | |
| *A61K 31/675* | (2006.01) | |
| *A61K 31/7076* | (2006.01) | |
| *C07K 14/725* | (2006.01) | |
| *C12N 5/0783* | (2010.01) | |
| *C12N 15/86* | (2006.01) | |
| *C07K 14/74* | (2006.01) | |

(52) U.S. Cl.
CPC ........ *A61K 31/675* (2013.01); *A61K 31/7076* (2013.01); *A61K 39/4611* (2023.05); *A61K 39/4615* (2023.05); *A61K 39/4622* (2023.05); *A61K 39/4632* (2023.05); *A61K 39/46449* (2023.05); *C07K 14/7051* (2013.01); *C12N 5/0636* (2013.01); *C12N 5/0637* (2013.01); *C12N 15/86* (2013.01); *A61K 2239/57* (2023.05); *C07K 14/70539* (2013.01)

(58) Field of Classification Search
None
See application file for complete search history.

(56) References Cited

U.S. PATENT DOCUMENTS

| | | |
|---|---|---|
| 2013/0078226 A1 | 3/2013 | Nakauchi et al. |
| 2015/0337369 A1 | 11/2015 | Davis et al. |

FOREIGN PATENT DOCUMENTS

| | | |
|---|---|---|
| CN | 1745099 A | 3/2006 |
| WO | 2017/059084 A1 | 4/2017 |
| WO | 2017/096304 A1 | 6/2017 |
| WO | WO 2017/089768 | 6/2017 |
| WO | 2017/158103 A1 | 9/2017 |

OTHER PUBLICATIONS

Malia et al, Proteins, 2016, 84:427-434. (Year: 2016).*
Barthelemy et al, Journal of Biological Chemistry, 2008, 283:3639-3654. (Year: 2008).*
Beiboer et al, Journal of Molecular Biology, 2000, 296:833-849. (Year: 2000).*
Choi et al, 2011, Molecular Biosystems, 2011, 7:3327-3334. (Year: 2011).*
De Genst et al, Developmental and Comparative Immunology, 2006, 30:187-98. (Year: 2006).*
Griffiths et al, The EMBO Journal, 1993, 12:725-734. (Year: 1993).*
Klimka et al, British Journal of Cancer, 2000, 83:252-260. (Year: 2000).*
Ward et al, Nature, 1989, 341:544-546. (Year: 1989).*
Rosati et al, BMC Biotechnology (2017) 17:61, Overview of methodologies for T-cell receptor repertoire analysis. (Year: 2017).*
Office Action issued in Corresponding Japanese Application No. 2020-520494, dated Aug. 18, 2022 (English Translation provided).
Office Action issued in Corresponding Chinese Application No. 201880075955.X, dated Jan. 12, 2023 (English Translation).
Park et al., "SLC45A2: A Melanoma Antigen with High Tumor Selectivity and Reduced Potential for Autoimmune Toxicity" Cancer Immunology Research, vol. 5, No. 8, Aug. 1, 2017 (Aug. 1, 2017), pp. 618-629.
Dunn et al., "Directed evolution of human T cell receptor CDR2 residues by phage display dramatically enhances affinity for cognate peptide-MHC without increasing apparent cross-reactivity", Protein Science, vol. 15, No. 4, Apr. 1, 2006 (Apr. 1, 2006), pp. 710-721, Wiley, US.
Blevins, S. J., et al. "How structural adaptability exists alongside HLA-A2 bias in the human αβ TCR repertoire." *Proceedings of the National Academy of Sciences*. 2016, vol. 113, No. 9, pp. E1276-E1285.
Cole, D. K., et al. "T-cell receptor (TCR)-peptide specificity overrides affinity-enhancing TCR-major histocompatibility complex interactions." *Journal of Biological Chemistry*. vol. 289, No. 2, pp. 628-638; 2014.
Janeway CA Jr, et al. "T-cell receptor gene rearrangement." *Immunobiology: The Immune System in Health and Disease*; https://www.ncbi.nim.nih.gov/books/NBK27145/. 2001.
Office Action dated Jan. 18, 2024 issued in Australian Patent Application No. 2018346957.

(Continued)

*Primary Examiner* — Meera Natarajan
*Assistant Examiner* — Cheom-Gil Cheong
(74) *Attorney, Agent, or Firm* — Norton Rose Fulbright US LLP

(57) ABSTRACT

Provided are T cell receptors (TCR) and TCR variable regions that can selectively bind SLC45A2. The TCR may be utilized in various therapies, such as autologous cell transplantation, to treat a cancer, such as a cutaneous melanoma, uveal melanoma, a mucosal melanoma, or a metastatic melanoma. Methods for expanding a population of T cells that target SLC45A2 are also provided.

20 Claims, 30 Drawing Sheets

Specification includes a Sequence Listing.

(56) References Cited

OTHER PUBLICATIONS

Wang, B., et al. "Peptidic termini play a significant role in TCR recognition." *The Journal of Immunology.* vol. 169, No. 6, pp. 3137-3145; 2002.
Chen, et al., "TCRdb: a comprehensive database for T-cell receptor sequences with powerful search function", *Nucleic Acids Res*, vol. 49, pp. D468-D474, 2021.
Office Action dated Jun. 13, 2024 issued in Australian Patent Application No. 2018346957.

* cited by examiner

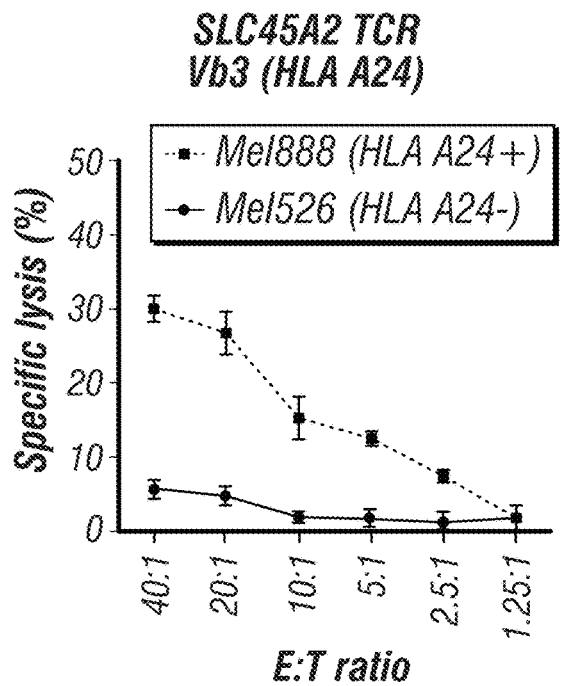
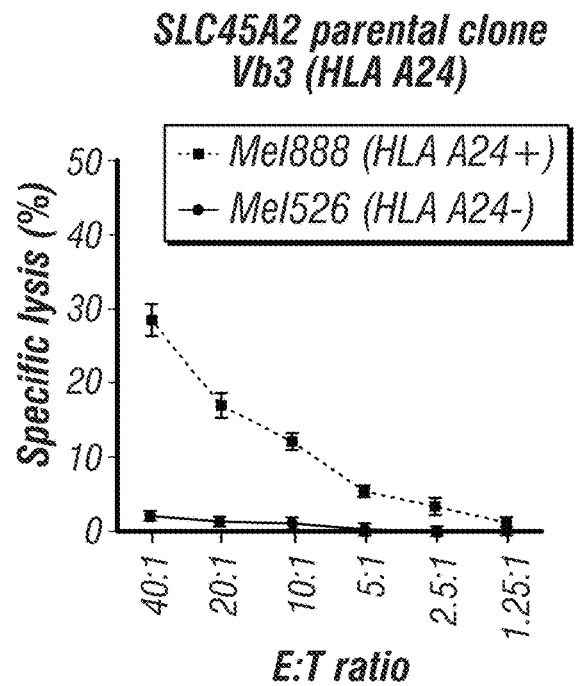
FIG. 2A
FIG. 2B
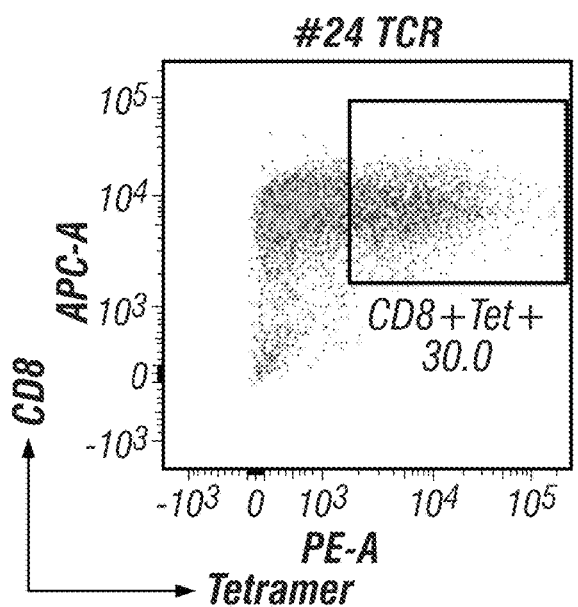
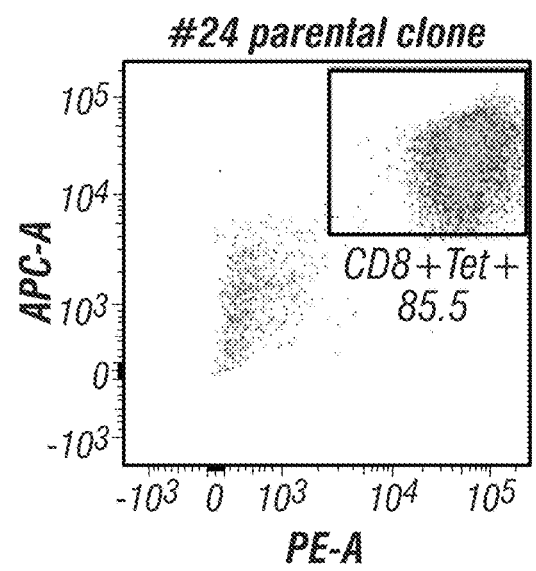
FIG. 3A
FIG. 3B

TCR Clone #24 alpha chain (SEQ ID NO:1)

```
ATGGAGAAGA ATCCTTTGGC AGCCCCATTA CTAATCCTCT GGTTTCATCT
TGACTGCGTG AGCAGCATAC TGAACGTGGA ACAAAGTCCT CAGTCACTGC
ATGTTCAGGA GGGAGACAGC ACCAATTTCA CCTGCAGCTT CCCTTCCAGC
AATTTTTATG CCTTACACTG GTACAGATGG GAAACTGCAA AAAGCCCCGA
GGCCTTGTTT GTAATGACTT TAAATGGGGA TGAAAGAAG AAAGGACGAA
TAAGTGCCAC TCTTAATACC AAGGAGGGTT ACAGCTATTT GTACATCAAA
GGATCCCAGC CTGAAGACTC AGCCACATAC CTCTGTGCCT TTTTGTCGAA
TAACAATGCC AGACTCATGT TTGGAGATGG AACTCAGCTG GTGGTGAAGC
CCAATATCCA GAACCCTGAC CCTGCCGTGT ACCAGCTGAG AGACTCTAAA
TCCAGTGACA AGTCTGTCTG CCTATTCACC GATTTTGATT CTCAAACAAA
TGTGTCACAA GTAAGGATT CTGATGTGTA TATCACAGAC AAAACTGTGC
TAGACATGAG GTCTATGGAC TTCAAGAGCA ACAGTGCTGT GGCCTGGAGC
AACAAATCTG ACTTTGCATG TGCAAACGCC TTCAACAACA GCATTATTCC
AGAAGACACC TTCTTCCCCA GCCCAGAAAG TTCCTGTGAT GTCAAGCTGG
TCGAGAAAAG CTTTGAAACA GATACGAACC TAAACTTTCA AAACCTGTCA
GTGATTGGGT TCCGAATCCT CCTCCTGAAA GTGGCCGGGT TTAATCTGCT
CATGACGCTG CGGCTGTGGT CCAGCTAA
```

TCR Clone #24 alpha chain (SEQ ID NO:2)

```
MEKNPLAAPL LILWFHLDCV SSILNVEQSP QSLHVQEGDS TNFTCSFPSS
NFYALHWYRW ETAKSPEALF VMTLNGDEKK KGRISATLNT KEGYSYLYIK
GSQPEDSATY LCAFLSNNNA RLMFGDGTQL VVKPNIQNPD PAVYQLRDSK
SSDKSVCLFT DFDSQTNVSQ SKDSDVYITD KTVLDMRSMD FKSNSAVAWS
NKSDFACANA FNNSIIPEDT FFPSPESSCD VKLVEKSFET DTNLNFQNLS
VIGFRILLLK VAGFNLLMTL RLWSS
```

FIG. 13A

TCR Clone #24 beta chain (SEQ ID NO:6)

```
ATGCTTAGTC CTGACCTGCC TGACTCTGCC TGGAACACCA GGCTCCTCTG
CCATGTCATG CTTTGTCTCC TGGGAGCAGG TTCAGTGGCT GCTGGACTCA
TCCAGTCCCC AAGACATCTG ATCAAAGAAA AGAGGGAAAC AGCCACTCTG
AAATGCTATC CTATCCCTAG ACACGACACT GTCTACTGGT ACCAGCAGGG
TCCAGGTCAG GACCCCAGT TCCTCATTTC GTTTATGAA AAGATGCAGA
GCGATAAAGG AAGCATCCCT GATCGATTCT CAGCTCAACA GTTCAGTGAC
TATCATTCTG AACTGAACAT GAGCTCCTTG GAGCTGGGGG ACTCAGCCCT
GTACTTCTGT GCCAGCAGCT TATGGGGCAG CCATAATTCA CCCCTCCACT
TTGGGAACGG GACCAGGCTC ACTGTGACAG AGGACCTGAA CAAGGTGTTC
CCACCCGAGG TCGCTGTGTT TGAGCCATCA GAAGCAGAGA TCTCCCACAC
CCAAAAGGCC ACACTGGTGT GCCTGGCCAC AGGCTTCTTC CCCGACCACG
TGGAGCTGAG CTGGTGGGTG AATGGGAAGG AGGTGCACAG TGGGGTCAGC
ACGGACCCGC AGCCCCTCAA GGAGCAGCCC GCCCTCAATG ACTCCAGATA
CTGCCTGAGC AGCCGCCTGA GGGTCTCGGC CACCTTCTGG CAGAACCCCC
GCAACCACTT CCGCTGTCAA GTCCAGTTCT ACGGGCTCTC GGAGAATGAC
GAGTGGACCC AGGATAGGGC CAAACCCGTC ACCCAGATCG TCAGCGCCGA
GGCCTGGGGT AGAGCAGACT GTGGCTTTAC CTCGGTGTCC TACCAGCAAG
GGGTCCTGTC TGCCACCATC CTCTATGAGA TCCTGCTAGG GAAGGCCACC
CTGTATGCTG TGCTGGTCAG CGCCCTTGTG TTGATGGCCA TGGTCAAGAG
AAAGGATTTC TAA
```

TCR Clone #24 beta chain (SEQ ID NO:7)

```
MLSPDLPDSA WNTRLLCHVM LCLLGAGSVA AGVIQSPRHL IKEKRETATL
KCYPIPRHDT VYWYQQGPGQ DPQFLISFYE KMQSDKGSIP DRFSAQQFSD
YHSELNMSSL ELGDSALYFC ASSLWGSHNS PLHFGNGTRL TVTEDLNKVF
PPEVAVFEPS EAEISHTQKA TLVCLATGFF PDHVELSWWV NGKEVHSGVS
TDPQPLKEQP ALNDSRYCLS SRLRVSATFW QNPRNHFRCQ VQFYGLSEND
EWTQDRAKPV TQTVSAEAWG RADCGFTSVS YQQGVLSATI LYEILLGKAT
LYAVLVSALV LMAMVKRKDF
```

FIG. 13B

TCR Clone #39 Alpha chain (SEQ ID NO:11)

```
ATGGAAACTC TCCTGGGAGT GTCTTTGGTG ATTCTATGGC TTCAACTGGC
TAGGGTGAAC AGTCAACAGG GAGAAGAGGA TCCTCAGGCC TTGAGCATCC
AGGAGGGTGA AAATGCCACC ATGAACTGCA GTTACAAAAC TAGTATAAAC
AATTTACAGT GGTATAGACA AAATTCAGGT AGAGGCCTTG TCCACCTAAT
TTTAATACGT TCAAATGAAA GAGAGAAACA CAGTGGAAGA TTAAGAGTCA
GCCTTGACAC TTCCAAGAAA AGCAGTTCCT TGTTGATCAC GGCTTCCCGG
GCAGCAGACA CTGCTTCTTA CTTCTGTGCT ACGGACGATA ATGCAGGCAA
CATGCTCACC TTTGGAGGGG GAACAAGGTT AATGGTCAAA CCCCATATCC
AGAACCCTGA CCCTGCCGTG TACCAGCTGA GAGACTCTAA ATCCAGTGAC
AAGTCTGTCT GCCTATTCAC CGATTTTGAT TCTCAAACAA ATGTGTCACA
AAGTAAGGAT TCTGATGTGT ATATCACAGA CAAAACTGTG CTAGACATGA
GGTCTATGGA CTTCAAGAGC AACAGTGCTG TGGCCTGGAG CAACAAATCT
GACTTTGCAT GTGCAAACGC CTTCAACAAC AGCATTATTC CAGAAGACAC
CTTCTTCCCC AGCCCAGAAA GTTCCTGTGA TGTCAAGCTG GTCGAGAAAA
GCTTTGAAAC AGATACGAAC CTAAACTTTC AAAACCTGTC AGTGATTGGG
TTCCGAATCC TCCTCCTGAA AGTGGCCGGG TTTAATCTGC TCATGACGCT
GCGGCTGTGG TCCAGCTAA
```

TCR Clone #39 Alpha chain (SEQ ID NO:12)

```
METLLGVSLV ILWLQLARVN SQQGEEDPQA LSIQEGENAT MNCSYKTSIN
NLQWYRQNSG RGLVHLILIR SNEREKHSGR LRVTLDTSKK SSSLLITASR
AADTASYFCA TDDNAGNMLT FGGGTRLMVK PHIQNPDPAV YQLRDSKSSD
KSVCLFTDFD SQTNVSQSKD SDVYITDKTV LDMRSMDFKS NSAVAWSNKS
DFACANAFNN SIIPEDTFFP SPESSCDVKL VEKSFETDTN LNFQNLSVIG
FRILLLKVAG FNLLMTLRLW SS
```

FIG. 13C

TCR Clone #39 Beta chain (SEQ ID NO:16)

```
ATGGGAATCA GGCTCCTCTG TCGTGTGGCC TTTTGTTTCC TGGCTGTAGG
CCTCGTAGAT GTGAAAGTAA CCCAGAGCTC GAGATATCTA GTCAAAAGGA
CGGGAGAGAA AGTTTTTCTG GAATGTGTCC AGGATATGGA CCATGAAAAT
ATGTTCTGGT ATCGACAAGA CCCAGGTCTG GGCTACGGC TGATCTATTT
CTCATATGAT GTTAAAATGA AGAAAAAGG AGATATTCCT GAGGGGTACA
GTGTCTCTAG AGAAGAAG GAGCGCTTCT CCCTGATTCT GGAGTCCGCC
AGCACCAACC AGACATCTAT GTACCTCTGT GCCAGCAGTT TTACCCCAGA
TACGCAGTAT TTTGGCCCAG GCACCCGGCT GACAGTGCTC GAGGACCTGA
AAAACGTGTT CCCACCCGAG GTCGCTGTGT TGAGCCATC AGAAGCAGAG
ATCTCCACA CCCAAAAGGC CACACTGGTG TGCCTGGCCA CAGGCTTCTA
CCCCGACCAC GTGGAGCTGA GCTGGTGGGT GAATGGGAAG GAGGTGCACA
GTGGGGTCAG CACAGACCCG CAGCCCCTCA AGGAGCAGCC GGCCCTCAAT
GACTCCAGAT ACTGCCTGAG CAGCCGCCTG AGGGTCTCGG CCACCTTCTG
GCAGAACCCC CGCAACCACT TCCGCTGTCA AGTCCAGTTC TACGGGCTCT
CGGAGAATGA CGAGTGGACC CAGGATAGGG CCAAACCTGT CACCCAGATC
GTCAGCGCCG AGGCCTGGGG TAGAGCAGAC TGTGGCTTCA CCTCCCAGTC
TTACCAGCAA GGGGTCCTGT CTGCCACCAT CCTCTATGAG ATCTTGCTAG
GGAAGGCCAC CTTGTATGCC GTGCTGGTCA GTGCCCTCGT GCTGATGGCC
ATGGTCAAGA GAAAGGATTT CTAA
```

TCR Clone #39 Beta chain (SEQ ID NO:17)

```
MGIRLLCRVA FCFLAVGLVD VKVTQSSRYL VKRTGEKVFL ECVQDMDHEN
MFWYRQDPGL GLRLIYFSYD VKMKEKGDIP EGYSVSREKK ERFSLILESA
STNQTSMYLC ASSFTPDTQY FGPGTRLTVL EDLKNVFPPE VAVFEPSEAE
ISHTQKATLV CLATGFYPDH VELSWWVNGK EVHSGVSTDP QPLKEQPALN
DSRYCLSSRL RVSATFWQNP RNHFRCQVQF YGLSENDEWT QDRAKPVTQI
VSAEAWGRAD CGFTSESYQQ GVLSATILYE ILLGKATLYA VLVSALVLMA
MVKRKDF
```

FIG. 13D

TCR Clone #76 alpha chain (SEQ ID NO:21)

```
ATGGAGACCC TCTTGGGCCT GCTTATCCTT TGGCTGCAGC TGCAATGGGT
GAGCAGCAAA CAGGAGGTGA CGCAGATTCC TGCAGCTCTG AGTGTCCCAG
AAGGAGAAAA CTTGGTTCTC AACTGCAGTT TCACTGATAG CGCTATTTAC
AACCTCCAGT GGTTTAGGCA GGACCCTGGG AAAGGTCTCA CATCTCTGTT
GCTTATTCAG TCAAGTCAGA GAGAGCAAAC AAGTGGAAGA CTTAATGCCT
CGCTGGATAA ATCATCAGGA CGTAGTACTT TATACATTGC AGCTTCTCAG
CCTGGTGACT CAGCCACCTA CCTCTGTGCT GATAATCAAA CTGGGGCAAA
CAACCTCTTC TTTGGGACTG GAACGAGACT CACCGTTATT CCCTATATCC
AGAACCCTGA CCCTGCCGTG TACCAGCTGA GAGACTCTAA ATCCAGTGAC
AAGTCTGTCT GCCTATTCAC CGATTTTGAT TCTCAAACAA ATGTGTCACA
AAGTAAGGAT TCTGATGTGT ATATCACAGA CAAAACTGTG CTAGACATGA
GGTCTATGGA CTTCAAGAGC AACAGTGCTG TGGCCTGGAG CAACAAATCT
GACTTTGCAT GTGCAAACGC CTTCAACAAC AGCATTATTC CAGAAGACAC
CTTCTTCCCC AGCCCAGAAA GTTCCTGTGA TGTCAAGCTG GTCGAGAAAA
GCTTTGAAAC AGATACGAAC CTAAACTTTC AAAACCTGTC AGTGATTGGG
TTCCGAATCC TCCTCCTGAA AGTGGCCGGG TTTAATCTGC TCATGACGCT
GCGGCTGTGG TCCAGC
```

TCR Clone #76 alpha chain (SEQ ID NO:22)

```
METLLGLLIL WLQLQWVSSK QEVTQIPAAL SVPEGENLVL NCSFTDSAIY
NLQWFRQDPG KGLTSLLLIQ SSQREQTSGR LNASLDKSSG RSTLYTAASQ
PGDSATYLCA DNQTGANNLF FGTGTRLTVI PYIQNPDPAV YQLRDSKSSD
KSVCLFTDFD SQTNVSQSKD SDVYITDKTV LDMRSMDFKS NSAVAWSNKS
DFACANAFNN SIIPEDTFFP SPESSCDVKL VEKSFETDTN LNFQNLSVIG
FRILLLKVAG FNLLMTLRLW SS
```

FIG. 13E

TCR Clone #76 beta chain (SEQ ID NO:26)

```
ATGCTTAGTC CTGACCTGCC TGACTCTGCC TGGAACACCA GGCTCCTCTG
CCATGTCATG CTTTGTCTCC TGGGAGCAGG TTCAGTGGCT GCTGGAGTCA
TCCAGTCCCC AAGACATCTG ATCAAGAAA AGAGGGAAAC AGCCACTCTG
AAATGCTATC CTATCCCTAG ACACGACACT GTCTACTGGT ACCAGCAGGG
TCCAGGTCAG GACCCCAGT TCCTCATTTC GTTTATGAA AAGATGCAGA
GCGATAAAGG AAGCATCCCT GATCGATTCT CAGCTCAACA GTTCAGTGAC
TATCATTCTG AACTGAACAT GAGCTCCTTG GAGCTGGGGG ACTCAGCCCT
GTACTTCTGT GCCAGCAGCG AGGGGGGGTA TGGAAACTAT GGCTACACCT
TCGGTTCGGG GACCAGGTTA ACCGTTGTAG AGGACCTGAA CAAGGTGTTC
CCACCCGAGG TCGCTGTGTT TGAGCCATCA GAAGCAGAGA TCTCCCACAC
CCAAAAGGCC ACACTGGTGT GCCTGGCCAC AGGCTTCTTC CCCGACCACG
TGGAGCTGAG CTGGTGGGTG AATGGGAAGG AGGTGCACAG TGGGGTCAGC
ACGGACCCGC AGCCCCTCAA GGAGCAGCCC GCCCTCAATG ACTCCAGATA
CTGCCTGAGC AGCCGCCTGA GGGTCTCGGC CACCTTCTGG CAGAACCCCC
GCAACCACTT CCGCTGTCAA GTCCAGTTCT ACGGGCTCTC GGAGAATGAC
GAGTGGACCC AGGATAGGGC CAAACCCGTC ACCCAGATCG TCAGCGCCGA
GGCCTGGGGT AGAGCAGACT GTGGCTTTAC CTCGGTGTCC TACCAGCAAG
GGGTCCTGTC TGCCACCATC CTCTATGAGA TCCTGCTAGG GAAGGCCACC
CTGTATGCTG TGCTGGTCAG CGCCCTTGTG TTGATGGCCA TGGTCAAGAG
AAAGGATTTC TAA
```

TCR Clone #76 beta chain (SEQ ID NO:27)

```
MLSPDLPDSA WNTRLLCHVM LCLLGAGSVA AGVIQSPRHL IKEKRETATL
KCYPIPRHDT VYWYQQGPGQ DPQFLISFYE KMQSDKGSIP DRFSAQQFSD
YHSELNMSSL ELGDSALYFC ASSEGGYGNY GYTFGSGTRL TVVEDLNKVF
PPEVAVFEPS EAEISHTQKA TLVCLATGFF PDHVELSWWV NGKEVHSGVS
TDPQPLKEQP ALNDSRYCLS SRLRVSATFW QNPRNHFRCQ VQFYGLSEND
EWTQDRAKPV TQIVSAEAWG RADCGFTSVS YQQGVLSATI LYEILLGKAT
LYAVLVSALV LMAMVKRKDF
```

FIG. 13F

TCR Clone Vβ3 Alpha chain (SEQ ID NO:31)

```
ATGTCACTTT CTAGCCTGCT GAAGGTGGTC ACAGCTTCAC TGTGGCTAGG
ACCTGGCATT GCCCAGAAGA TAACTCAAAC CCAACCAGGA ATGTTCGTGC
AGGAAAAGGA GGCTGTGACT CTGGACTGCA CATATGACAC CAGTGATCCA
AGTTATGGTC TATTCTGGTA CAAGCAGCCC AGCAGTGGGG AAATGATTTT
TCTTATTTAT CAGGGGTCTT ATGACCAGCA AAATGCAACA GAAGGTCGCT
ACTCATTGAA TTTCCAGAAG GCAAGAAAAT CCGCCAACCT TGTCATCTCC
GCTTCACAAC TGGGGGACTC AGCAATGTAC TTCTGTGCAA TGAGAGAGGG
CTGGGGCTTT GGAAATGAGA AATTAACCTT TGGGACTGGA ACAAGACTCA
CCATCATACC CAATATCCAC AACCCTGACC CTGCCGTGTA CCAGCTGAGA
GACTCTAAAT CCAGTGACAA GTCTGTCTGC CTATTCACCG ATTTTGATTC
TCAAACAAAT GTGTCACAAA GTAAGGATTC TGATGTGTAT ATCACAGACA
AAACTGTGCT AGACATGAGG TCTATGGACT TCAAGAGCAA CAGTGCTGTG
GCCTGGAGCA ACAAATCTGA CTTTGCATGT GCAAACGCCT TCAACAACAG
CATTATTCCA GAAGACACCT TCTTCCCCAG CCCAGAAAGT TCCTGTGATG
TCAAGCTGGT CGAGAAAAGC TTTGAAACAG ATACGAACCT AAACTTTCAA
AACCTGTCAG TGATTGGGTT CCGAATCCTC CTCCTGAAAG TGGCCGGGTT
TAATCTGCTC ATGACGCTGC GGCTGTGGTC CAGCTAA
```

TCR Clone Vβ3 Alpha chain (SEQ ID NO:32)

```
MSLSSLLKVV TASLWLGPGI AQKITQTQPG MFVQEKEAVT LDCTYDTSDP
SYGLFWYKQP SSGEMIFLIY QGSYDQQNAT EGRYSLNFQK ARKSANLVIS
ASQLGDSAMY FCAMREGWGF GNEKLTFGTG TRLTIIPNIQ NPDPAVYQLR
DSKSSDKSVC LFTDFDSQTN VSQSKDSDVY ITDKTVLDMR SMDFKSNSAV
AWSNKSDFAC ANAFNNSIIP EDTFFPSPES SCDVKLVEKS FETDTNLNFQ
NLSVIGFRIL LLKVAGFNLL MTLRLWSS
```

FIG. 13G

TCR Clone Vβ3 Beta chain (SEQ ID NO:36)

```
ATGGGAATCA GGCTCCTCTG TCGTGTGGCC TTTTGTTTCC TGGCTGTAGG
CCTCGTAGAT GTGAAAGTAA CCCAGAGCTC GAGATATCTA GTCAAAGGA
CGGGAGAGAA AGTTTTTCTG GAATGTGTCC AGGATATGGA CCATGAAAAT
ATGTTCTGGT ATCGACAAGA CCCAGGTCTG GGCTACGGC TGATCTATTT
CTCATATGAT GTTAAAATGA AGAAAAAGG AGATATTCCT GAGGGGTACA
GTGTCTCTAG AGAAGAAG GAGCGCTTCT CCCTGATTCT GGAGTCCGCC
AGCACCAACC AGACATCTAT GTACCTCTGT GCCAGCAGAG AGAAGCGGGG
GGAAGACACA GATACGCAGT ATTTTGGCCC AGGCACCCGG CTGACAGTGC
TCGAGGACCT GAAAACGTG TTCCCACCCG AGGTCGCTGT GTTTGAGCCA
TCAGAAGCAG AGATCTCCCA CACCCAAAAG GCCACACTGG TGTGCCTGGC
CACAGGCTTC TACCCCGACC ACGTGGAGCT GAGCTGGTGG GTGAATGGGA
AGGAGGTGCA CAGTGGGGTC AGCACAGACC CGCAGCCCCT CAAGGAGCAG
CCCGCCCTCA ATGACTCCAG ATACTGCCTG AGCAGCCGCC TGAGGGTCTC
GGCCACCTTC TGGCAGAACC CCCGCAACCA CTTCCGCTGT CAAGTCCAGT
TCTACGGGCT CTCGGAGAAT GACGAGTGGA CCCAGGATAG GGCCAAACCT
GTCACCCAGA TCGTCAGCGC CGAGGCCTGG GGTAGAGCAG ACTGTGGCTT
CACCTCCGAG TCTTACCAGC AAGGGGTCCT GTCTGCCACC ATCCTCTATG
AGATCTTGCT AGGGAAGGCC ACCTTGTATG CCGTGCTGGT CAGTGCCCTC
GTGCTGATGG CCATGGTCAA GAGAAAGGAT TCCTAA
```

TCR Clone Vβ3 Beta chain (SEQ ID NO:37)

```
MGIRLLCRVA FCFLAVGLVD VKVTQSSRYL VKRTGEKVFL ECVQDMDHEN
MFWYRQDPGL GLRLIYFSYD VKMKEKGDIP EGYSVSREKK ERFSLILESA
STNQTSMYLC ASREKRGEDT DTQYFGPGTR LTVLEDLKNV FPPEVAVFEP
SEAEISHTQK ATLVCLATGF YPDHVELSWW VNGKEVHSGV STDPQPLKEQ
PALNDSRYCL SSRLRVSATF WQNPRNHFRC QVQFYGLSEN DEWTQDRAKP
VTQIVSAEAW GRADCGFTSE SYQQGVLSAT ILYEILLGKA TLYAVLVSAL
VLMAMVKRKD S
```

FIG. 13H

TCR Clone Vβ22 alpha chain (SEQ ID NO:41)

```
ATGGAGAAGA ATCCTTTGGC AGCCCCATTA CTAATCCTCT GGTTTCATCT
TGACTGCCTG AGCAGCATAC TGAACGTGGA ACAAAGTCCT CAGTCACTGC
ATGTTCAGGA GGGAGACAGC ACCAATTTCA CCTGCAGCTT CCCTTCCAGC
AATTTTTATG CCTTACACTG GTACAGATGG GAAACTGCAA AAAGCCCCGA
GGCCTTGTTT GTAATGACTT TAAATGGGGA TGAAAAGAAG AAAGGACGAA
TAAGTGCCAC TCTTAATACC AAGGAGGGTT ACAGCTATTT GTACATCAAA
CGATCCCAGC CTGAAGACTC AGCCACATAC CTCTGTGCCT TCGACTCGTA
CTATAATGCA GGCAACATGC TCACCTTTGG AGGGGGAACA AGGTTAATGG
TCAAACCCCA TATCCAGAAC CCTGACCCTG CCGTGTACCA GCTGAGAGAC
TCTAAATCCA GTGACAAGTC TGTCTGCCTA TTCACCGATT TTGATTCTCA
AACAAATGTG TCACAAGTA AGGATTCTGA TGTGTATATC ACAGACAAAA
CTGTGCTAGA CATGAGGTCT ATGGACTTCA AGAGCAACAG TGCTGTGGCC
TGGAGCAACA AATCTGACTT TGCATGTGCA AACGCCTTCA ACAACAGCAT
TATTCCAGAA GACACCTTCT TCCCCAGCCC AGAAAGTTCC TGTGATGTCA
AGCTGGTCGA GAAAAGCTTT GAAACAGATA CGAACCTAAA CTTTCAAAAC
CTGTCAGTGA TTGGGTTCCG AATCCTCCTG CTGAAAGTGG CCGGGTTTAA
TCTGCTCATG ACGCTGCGGC TGTGGTCCAG CTAA
```

TCR Clone Vβ22 alpha chain (SEQ ID NO:42)

```
MEKNPLAAPL LILWFHLDCV SSILNVEQSP QSLHVQEGDS TNFTCSFPSS
NFYALHWYRW ETAKSPEALF VMTLNGDEKK KGRISATLNT KEGYSYLYIK
GSQPEDSATY LCAFDSYYNA GNMLTFGGGT RLMVKPHIQN PDPAVYQLRD
SKSSDKSVCL FTDFDSQTNV SQSKDSDVYI TDKTVLDMRS MDFKSNSAVA
WSNKSDFACA NAFNNSIIPE DTFEPSPESS CDVKLVEKSF ETDTNLNFQN
LSVIGFRILL LKVAGFNLLM TLRLWSS
```

FIG. 13I

TCR Clone Vβ22 beta chain (SEQ ID NO:46)

```
ATGGATACCT GGCTCGTATG CTGGGCAATT TTTAGTCTCT TGAAAGCAGG
ACTCACAGAA CCTGAAGTCA CCCAGACTCC CAGCCATCAG GTCACACAGA
TGGGACAGGA AGTGATCTTG CGCTGTGTCC CCATCTCTAA TCACTTATAC
TTCTATTGGT ACAGACAAAT CTTGGGGCAG AAAGTCGAGT TTCTGGTTTC
CTTTTATAAT AATGAAATCT CAGAGAAGTC TGAAATATTC GATGATCAAT
TCTCAGTTGA AAGGCCTGAT GGATCAAATT TCACTCTGAA GATCCGGTCC
ACAAAGCTGG AGGACTCAGC CATGTACTTC TGTGCCAGCA GCGCAGACAC
CGGGACACTG AACACTGAAG CTTTCTTTGG ACAAGGCACC AGACTCACAG
TTGTAGAGGA CCTGAACAAG GTGTTCCCAC CCGAGGTCGC TGTGTTTGAG
CCATCAGAAG CAGAGATCTC CCACACCCAA AAGGCCACAC TGGTGTGCCT
GGCCACAGGC TTCTTCCCCG ACCACGTGGA GCTGAGCTGG TGGGTGAATG
GGAAGGAGGT GCACAGTGGG GTCAGCACGG ACCCGCAGCC CCTCAAGGAG
CAGCCCGCCC TCAATGACTC CAGATACTGC CTGAGCAGCC GCCTGAGGGT
CTCGGCCACC TTCTGGCAGA ACCCCGCAA CCACTTCCGC TGTCAAGTCC
AGTTCTACGG GCTCTCGGAG AATGACGAGT GGACCCAGGA TAGGGCCAAA
CCCGTCACCC AGATCGTCAG CGCCGAGGCC TGGGGTAGAG CAGACTGTGG
CTTTACCTCG GTGTCCTACC AGCAAGGGGT CCTGTCTGCC ACCATCCTCT
ATGAGATCCT GCTAGGGAAG GCCACCCTGT ATGCTGTGCT GGTCAGCGCC
CTTGTGTTGA TGGCCATGGT CAAGAGAAAG GATTTCTAA
```

TCR Clone Vβ22 beta chain (SEQ ID NO:47)

```
MDTWLVCWAI FSLLKAGLTE PEVTQTPSHQ VTQMGQEVIL RCVPISNHLY
FYWYRQILGQ KVEFLVSFYN NEISEKSEIF DDQFSVERPD GSNFTLKIRS
TKLEDSAMYF CASSADTGTL NTEAFFGQGT RLTVVEDLNK VFPPEVAVFE
PSEAEISHTQ KATLVCLATG FFPDHVELSW WVNGKEVHSG VSTDPQPLKE
QPALNDSRYC LSSRLRVSAT FWQNPRNHFR CQVQFYGLSE NDEWTQDRAK
PVTQIVSAEA WGRADCGFTS VSYQQGVLSA TILYEILLGK ATLYAVLVSA
LVLMAMVKRK DF
```

FIG. 13J

SEQUENCE LISTING

```
<160> NUMBER OF SEQ ID NOS: 53

<210> SEQ ID NO 1
<211> LENGTH: 828
<212> TYPE: DNA
<213> ORGANISM: Artificial Sequence
<220> FEATURE:
<223> OTHER INFORMATION: TCR Clone #24 alpha chain

<400> SEQUENCE: 1
atggagaaga atcctttggc agccccatta ctaatcctct ggtttcatct tgactgcgtg      60
agcagcatac tgaacgtgga acaaagtcct cagtcactgc atgttcagga gggagacagc     120
accaatttca cctgcagctt cccttccagc aatttttatg ccttacactg gtacagatgg     180
gaaactgcaa aaagccccga ggccttgttt gtaatgactt taaatgggga tgaaaagaag     240
aaaggacgaa taagtgccac tcttaatacc aaggagggtt acagctattt gtacatcaaa     300
ggatcccagc ctgaagactc agccacatac ctctgtgcct ttttgtcgaa taacaatgcc     360
agactcatgt ttggagatgg aactcagctg gtggtgaagc ccaatatcca gaaccctgac     420
cctgccgtgt accagctgag agactctaaa tccagtgaca gtctgtctg cctattcacc      480 gattttgatt ctcaaacaaa tgtgtcacaa gtaaggatt ctgatgtgta tatcacagac      540
aaaactgtgc tagacatgag gtctatggac ttcaagagca acagtgctgt ggcctggagc     600
aacaaatctg actttgcatg tgcaaacgcc ttcaacaaca gcattattcc agaagacacc     660
ttcttcccca gcccagaaag ttcctgtgat gtcaagctgg tcgagaaaag ctttgaaaca     720
gatacgaacc taaactttca aaacctgtca gtgattgggt tccgaatcct cctcctgaaa     780
gtggccgggt ttaatctgct catgacgctg cggctgtggt ccagctaa               828

<210> SEQ ID NO 2
<211> LENGTH: 275
<212> TYPE: PRT
<213> ORGANISM: Artificial Sequence
```

```
<220> FEATURE:
<223> OTHER INFORMATION: TCR Clone #24 alpha chain

<400> SEQUENCE: 2

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
                20                  25                  30

Leu His Val Gln Glu Gly Asp Ser Thr Asn Phe Thr Cys Ser Phe Pro
            35                  40                  45

Ser Ser Asn Phe Tyr Ala Leu His Trp Tyr Arg Trp Glu Thr Ala Lys
        50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
                85                  90                  95

Leu Tyr Ile Lys Gly Ser Gln Pro Glu Asp Ser Ala Thr Tyr Leu Cys
            100                 105                 110

Ala Phe Leu Ser Asn Asn Asn Ala Arg Leu Met Phe Gly Asp Gly Thr
        115                 120                 125

Gln Leu Val Val Lys Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 3
<211> LENGTH: 6
<212> TYPE: PRT
<213> ORGANISM: Artificial Sequence
<220> FEATURE:
<223> OTHER INFORMATION: TCR Clone #24 alpha chain CDR1

<400> SEQUENCE: 3

Ser Ser Asn Phe Tyr Ala
1               5

<210> SEQ ID NO 4
<211> LENGTH: 7
<212> TYPE: PRT
<213> ORGANISM: Artificial Sequence
<220> FEATURE:
<223> OTHER INFORMATION: TCR Clone #24 alpha chain CDR2
```

<400> SEQUENCE: 4

Met Thr Leu Asn Gly Asp Glu
1               5

<210> SEQ ID NO 5
<211> LENGTH: 11
<212> TYPE: PRT
<213> ORGANISM: Artificial Sequence
<220> FEATURE:
<223> OTHER INFORMATION: TCR Clone #24 alpha chain CDR3

<400> SEQUENCE: 5

Ala Phe Leu Ser Asn Asn Asn Ala Arg Leu Met
1               5                   10

<210> SEQ ID NO 6
<211> LENGTH: 963
<212> TYPE: DNA
<213> ORGANISM: Artificial Sequence
<220> FEATURE:
<223> OTHER INFORMATION: TCR Clone #24 beta chain

<400> SEQUENCE: 6

```
atgcttagtc ctgacctgcc tgactctgcc tggaacacca ggctcctctg ccatgtcatg      60
ctttgtctcc tgggagcagg ttcagtggct gctggagtca tccagtcccc aagacatctg    120
atcaaagaaa agagggaaac agccactctg aaatgctatc ctatccctag acacgacact    180
gtctactggt accagcaggg tccaggtcag gaccccagt tcctcatttc gttttatgaa      240
aagatgcaga gcgataaagg aagcatccct gatcgattct cagctcaaca gttcagtgac    300
tatcattctg aactgaacat gagctccttg gagctggggg actcagccct gtacttctgt    360
gccagcagct tatgggcag ccataattca cccctccact ttgggaacgg gaccaggctc    420
actgtgacag aggacctgaa caaggtgttc cacccgagg tcgctgtgtt tgagccatca      480
gaagcagaga tctcccacac ccaaaaggcc acactggtgt gcctggccac aggcttcttc    540
cccgaccacg tggagctgag ctggtgggtg aatgggaagg aggtgcacag tggggtcagc    600
acggacccgc agcccctcaa ggagcagccc gccctcaatg actccagata ctgcctgagc    660
agccgcctga gggtctcggc caccttctgg cagaaccccc gcaaccactt ccgctgtcaa    720
gtccagttct acgggctctc ggagaatgac gagtggaccc aggatagggc aaacccgtc    780
acccagatcg tcagcgccga ggcctggggt agagcagact gtggctttac ctcggtgtcc    840
taccagcaag ggtcctgtc tgccaccatc ctctatgaga tcctgctagg gaaggccacc    900
ctgtatgctg tgctggtcag cgccttgtg ttgatggcca tggtcaagag aaaggatttc    960
taa                                                                   963
```

<210> SEQ ID NO 7
<211> LENGTH: 320
<212> TYPE: PRT
<213> ORGANISM: Artificial Sequence
<220> FEATURE:
<223> OTHER INFORMATION: TCR Clone #24 beta chain

<400> SEQUENCE: 7

Met Leu Ser Pro Asp Leu Pro Asp Ser Ala Trp Asn Thr Arg Leu Leu
1               5                   10                  15

Cys His Val Met Leu Cys Leu Leu Gly Ala Gly Ser Val Ala Ala Gly
                20                  25                  30

```
Val Ile Gln Ser Pro Arg His Leu Ile Lys Glu Lys Arg Glu Thr Ala
         35                  40                  45

Thr Leu Lys Cys Tyr Pro Ile Pro Arg His Asp Thr Val Tyr Trp Tyr
 50                  55                  60

Gln Gln Gly Pro Gly Gln Asp Pro Gln Phe Leu Ile Ser Phe Tyr Glu
 65                  70                  75                  80

Lys Met Gln Ser Asp Lys Gly Ser Ile Pro Asp Arg Phe Ser Ala Gln
                 85                  90                  95

Gln Phe Ser Asp Tyr His Ser Glu Leu Asn Met Ser Ser Leu Glu Leu
                100                 105                 110

Gly Asp Ser Ala Leu Tyr Phe Cys Ala Ser Ser Leu Trp Gly Ser His
                115                 120                 125

Asn Ser Pro Leu His Phe Gly Asn Gly Thr Arg Leu Thr Val Thr Glu
130                 135                 140

Asp Leu Asn Lys Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                165                 170                 175

Thr Gly Phe Phe Pro Asp His Val Glu Leu Ser Trp Trp Val Asn Gly
                180                 185                 190

Lys Glu Val His Ser Gly Val Ser Thr Asp Pro Gln Pro Leu Lys Glu
                195                 200                 205

Gln Pro Ala Leu Asn Asp Ser Arg Tyr Cys Leu Ser Ser Arg Leu Arg
                210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
                260                 265                 270

Asp Cys Gly Phe Thr Ser Val Ser Tyr Gln Gln Gly Val Leu Ser Ala
                275                 280                 285

Thr Ile Leu Tyr Glu Ile Leu Leu Gly Lys Ala Thr Leu Tyr Ala Val
290                 295                 300

Leu Val Ser Ala Leu Val Leu Met Ala Met Val Lys Arg Lys Asp Phe
305                 310                 315                 320

<210> SEQ ID NO 8
<211> LENGTH: 5
<212> TYPE: PRT
<213> ORGANISM: Artificial Sequence
<220> FEATURE:
<223> OTHER INFORMATION: TCR Clone #24 beta chain CDR1

<400> SEQUENCE: 8

Pro Arg His Asp Thr
1               5

<210> SEQ ID NO 9
<211> LENGTH: 6
<212> TYPE: PRT
<213> ORGANISM: Artificial Sequence
<220> FEATURE:
<223> OTHER INFORMATION: TCR Clone #24 beta chain CDR2

<400> SEQUENCE: 9

Phe Tyr Glu Lys Met Gln
1               5
```

```
<210> SEQ ID NO 10
<211> LENGTH: 13
<212> TYPE: PRT
<213> ORGANISM: Artificial Sequence
<220> FEATURE:
<223> OTHER INFORMATION: TCR Clone #24 beta chain CDR3

<400> SEQUENCE: 10

Cys Ala Ser Ser Leu Trp Gly Ser His Asn Ser Pro Leu
1               5                   10

<210> SEQ ID NO 11
<211> LENGTH: 819
<212> TYPE: DNA
<213> ORGANISM: Artificial Sequence
<220> FEATURE:
<223> OTHER INFORMATION: TCR Clone #39 Alpha chain

<400> SEQUENCE: 11
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggacgata tgcaggcaa catgctcacc      360 tttggagggg gaacaaggtt aatggtcaaa ccccatatcc agaaccctga ccctgccgtg     420
taccagctga gagactctaa atccagtgac aagtctgtct gcctattcac cgatttgat     480 tctcaaacaa atgtgtcaca agtaaggat tctgatgtgt atatcacaga caaaactgtg     540
ctagacatga ggtctatgga cttcaagagc aacagtgctg tggcctggag caacaaatct     600
gactttgcat gtgcaaacgc cttcaacaac agcattattc agaagacac cttcttcccc      660 agcccagaaa gttcctgtga tgtcaagctg gtcgagaaaa gctttgaaac agatacgaac     720
ctaaactttc aaaacctgtc agtgattggg ttccgaatcc tcctcctgaa agtggccggg     780
tttaatctgc tcatgacgct gcggctgtgg tccagctaa                           819

<210> SEQ ID NO 12
<211> LENGTH: 272
<212> TYPE: PRT
<213> ORGANISM: Artificial Sequence
<220> FEATURE:
<223> OTHER INFORMATION: TCR Clone #39 Alpha chain

<400> SEQUENCE: 12

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95
```

```
Thr Ala Ser Arg Ala Ala Asp Thr Ala Ser Tyr Phe Cys Ala Thr Asp
            100                 105                 110

Asp Asn Ala Gly Asn Met Leu Thr Phe Gly Gly Gly Thr Arg Leu Met
            115                 120                 125

Val Lys Pro His Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
            210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 13
<211> LENGTH: 5
<212> TYPE: PRT
<213> ORGANISM: Artificial Sequence
<220> FEATURE:
<223> OTHER INFORMATION: TCR Clone #39 Alpha chain CDR1

<400> SEQUENCE: 13

Thr Ser Ile Asn Asn
1               5

<210> SEQ ID NO 14
<211> LENGTH: 7
<212> TYPE: PRT
<213> ORGANISM: Artificial Sequence
<220> FEATURE:
<223> OTHER INFORMATION: TCR Clone #39 Alpha chain CDR2

<400> SEQUENCE: 14

Ile Arg Ser Asn Glu Arg Glu
1               5

<210> SEQ ID NO 15
<211> LENGTH: 11
<212> TYPE: PRT
<213> ORGANISM: Artificial Sequence
<220> FEATURE:
<223> OTHER INFORMATION: TCR Clone #39 Alpha chain CDR3

<400> SEQUENCE: 15

Ala Thr Asp Asp Asn Ala Gly Asn Met Leu Thr
1               5                   10

<210> SEQ ID NO 16
<211> LENGTH: 924
<212> TYPE: DNA
<213> ORGANISM: Artificial Sequence
<220> FEATURE:
```

<223> OTHER INFORMATION: TCR Clone #39 Beta chain

<400> SEQUENCE: 16

```
atgggaatca ggctcctctg tcgtgtggcc ttttgtttcc tggctgtagg cctcgtagat      60
gtgaaagtaa cccagagctc gagatatcta gtcaaaagga cgggagagaa agtttttctg     120
gaatgtgtcc aggatatgga ccatgaaaat atgttctggt atcgacaaga cccaggtctg     180
gggctacggc tgatctattt ctcatatgat gttaaaatga agaaaaagg agatattcct      240
gagggtaca gtgtctctag agagaagaag gagcgcttct ccctgattct ggagtccgcc      300
agcaccaacc agacatctat gtacctctgt gccagcagtt ttaccccaga tacgcagtat     360
tttggcccag caccccggct gacagtgctc gaggacctga aaaacgtgtt cccacccgag     420
gtcgctgtgt ttgagccatc agaagcagag atctcccaca cccaaaaggc cacactggtg     480
tgcctggcca caggcttcta ccccgaccac gtggagctga gctggtgggt gaatgggaag     540
gaggtgcaca gtggggtcag cacagacccg cagccctca aggagcagcc cgccctcaat      600
gactccagat actgcctgag cagccgcctg agggtctcgg ccaccttctg gcagaacccc     660
cgcaaccact ccgctgtca agtccagttc tacgggctct cggagaatga cgagtggacc      720
caggataggg ccaaacctgt cacccagatc gtcagcgccg aggcctgggg tagagcagac     780
tgtggcttca cctccgagtc ttaccagcaa ggggtcctgt ctgccaccat cctctatgag     840
atcttgctag gaaggccac cttgtatgcc gtgctggtca gtgccctcgt gctgatggcc      900
atggtcaaga gaaaggattt ctaa                                           924
```

<210> SEQ ID NO 17
<211> LENGTH: 307
<212> TYPE: PRT
<213> ORGANISM: Artificial Sequence
<220> FEATURE:
<223> OTHER INFORMATION: TCR Clone #39 Beta chain

<400> SEQUENCE: 17

```
Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Lys Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Phe Thr Pro Asp Thr Gln Tyr Phe Gly Pro Gly Thr Arg Leu Thr
        115                 120                 125

Val Leu Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175
```

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe
305

<210> SEQ ID NO 18
<211> LENGTH: 5
<212> TYPE: PRT
<213> ORGANISM: Artificial Sequence
<220> FEATURE:
<223> OTHER INFORMATION: TCR Clone #39 Beta chain CDR1

<400> SEQUENCE: 18

Met Asp His Glu Asn
1               5

<210> SEQ ID NO 19
<211> LENGTH: 6
<212> TYPE: PRT
<213> ORGANISM: Artificial Sequence
<220> FEATURE:
<223> OTHER INFORMATION: TCR Clone #39 Beta chain CDR2

<400> SEQUENCE: 19

Ser Tyr Asp Val Lys Met
1               5

<210> SEQ ID NO 20
<211> LENGTH: 10
<212> TYPE: PRT
<213> ORGANISM: Artificial Sequence
<220> FEATURE:
<223> OTHER INFORMATION: TCR Clone #39 Beta chain CDR3

<400> SEQUENCE: 20

Ala Ser Ser Phe Thr Pro Asp Thr Gln Tyr
1               5                   10

<210> SEQ ID NO 21
<211> LENGTH: 816
<212> TYPE: DNA
<213> ORGANISM: Artificial Sequence
<220> FEATURE:
<223> OTHER INFORMATION: TCR Clone #76 alpha chain

<400> SEQUENCE: 21
atggagaccc tcttgggcct gcttatcctt tggctgcagc tgcaatgggt gagcagcaaa      60
caggaggtga cgcagattcc tgcagctctg agtgtcccag aaggagaaaa cttggttctc     120

```
aactgcagtt tcactgatag cgctatttac aacctccagt ggtttaggca ggaccctggg    180
aaaggtctca catctctgtt gcttattcag tcaagtcaga gagagcaaac aagtggaaga    240
cttaatgcct cgctggataa atcatcagga cgtagtactt tatacattgc agcttctcag    300
cctggtgact cagccaccta cctctgtgct gataatcaaa ctggggcaaa caacctcttc    360
tttgggactg gaacgagact caccgttatt ccctatatcc agaaccctga ccctgccgtg    420
taccagctga gagactctaa atccagtgac aagtctgtct gcctattcac cgatttttgat   480 tctcaaacaa atgtgtcaca agtaaggat  tctgatgtgt atatcacaga caaaactgtg    540
ctagacatga ggtctatgga cttcaagagc aacagtgctg tggcctggag caacaaatct    600
gactttgcat gtgcaaacgc cttcaacaac agcattattc cagaagacac cttcttcccc    660
agcccagaaa gttcctgtga tgtcaagctg gtcgagaaaa gctttgaaac agatacgaac    720
ctaaactttc aaaacctgtc agtgattggg ttccgaatcc tcctcctgaa agtggccggg    780
tttaatctgc tcatgacgct gcggctgtgg tccagc                             816
```

<210> SEQ ID NO 22
<211> LENGTH: 272
<212> TYPE: PRT
<213> ORGANISM: Artificial Sequence
<220> FEATURE:
<223> OTHER INFORMATION: TCR Clone #76 alpha chain

<400> SEQUENCE: 22

```
Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Asp Asn
            100                 105                 110

Gln Thr Gly Ala Asn Asn Leu Phe Phe Gly Thr Gly Thr Arg Leu Thr
        115                 120                 125

Val Ile Pro Tyr Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240
```

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
        260                 265                 270

<210> SEQ ID NO 23
<211> LENGTH: 6
<212> TYPE: PRT
<213> ORGANISM: Artificial Sequence
<220> FEATURE:
<223> OTHER INFORMATION: TCR Clone #76 alpha chain CDR1

<400> SEQUENCE: 23

Asp Ser Ala Ile Tyr Asn
1               5

<210> SEQ ID NO 24
<211> LENGTH: 7
<212> TYPE: PRT
<213> ORGANISM: Artificial Sequence
<220> FEATURE:
<223> OTHER INFORMATION: TCR Clone #76 alpha chain CDR2

<400> SEQUENCE: 24

Ile Gln Ser Ser Gln Arg Glu
1               5

<210> SEQ ID NO 25
<211> LENGTH: 11
<212> TYPE: PRT
<213> ORGANISM: Artificial Sequence
<220> FEATURE:
<223> OTHER INFORMATION: TCR Clone #76 alpha chain CDR3

<400> SEQUENCE: 25

Ala Asp Asn Gln Thr Gly Ala Asn Asn Leu Phe
1               5                   10

<210> SEQ ID NO 26
<211> LENGTH: 963
<212> TYPE: DNA
<213> ORGANISM: Artificial Sequence
<220> FEATURE:
<223> OTHER INFORMATION: TCR Clone #76 beta chain

<400> SEQUENCE: 26
atgcttagtc ctgacctgcc tgactctgcc tggaacacca ggctcctctg ccatgtcatg      60
ctttgtctcc tgggagcagg ttcagtggct gctggagtca tccagtcccc aagacatctg     120
atcaaagaaa agagggaaac agccactctg aaatgctatc ctatccctag acacgacact     180
gtctactggt accagcaggg tccaggtcag gacccccagt tcctcatttc gttttatgaa     240
aagatgcaga gcgataaagg aagcatccct gatcgattct cagctcaaca gttcagtgac     300
tatcattctg aactgaacat gagctccttg agctggggg actcagccct gtacttctgt     360
gccagcagcg aggggggta tggaaactat ggctacacct tcggttcggg gaccaggtta     420
accgttgtag aggacctgaa caaggtgttc cacccgagg tcgctgtgtt tgagccatca     480
gaagcagaga tctcccacac ccaaaaggcc acactggtgt gcctggccac aggcttcttc     540
cccgaccacg tggagctgag ctggtgggtg aatgggaagg aggtgcacag tggggtcagc     600
acggacccgc agcccctcaa ggagcagccc gccctcaatg actccagata ctgcctgagc     660
agccgcctga gggtctcggc caccttctgg cagaaccccc gcaaccactt ccgctgtcaa     720

```
gtccagttct acgggctctc ggagaatgac gagtggaccc aggatagggc caaacccgtc    780
acccagatcg tcagcgccga ggcctggggt agagcagact gtggctttac ctcggtgtcc    840
taccagcaag ggtcctgtc tgccaccatc ctctatgaga tcctgctagg gaaggccacc     900
ctgtatgctg tgctggtcag cgcccttgtg ttgatggcca tggtcaagag aaaggatttc    960
taa                                                                  963
```

```
<210> SEQ ID NO 27
<211> LENGTH: 320
<212> TYPE: PRT
<213> ORGANISM: Artificial Sequence
<220> FEATURE:
<223> OTHER INFORMATION: TCR Clone #76 beta chain

<400> SEQUENCE: 27
```

Met Leu Ser Pro Asp Leu Pro Asp Ser Ala Trp Asn Thr Arg Leu Leu
1               5                   10                  15

Cys His Val Met Leu Cys Leu Leu Gly Ala Gly Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Glu Gly Gly Tyr Gly
        115                 120                 125

Asn Tyr Gly Tyr Thr Phe Gly Ser Gly Thr Arg Leu Thr Val Val Glu
    130                 135                 140

Asp Leu Asn Lys Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                165                 170                 175

Thr Gly Phe Phe Pro Asp His Val Glu Leu Ser Trp Trp Val Asn Gly
            180                 185                 190

Lys Glu Val His Ser Gly Val Ser Thr Asp Pro Gln Pro Leu Lys Glu
        195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Phe Thr Ser Val Ser Tyr Gln Gln Gly Val Leu Ser Ala
        275                 280                 285

Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Phe
305                 310                 315                 320

<210> SEQ ID NO 28
<211> LENGTH: 5
<212> TYPE: PRT
<213> ORGANISM: Artificial Sequence
<220> FEATURE:
<223> OTHER INFORMATION: TCR Clone #76 beta chain CDR1

<400> SEQUENCE: 28

Pro Arg His Asp Thr
1               5

<210> SEQ ID NO 29
<211> LENGTH: 6
<212> TYPE: PRT
<213> ORGANISM: Artificial Sequence
<220> FEATURE:
<223> OTHER INFORMATION: TCR Clone #76 beta chain CDR2

<400> SEQUENCE: 29

Phe Tyr Glu Lys Met Gln
1               5

<210> SEQ ID NO 30
<211> LENGTH: 13
<212> TYPE: PRT
<213> ORGANISM: Artificial Sequence
<220> FEATURE:
<223> OTHER INFORMATION: TCR Clone #76 beta chain CDR3

<400> SEQUENCE: 30

Ala Ser Ser Glu Gly Gly Tyr Gly Asn Tyr Gly Tyr Thr
1               5                   10

<210> SEQ ID NO 31
<211> LENGTH: 837
<212> TYPE: DNA
<213> ORGANISM: Artificial Sequence
<220> FEATURE:
<223> OTHER INFORMATION: TCR Clone Vbeta3 Alpha chain

<400> SEQUENCE: 31
atgtcacttt ctagcctgct gaaggtggtc acagcttcac tgtggctagg acctggcatt      60
gcccagaaga taactcaaac ccaaccagga atgttcgtgc aggaaaagga ggctgtgact     120
ctggactgca catatgacac cagtgatcca agttatggtc tattctggta caagcagccc     180
agcagtgggg aaatgatttt tcttatttat cagggtctt atgaccagca aaatgcaaca     240
gaaggtcgct actcattgaa tttccagaag gcaagaaaat ccgccaacct tgtcatctcc     300
gcttcacaac tggggactc agcaatgtac ttctgtgcaa tgagagaggg ctggggcttt     360
ggaaatgaga attaaccctt gggactgga acaagactca ccatcatacc caatatccag     420
aaccctgacc ctgccgtgta ccagctgaga gactctaaat ccagtgacaa gtctgtctgc     480
ctattcaccg atttttgattc tcaaacaaat gtgtcacaaa gtaaggattc tgatgtgtat     540
atcacagaca aaactgtgct agacatgagg tctatggact tcaagagcaa cagtgctgtg     600
gcctggagca caaatctga ctttgcatgt gcaaacgcct tcaacaacag cattattcca     660 gaagacaccct tcttccccag cccagaaagt tcctgtgatg tcaagctggt cgagaaaagc     720

```
tttgaaacag atacgaacct aaactttcaa aacctgtcag tgattgggtt ccgaatcctc    780
ctcctgaaag tggccgggtt taatctgctc atgacgctgc ggctgtggtc cagctaa       837
```

<210> SEQ ID NO 32
<211> LENGTH: 278
<212> TYPE: PRT
<213> ORGANISM: Artificial Sequence
<220> FEATURE:
<223> OTHER INFORMATION: TCR Clone Vbeta3 Alpha chain CDR1

<400> SEQUENCE: 32

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Gly Trp Gly Phe Gly Asn Glu Lys Leu Thr Phe Gly
        115                 120                 125

Thr Gly Thr Arg Leu Thr Ile Ile Pro Asn Ile Gln Asn Pro Asp Pro
    130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
        275
```

<210> SEQ ID NO 33
<211> LENGTH: 7
<212> TYPE: PRT
<213> ORGANISM: Artificial Sequence
<220> FEATURE:
<223> OTHER INFORMATION: TCR Clone Vbeta3 Alpha chain CDR1

<400> SEQUENCE: 33

Thr Ser Asp Pro Ser Tyr Gly
1               5

<210> SEQ ID NO 34
<211> LENGTH: 8
<212> TYPE: PRT
<213> ORGANISM: Artificial Sequence
<220> FEATURE:
<223> OTHER INFORMATION: TCR Clone Vbeta3 Alpha chain CDR2

<400> SEQUENCE: 34

Gln Gly Ser Tyr Asp Gln Gln Asn
1               5

<210> SEQ ID NO 35
<211> LENGTH: 14
<212> TYPE: PRT
<213> ORGANISM: Artificial Sequence
<220> FEATURE:
<223> OTHER INFORMATION: TCR Clone Vbeta3 Alpha chain CDR3

<400> SEQUENCE: 35

Ala Met Arg Glu Gly Trp Gly Phe Gly Asn Glu Lys Leu Thr
1               5                   10

<210> SEQ ID NO 36
<211> LENGTH: 936
<212> TYPE: DNA
<213> ORGANISM: Artificial Sequence
<220> FEATURE:
<223> OTHER INFORMATION: TCR Clone Vbeta3 Beta chain

<400> SEQUENCE: 36

```
atgggaatca ggctcctctg tcgtgtggcc ttttgtttcc tggctgtagg cctcgtagat      60
gtgaaagtaa cccagagctc gagatatcta gtcaaaagga cgggagagaa agttttttctg    120
gaatgtgtcc aggatatgga ccatgaaaat atgttctggt atcgacaaga cccaggtctg    180
gggctacggc tgatctattt ctcatatgat gttaaaatga agaaaaagg agatattcct      240
gagggggtaca gtgtctctag agagaagaag gagcgcttct ccctgattct ggagtccgcc    300
agcaccaacc agacatctat gtacctctgt gccagcagag agaagcgggg ggaagacaca    360
gatacgcagt attttggccc aggcacccgg ctgacagtgc tcgaggacct gaaaaacgtg    420
ttcccacccg aggtcgctgt gtttgagcca tcagaagcag atctcccca cacccaaaag    480
gccacactgg tgtgcctggc cacaggcttc taccccgacc acgtggagct gagctggtgg    540
gtgaatggga aggaggtgca cagtgggggtc agcacagacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag gccaaacct gtcacccaga tcgtcagcgc cgaggcctgg    780
ggtagagcag actgtggctt cacctccgag tcttaccagc aaggggtcct gtctgccacc    840
atcctctatg agatcttgct agggaaggcc accttgtatg ccgtgctggt cagtgccctc    900
gtgctgatgg ccatggtcaa gagaaaggat tcctaa                              936
```

<210> SEQ ID NO 37
<211> LENGTH: 311
<212> TYPE: PRT
<213> ORGANISM: Artificial Sequence

```
<220> FEATURE:
<223> OTHER INFORMATION: TCR Clone Vbeta3 Beta chain

<400> SEQUENCE: 37

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Glu Lys Arg Gly Glu Asp Thr Asp Thr Gln Tyr Phe Gly Pro Gly
        115                 120                 125

Thr Arg Leu Thr Val Leu Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser
305                 310

<210> SEQ ID NO 38
<211> LENGTH: 5
<212> TYPE: PRT
<213> ORGANISM: Artificial Sequence
<220> FEATURE:
<223> OTHER INFORMATION: TCR Clone Vbeta3 Beta chain  CDR1

<400> SEQUENCE: 38

Met Asp His Glu Asn
1               5
```

<210> SEQ ID NO 39
<211> LENGTH: 6
<212> TYPE: PRT
<213> ORGANISM: Artificial Sequence
<220> FEATURE:
<223> OTHER INFORMATION: TCR Clone Vbeta3 Beta chain CDR2

<400> SEQUENCE: 39

Ser Tyr Asp Val Lys Met
1               5

<210> SEQ ID NO 40
<211> LENGTH: 14
<212> TYPE: PRT
<213> ORGANISM: Artificial Sequence
<220> FEATURE:
<223> OTHER INFORMATION: TCR Clone Vbeta3 Beta chain  CDR3

<400> SEQUENCE: 40

Ala Ser Arg Glu Lys Arg Gly Glu Asp Thr Asp Thr Gln Tyr
1               5                   10

<210> SEQ ID NO 41
<211> LENGTH: 834
<212> TYPE: DNA
<213> ORGANISM: Artificial Sequence
<220> FEATURE:
<223> OTHER INFORMATION: TCR Clone Vbeta22 alpha chain

<400> SEQUENCE: 41

```
atggagaaga atcctttggc agccccatta ctaatcctct ggtttcatct tgactgcgtg      60
agcagcatac tgaacgtgga acaaagtcct cagtcactgc atgttcagga gggagacagc     120
accaatttca cctgcagctt cccttccagc aatttttatg ccttacactg gtacagatgg     180
gaaactgcaa aaagccccga ggccttgttt gtaatgactt aaatggggga tgaaaagaag     240
aaaggacgaa taagtgccac tcttaatacc aaggagggtt acagctattt gtacatcaaa     300
ggatcccagc tgaagactc agccacatac ctctgtgcct cgactcgta ctataatgca       360 ggcaacatgc tcacctttgg agggggaaca aggttaatgg tcaaaccca tatccagaac      420 cctgaccctg ccgtgtacca gctgagagac tctaaatcca gtgacaagtc tgtctgccta    480
ttcaccgatt ttgattctca aacaaatgtg tcacaaagta aggattctga tgtgtatatc    540
acagacaaaa ctgtgctaga catgaggtct atggacttca gagcaacag tgctgtggcc     600 tggagcaaca atctgacttt gcatgtgca aacgccttca caacagcat tattccagaa     660 gacaccttct tccccagccc agaaagttcc tgtgatgtca agctggtcga gaaagctt      720 gaaacagata cgaacctaaa ctttcaaaac ctgtcagtga ttgggttccg aatcctcctc    780
ctgaaagtgg ccgggtttaa tctgctcatg acgctgcggc tgtggtccag ctaa           834
```

<210> SEQ ID NO 42
<211> LENGTH: 277
<212> TYPE: PRT
<213> ORGANISM: Artificial Sequence
<220> FEATURE:
<223> OTHER INFORMATION: TCR Clone Vbeta22 alpha chain

<400> SEQUENCE: 42

Met Glu Lys Asn Pro Leu Ala Ala Pro Leu Leu Ile Leu Trp Phe His
1               5                   10                  15

Leu Asp Cys Val Ser Ser Ile Leu Asn Val Glu Gln Ser Pro Gln Ser
            20                  25                  30

```
Leu His Val Gln Glu Gly Asp Ser Thr Asn Phe Thr Cys Ser Phe Pro
            35                  40                  45

Ser Ser Asn Phe Tyr Ala Leu His Trp Tyr Arg Trp Glu Thr Ala Lys
 50                  55                  60

Ser Pro Glu Ala Leu Phe Val Met Thr Leu Asn Gly Asp Glu Lys Lys
 65                  70                  75                  80

Lys Gly Arg Ile Ser Ala Thr Leu Asn Thr Lys Glu Gly Tyr Ser Tyr
                 85                  90                  95

Leu Tyr Ile Lys Gly Ser Gln Pro Glu Asp Ser Ala Thr Tyr Leu Cys
            100                 105                 110

Ala Phe Asp Ser Tyr Tyr Asn Ala Gly Asn Met Leu Thr Phe Gly Gly
            115                 120                 125

Gly Thr Arg Leu Met Val Lys Pro His Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
            210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
            275

<210> SEQ ID NO 43
<211> LENGTH: 6
<212> TYPE: PRT
<213> ORGANISM: Artificial Sequence
<220> FEATURE:
<223> OTHER INFORMATION: TCR Clone Vbeta22 alpha chain CDR1

<400> SEQUENCE: 43

Ser Ser Asn Phe Tyr Ala
1               5

<210> SEQ ID NO 44
<211> LENGTH: 7
<212> TYPE: PRT
<213> ORGANISM: Artificial Sequence
<220> FEATURE:
<223> OTHER INFORMATION: TCR Clone Vbeta22 alpha chain CDR2

<400> SEQUENCE: 44

Met Thr Leu Asn Gly Asp Glu
1               5

<210> SEQ ID NO 45
<211> LENGTH: 13
<212> TYPE: PRT
<213> ORGANISM: Artificial Sequence
```

```
<220> FEATURE:
<223> OTHER INFORMATION: TCR Clone Vbeta22 alpha chain CDR3

<400> SEQUENCE: 45

Ala Phe Asp Ser Tyr Tyr Asn Ala Gly Asn Met Leu Thr
1               5                   10

<210> SEQ ID NO 46
<211> LENGTH: 939
<212> TYPE: DNA
<213> ORGANISM: Artificial Sequence
<220> FEATURE:
<223> OTHER INFORMATION: TCR Clone Vbeta22 beta chain

<400> SEQUENCE: 46
atggatacct ggctcgtatg ctgggcaatt tttagtctct tgaaagcagg actcacagaa      60
cctgaagtca cccagactcc cagccatcag gtcacacaga tgggacagga agtgatcttg     120
cgctgtgtcc ccatctctaa tcacttatac ttctattggt acagacaaat cttggggcag     180
aaagtcgagt ttctggtttc cttttataat aatgaaatct cagagaagtc tgaaatattc     240
gatgatcaat tctcagttga aaggcctgat ggatcaaatt tcactctgaa gatccggtcc     300
acaaagctgg aggactcagc catgtacttc tgtgccagca gcgcagacac cgggacactg     360
aacactgaag cttttctttgg acaaggcacc agactcacag ttgtaggga cctgaacaag     420 gtgttcccac ccgaggtcgc tgtgtttgag ccatcagaag cagagatctc cacacccaa      480 aaggccacac tggtgtgcct ggccacaggc ttcttccccg accacgtgga gctgagctgg     540
tgggtgaatg gaaggaggt gcacagtggg gtcagcacgg accgcagcc cctcaaggag       600 cagcccgccc tcaatgactc cagatactgc ctgagcagcc gcctgagggt ctcggccacc     660
ttctggcaga accccgcaa ccacttccgc tgtcaagtcc agttctacgg gctctcggag      720
aatgacgagt ggacccagga tagggccaaa cccgtcaccc agatcgtcag cgccgaggcc     780
tggggtagag cagactgtgg ctttacctcg gtgtcctacc agcaaggggt cctgtctgcc     840
accatcctct atgagatcct gctagggaag gccaccctgt atgctgtgct ggtcagcgcc     900
cttgtgttga tggccatggt caagagaaag gatttctaa                            939

<210> SEQ ID NO 47
<211> LENGTH: 312
<212> TYPE: PRT
<213> ORGANISM: Artificial Sequence
<220> FEATURE:
<223> OTHER INFORMATION: TCR Clone Vbeta22 beta chain

<400> SEQUENCE: 47

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95
```

```
Lys Ile Arg Ser Thr Lys Leu Glu Asp Ser Ala Met Tyr Phe Cys Ala
            100                 105                 110

Ser Ser Ala Asp Thr Gly Thr Leu Asn Thr Glu Ala Phe Phe Gly Gln
            115                 120                 125

Gly Thr Arg Leu Thr Val Val Glu Asp Leu Asn Lys Val Phe Pro Pro
130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
                180                 185                 190

Thr Asp Pro Gln Pro Leu Lys Glu Gln Pro Ala Leu Asn Asp Ser Arg
                195                 200                 205

Tyr Cys Leu Ser Ser Arg Leu Arg Val Ser Ala Thr Phe Trp Gln Asn
                210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
                260                 265                 270

Tyr Gln Gln Gly Val Leu Ser Ala Thr Ile Leu Tyr Glu Ile Leu Leu
                275                 280                 285

Gly Lys Ala Thr Leu Tyr Ala Val Leu Val Ser Ala Leu Val Leu Met
                290                 295                 300

Ala Met Val Lys Arg Lys Asp Phe
305                 310
```

```
<210> SEQ ID NO 48
<211> LENGTH: 5
<212> TYPE: PRT
<213> ORGANISM: Artificial Sequence
<220> FEATURE:
<223> OTHER INFORMATION: TCR Clone Vbeta22 beta chain CDR1

<400> SEQUENCE: 48

Ser Asn His Leu Tyr
1               5

<210> SEQ ID NO 49
<211> LENGTH: 6
<212> TYPE: PRT
<213> ORGANISM: Artificial Sequence
<220> FEATURE:
<223> OTHER INFORMATION: TCR Clone Vbeta22 beta chain CDR2

<400> SEQUENCE: 49

Phe Tyr Asn Asn Glu Ile
1               5

<210> SEQ ID NO 50
<211> LENGTH: 14
<212> TYPE: PRT
<213> ORGANISM: Artificial Sequence
<220> FEATURE:
<223> OTHER INFORMATION: TCR Clone Vbeta22 beta chain CDR3
```

```
<400> SEQUENCE: 50

Ala Ser Ser Ala Asp Thr Gly Thr Leu Asn Thr Glu Ala Phe
1               5                   10

<210> SEQ ID NO 51
<211> LENGTH: 18
<212> TYPE: PRT
<213> ORGANISM: Artificial Sequence
<220> FEATURE:
<223> OTHER INFORMATION: Furin cleavage site

<400> SEQUENCE: 51

Ala Thr Asn Phe Ser Leu Leu Lys Gln Ala Gly Asp Val Glu Glu Asn
1               5                   10                  15

Pro Gly

<210> SEQ ID NO 52
<211> LENGTH: 81
<212> TYPE: DNA
<213> ORGANISM: Artificial Sequence
<220> FEATURE:
<223> OTHER INFORMATION: Polynucleotide

<400> SEQUENCE: 52
cgtgccaagc gaagcggatc tggcgccacg aacttctctc tgttaaagca agcaggagat      60
gttgaagaaa accccgggcc t                                                81

<210> SEQ ID NO 53
<211> LENGTH: 27
<212> TYPE: PRT
<213> ORGANISM: Artificial Sequence
<220> FEATURE:
<223> OTHER INFORMATION: Polypeptide

<400> SEQUENCE: 53

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
                20                  25
```

T CELL RECEPTORS FOR IMMUNOTHERAPY

The present application is a national phase application under 35 U.S.C. § 371 that claims priority to International Application No. PCT/US2018/055691 filed Oct. 12, 2018, which claims the priority benefit of U.S Provisional Applications Serial No. 62/571,447, filed Oct. 12, 2017, the entire contents of which are being hereby incorporated by reference.

INCORPORATION OF SEQUENCE LISTING

The sequence listing that is contained in the file named "MDACP1188US_ST25.txt", which is 46,582 and was created on Nov. 16, 2023, is filed herewith by electronic submission and is incorporated by reference herein.

BACKGROUND

1. Field

The present invention relates generally to the field of immunology and medicine. More particularly, it concerns T cell receptors (TCR). In some embodiments the TCR and may be used to treat a cancer.

2. Description of Related Art

T cell-based therapies have shown significant promise as a method for treating many cancers; unfortunately, this approach has also been hindered by a paucity of immunogenic antigen targets for common cancers and potential toxicity to non-cancerous tissues. These T cell-based therapies can include adoptive cell transfer (ACT) and vaccination approaches. ACT generally involves infusing a large number of autologous activated tumor-specific T cells into a patient, e.g., to treat a cancer. ACT has resulted in therapeutic clinical responses in melanoma patients (Yee, 2002; Dudley, 2002; Yee, 2014). Generally, to develop effective anti-tumor T cell responses, the following three steps are normally required: priming and activating the antigen-specific T cells, migrating activated T cells to the tumor site, and recognition and killing of the tumor by antigen-specific T cells. The choice of target antigen is important for induction of effective antigen-specific T cells.

While several tumor-associated antigens have been identified for melanoma and a handful of other solid tumor malignancies, there are few immunogenic targets for pancreatic, ovarian, gastric, lung, cervical, breast, and head and neck cancer. Identification and validation of novel epitopes and target antigens for these common and difficult to treat malignancies is warranted.

SUMMARY

In certain embodiments, the present disclosure provides an engineered T cell receptor (TCR) comprising an alpha chain CDR3 having at least 90%, such as 91%, 92%, 93%, 94%, 95%, 96%, 97%, 98%, 99%, or 100%, identity to the amino acid sequence of SEQ ID NO: 5, 15, 25, 35, or 45 and/or a beta chain CDR3 having at least 90%%, such as 91%, 92%, 93%, 94%, 95%, 96%, 97%, 98%, 99%, or 100%, identity to the amino acid sequence of SEQ ID NO: 10, 20, 30, 40, or 50. In particular aspects, the TCR has CDR3 amino acid sequences of SEQ ID NO: 5 and 10, 15 and 20, 25 and 30, 35 and 40, or 45 and 50. In particular aspects, the TCR has CDR1, CDR2, and CDR3 amino acid sequences of SEQ ID NO: 3-5 and 8-10, 13-15 and 18-20, 23-25 and 28-30, 33-35 and 38-40, or 43-45 and 48-50. In some aspects, the engineered TCR binds HLA-A2, HLA-A*0201, HLA-A24, and/or HLA-A*2402.

In certain aspects, the TCR comprises an alpha chain variable region having at least 90%, such as 91%, 92%, 93%, 94%, 95%, 96%, 97%, 98%, 99%, or 100%, identity to the amino acid sequence of SEQ ID NO: 2, 12, 22, 32, or 42 and/or a beta chain variable region having at least 90%, such as 91%, 92%, 93%, 94%, 95%, 96%, 97%, 98%, 99%, or 100%, identity to the amino acid sequence of SEQ ID NO: 7, 17, 27, 37, or 47. In particular aspects, the TCR comprises an alpha chain of SEQ ID NO: 2, 12, 22, 32, or 42 and/or a beta chain of SEQ ID NO: 7, 17, 27, 37, or 47. In some aspects, the TCR may comprise an alpha chain and beta chain of SEQ ID NO: 2 and 7, 12 and 17, 22 and 27, 32 and 37, or 42 and 47, respectively. In particular aspects, the TCR may have variation in the sequence of the variable regions of the alpha and/or beta chain while keeping the sequences of the CDR regions constant.

In some aspects, the TCR comprises an alpha chain having at least 90%, such as 91%, 92%, 93%, 94%, 95%, 96%, 97%, 98%, 99%, or 100%, identity to the nucleotide sequence of SEQ ID NO: 1, 11, 21, 31, or 41 and/or a beta chain having at least 90%, such as 91%, 92%, 93%, 94%, 95%, 96%, 97%, 98%, 99%, or 100%, identity to the nucleotide sequence of SEQ ID NO: 6, 16, 26, 36, or 46. In specific aspects, the TCR comprises an alpha chain comprising the nucleotide sequence of SEQ ID NO: 1, 11, 21, 31, or 41 and/or a beta chain comprising the nucleotide sequence of SEQ ID NO: 6, 16, 26, 36, or 46.

In certain aspects, the TCR is further defined as a soluble TCR, wherein the soluble TCR does not comprise a transmembrane domain.

In some aspects, the TCR further comprises a detectable label. In certain aspects, the TCR is covalently bound to a therapeutic agent. In specific aspects, the therapeutic agent is an immunotoxin or a chemotherapeutic agent.

Further provided herein is a multivalent TCR complex comprising a plurality of TCRs of the embodiments. In some aspects, the multivalent TCR comprises 2, 3, 4 or more TCRs associated with one another. In particular aspects, the multivalent TCR is present in a lipid bilayer, in a liposome, or is attached to a nanoparticle. In some aspects, the TCRs are associated with one another via a linker molecule.

In another embodiment, there is provided a polypeptide encoding the TCR of the embodiments. Also provided herein is a polynucleotide encoding the polypeptide of the embodiments.

Further embodiments provide an expression vector encoding the TCR of the embodiments. In some aspects, the sequence encoding the TCR is under the control of a promoter. In particular aspects, the expression vector is a viral vector. In one specific aspect, the viral vector is a retroviral vector. In some aspects, the vector further encodes a linker domain. In some aspects, the linker domain is positioned between the alpha chain and beta chain. In certain aspects, the linker domain comprises one or more cleavage sites. In some aspects, the one or more cleavage sites are a Furin cleavage site and/or a P2A cleavage site. In some aspects, the Furin cleavage site is RAKR. In other aspects, the Furin cleavage site is ATNFSLLKQAGDVEENPG (SEQ ID NO:51). In certain aspects, the one or more cleavage sites are separated by a spacer. In specific aspects, the spacer is SGSG or GSG.

In another embodiment, there is provided a host cell engineered to express the TCR of the embodiments. In some aspects, the cell is a T cell, NK cell, invariant NK cell, NKT cell, mesenchymal stem cell (MSC), or induced pluripotent stem (iPS) cell. In certain aspects, the host cell is an immune cell. In particular aspects, the host cell is isolated from an umbilical cord. In some aspects, the T cell is a CD8+ T cell, CD4+ T cell, or γδ T cell. In particular aspects, the T cell is a regulatory T cell (Treg). In some aspects, the cell is autologous. In particular aspects, the cell is allogeneic.

A further embodiment provides a method for engineering the host cell of the embodiments comprising contacting said immune cell with the TCR of the embodiments or the expression vector of the embodiments. In some aspects, the immune cell is a T cell or a peripheral blood lymphocyte. In certain aspects, contacting is further defined as transfecting or transducing. In some aspects, transfecting comprises electroporating RNA encoding the TCR of the embodiments into the immune cell.

In additional aspects, the method further comprises generating viral supernatant from the expression vector encoding the TCR of the embodiments prior to transducing the immune cell.

In some aspects, the immune cell is a stimulated lymphocyte. In certain aspects, the stimulated lymphocyte is a human lymphocyte. In certain aspects, stimulating comprises contacting the immune cell with or incubating the immune cell in OKT3 and/or IL-2.

In some aspects, the method further comprises sorting the immune cells to isolate TCR engineered T cells. In certain aspects, the method further comprises performing T cell cloning by serial dilution. In some aspects, the method further comprises expansion of the T cell clone by the rapid expansion protocol.

In another embodiment, there is provided a method of treating cancer in a subject comprising administering an effective amount of the TCR-engineered cells of the embodiments to the subject. In some aspects, the subject is identified to have an HLA-A*0201 allele or an HLA-A*2402 allele. In some aspects, the subject is a human.

In certain aspects, the TCR-engineered cell is a T cell or peripheral blood lymphocyte. In specific aspects, the T cell is a CD8+ T cell, CD4+ T cell, or Treg.

In some aspects, the cancer is a melanoma. In particular aspects, the melanoma is a cutaneous melanoma, a uveal melanoma, a mucosal melanoma, or a metastatic melanoma. In certain aspects, the TCR engineered cells are autologous or allogeneic.

In additional aspects, the method further comprises lymphodepletion of the subject prior to administration of the SLC45A2-specific T cells. In some aspects, lymphodepletion comprises administration of cyclophosphamide and/or fludarabine.

In some aspects, the method further comprises administering a second anticancer therapy. In certain aspects, the therapy is a chemotherapy, immunotherapy, surgery, radiotherapy, or biotherapy. In some aspects, the TCR-engineered cells, and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion. In certain aspects, the subject is determined to have cancer cells which overexpress SLC45A2.

In certain embodiments, the present disclosure provides TCR that selectively bind SLC45A2. In some embodiments, the alpha and beta portions of a TCR sequence provided herein may be included in a chimeric antigen receptor (CAR) that may be used in an adoptive T cell therapy. In some embodiments, the alpha and beta portions of the TCR may be encoded in a DNA that can be used, e.g., to treat a melanoma. Alternately, the alpha and beta variable regions of the TCR may be included in a protein, such as a TCR or a solubilized protein, and used in an anti-cancer therapy such as an adoptive immunotherapy. In some preferred embodiments, the TCR, CAR, or soluble peptide selectively binds SLC45A2 at a particular epitope, such as $SLC45A2_{382-390}$ or $SLC45A2_{393-402}$ immunogenic epitopes. It is anticipated that the TCR may result in a reduction in toxicity towards non-cancerous cells and may be particularly useful for the treatment of melanomas (e.g., cutaneous melanoma, uveal melanoma, mucosal melanoma). In some embodiments, the cloned T cell receptors may be included in a chimeric T cell receptor (CAR) and used in an adoptive T cell transfer or immunotherapy.

In some aspects, the present disclosure provides soluble TCRs that can be used to treat HLA-A2 positive cancer patients directly. The soluble bispecific T cell-engaging molecules can be generated by linking the SLC45A2 TCR to CD3-specific Fab fragments. The T cell-engaging TCR can bind the tumor cell surface by presenting the respective peptide/MHC complex and the Fab fragments then crosslink TCRs on the surface of antigen-experienced CD8+ T cells, resulting in cellular activation and elimination of the target cell. Thus, this soluble bispecific TCR constructs can be used for treating the cancer patients directly.

Finally, the soluble TCR can be used as a probe for diagnostic evaluation of peptide/MHC in tumor cells or to direct therapeutic molecules to the tumor site. This soluble TCR molecule also could be labeled with tracers such as a fluorescent probe or radioactive probe, and then used for diagnostic evaluation of the presentation of peptide/MHC in tumor cells. Furthermore, this soluble TCR molecule could be linked with therapeutic molecules, such as a toxin, so as to direct these therapeutic molecules to the tumor sites for the treatment of cancer patients.

In certain aspects, the SLC45A2-specific T cells, optionally in combination with a second therapeutic agent, can be administered intravenously, intraperitoneally, intratracheally, intratumorally, intramuscularly, endoscopically, intralesionally, percutaneously, subcutaneously, regionally, or by direct injection or perfusion.

Yet another aspect of the present disclosure relates to a pharmaceutical composition comprising the peptide of the present disclosure or as described above and an excipient. The pharmaceutical preparation may be formulated for parenteral administration, intravenous injection, intramuscular injection, inhalation, or subcutaneous injection. In some embodiments, the peptide is comprised in a liposome, lipid-containing nanoparticle, or in a lipid-based carrier.

Another aspect of the present disclosure relates to particular T cell receptor variable regions (e.g., SEQ ID NO: 51-70).

The term "chimeric antigen receptors (CARs)," as used herein, may refer to artificial T cell receptors, chimeric T cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

HLA-A2 refers to the human leukocyte antigen serotype A2 and is also referred to as HLA-A*02. Several serotypes of the gene products of many HLA-A*02 alleles are well known, including HLA-A*0201, *0202, *0203, *0206, *0207, and *0211 gene products.

HLA-A24 refers to the human leukocyte antigen serotype A24 and is also referred to as HLA-A*24. Several serotypes of the gene products of many HLA-A*24 alleles are well known, including HLA-A*2402 and *2403 gene products.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

The terms "about", "substantially" and "approximately" mean, in general, the stated value plus or minus 5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-B: Specific lysis of target cells by TCR-transfected T cells. Cytotoxic activity of TCR clone # Vb3 by Chromium release assay using Mel526 (HLA A2$^+$) and Mel888 (HLA A2$^-$) cells. To test cytotoxic activity of parental T cells, standard chromium release assay was performed and was compared between TCR-transfected T cells and parental T cell clones. FIG. 2A, TCR-transfected T cells can lyse the HLA-A24-matched target, Mel888, but not the HLA-A24 mismatched target, Mel526, both of which express SLC45A2. FIG. 2B, Cytotoxic activity of parental T cells showed similar lysis.

FIGS. 3A-B: Stable expression of TCR using TCR retrovirus. SLC45A2 tetramer and CD8 staining of TCR clone Vb3 and parental clone. FIG. 3A, Activated autologous PBMCs were transduced with retrovirus including the TCR gene. After 8 days, T cells were stained with SLC45A2-PE conjugated tetramer. SLC45A2 tetramer-positive T cells were sorted and subjected to REP. FIG. 3B, Parental T cells clones were generated from autologous PMBC.

FIG. 4A, TCR-transfected T cells can lyse the HLAA24-matched target, Mel888, but not the HLA-A24 mismatched target, Mel526, both of which express SLC45A2. FIG. 4B, Cytotoxic activity of parental T cells showed similar lysis.

FIG. 5A, Activated autologous PBMCs were transduced with retrovirus including the TCR gene. After 8 days, T cells were stained with SLC45A2-PE conjugated tetramer. SLC45A2 tetramer-positive T cells were sorted and subjected to REP. FIG. 5B, Parental T cells clones were generated from autologous PMBC.

FIG. 6A, TCR-transfected T cells can lyse the HLA-A24-matched target, Mel888, but not the HLA-A24 mismatched target, Mel526, both of which express SLC45A2. FIG. 6B, Cytotoxic activity of parental T cells showed similar lysis.

FIG. 7A, Activated autologous PBMCs were transduced with retrovirus including the TCR gene. After 8 days, T cells were stained with SLC45A2-PE conjugated tetramer. SLC45A2 tetramer-positive T cells were sorted and subjected to REP. FIG. 7B, Parental T cells clones were generated from autologous PMBC.

FIGS. 13A-13J: Sequences for alpha and beta chains of each TCR clone including Clone #24 (FIGS. 13A-B), Clone #39 (FIGS. 13C-D), Clone #76 (FIGS. 13E-F), Clone Vβ3 (FIGS. 13G-H), and Clone Vβ22 (FIGS. 13I-J). Underlined: Signal peptide; Highlighted: Variable region; Underlined: CDR1, CDR2, CDR3; Black: Constant region.

DESCRIPTION OF ILLUSTRATIVE EMBODIMENTS

I. Engineered Antigen Receptors

Figure 1:
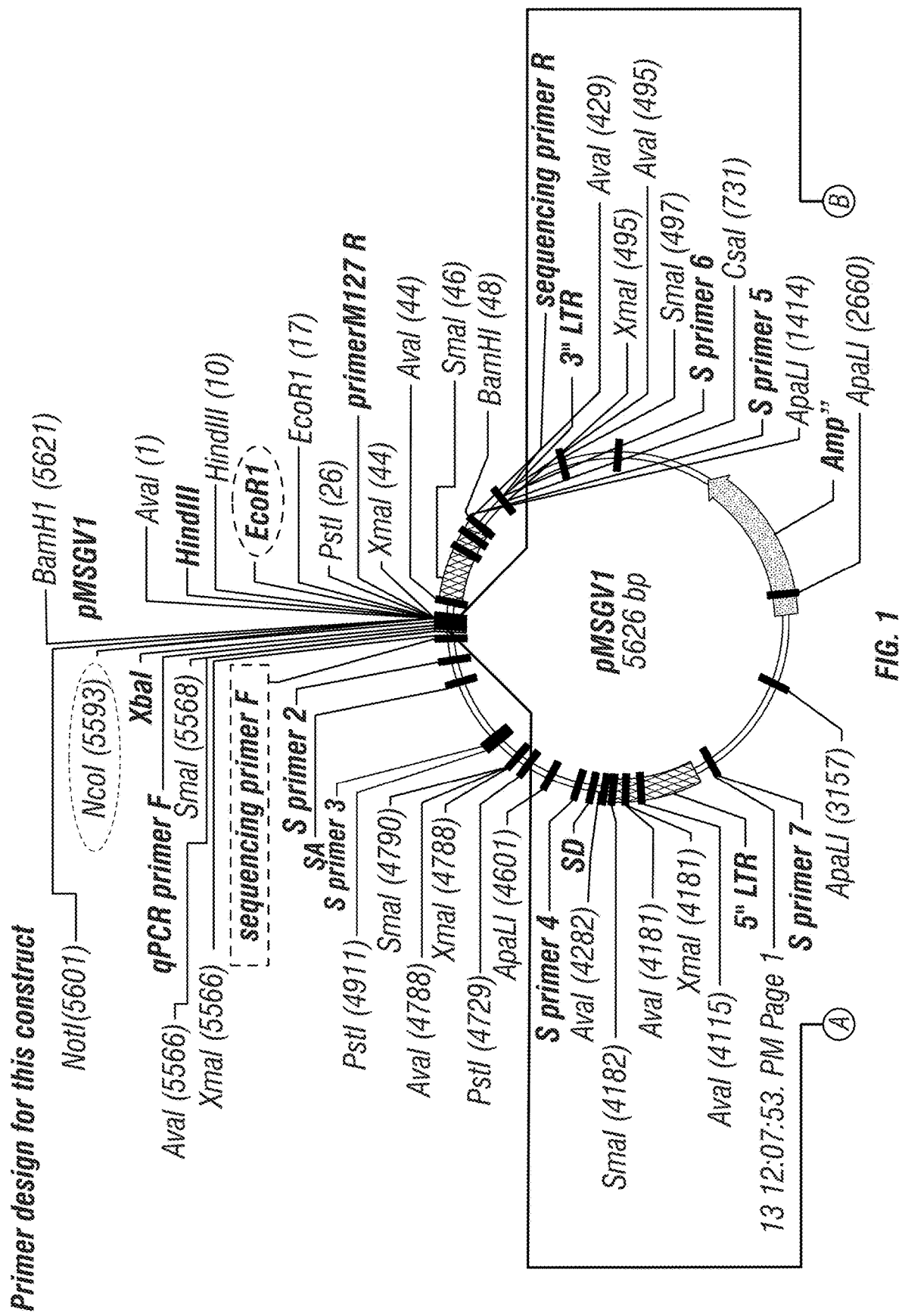
FIG. 1: Schematic depicting retrovirus construct comprising TCR beta chain, peptide linker, and TCR alpha chain. SEQ ID NO:52 is the nucleotide sequence, and SEQ ID NO:53 is protein sequence.
Figure 1:
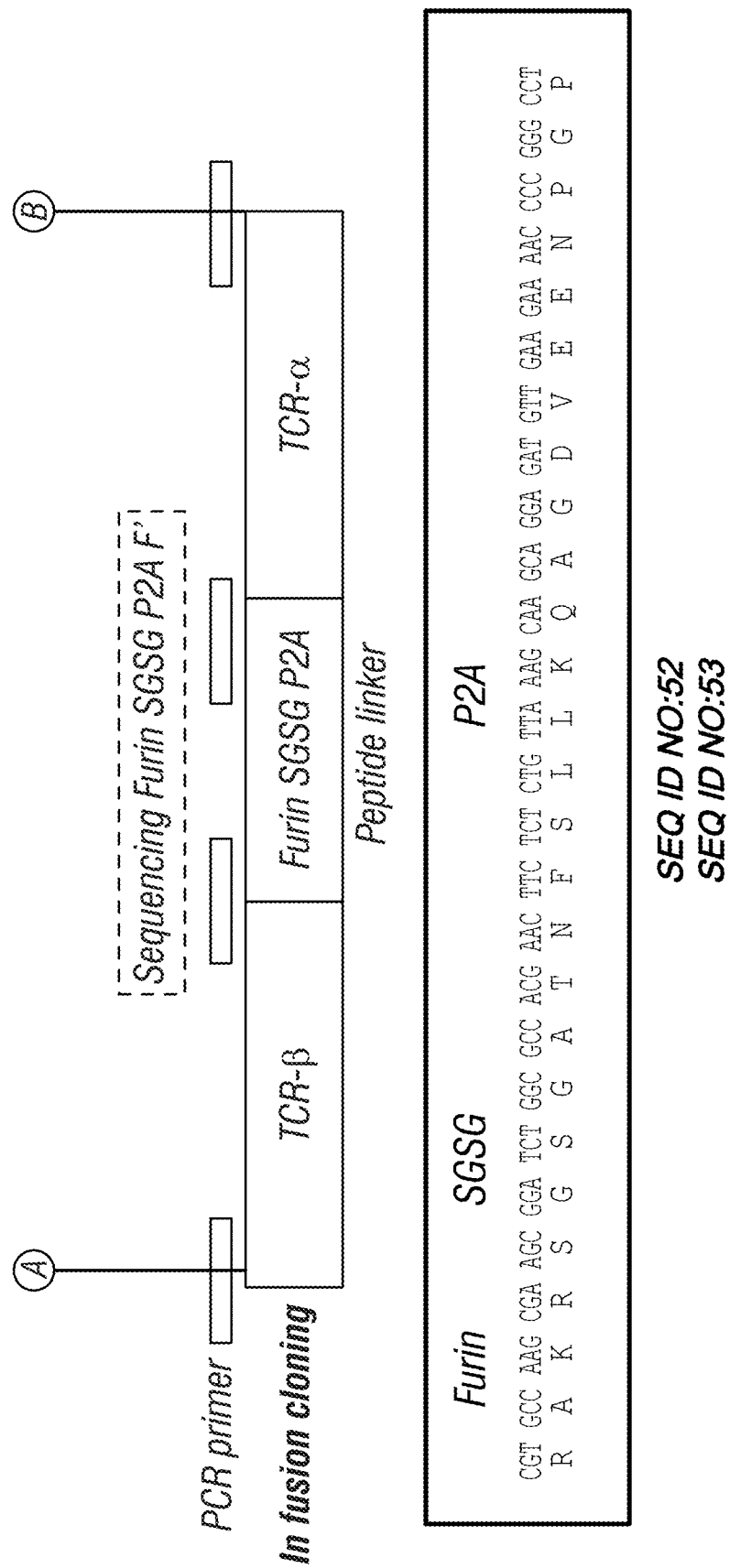
Figure 4A:
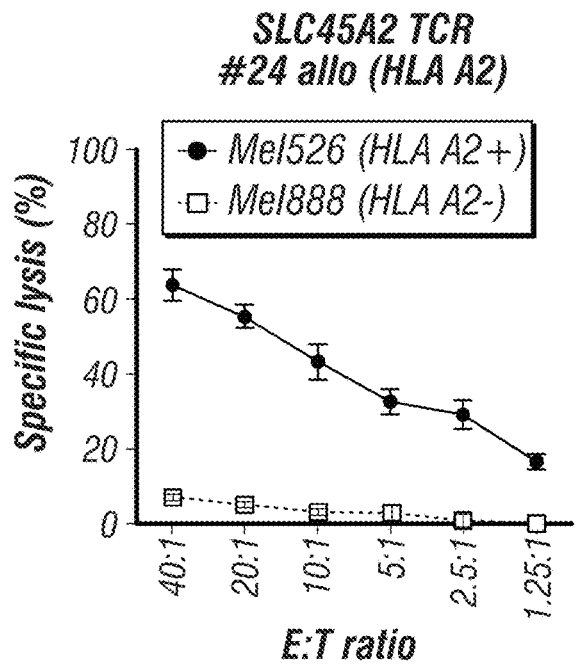
FIGS. 4A-B: Specific lysis of target cells by TCR-transfected T cells. Cytotoxic activity of TCR clone #24 by Chromium release assay using Mel526 (HLA A2$^+$) and Mel888 (HLA A2$^-$) cells. To test cytotoxic activity of parental T cells, standard chromium release assay was performed and was compared between TCR-transfected T cells and parental T cell clones.
Figure 4B:
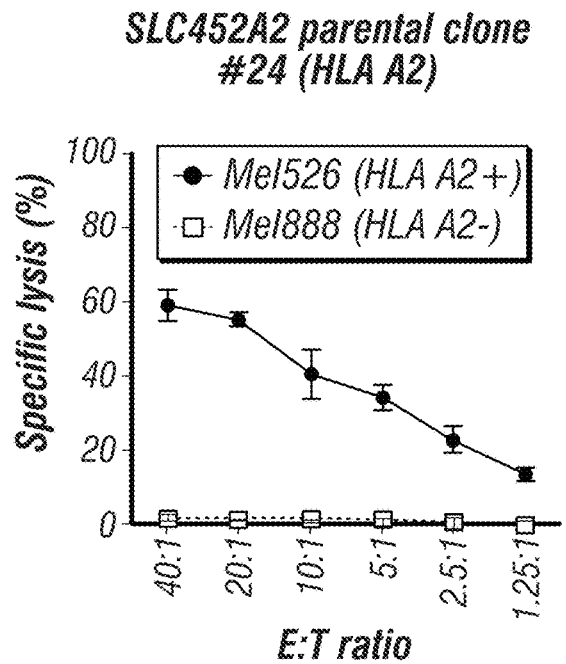
Figure 5A:
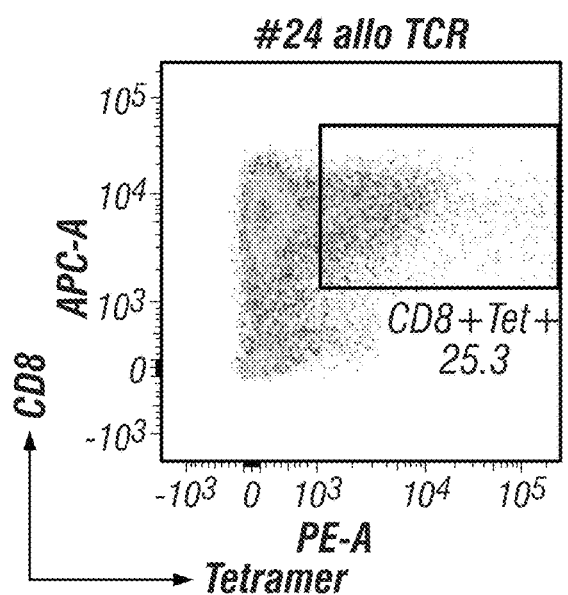
FIGS. 5A-B: Stable expression of TCR using TCR retrovirus. SLC45A2 tetramer and CD8 staining of TCR clone #24 and parental clone.
Figure 5B:
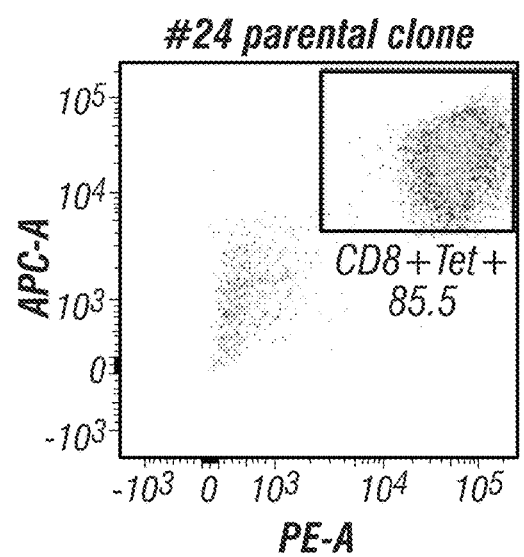
Figure 6A:
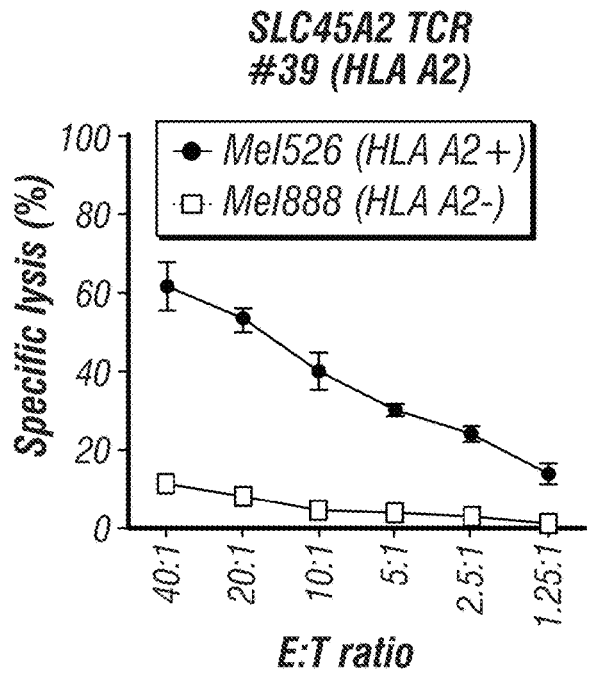
FIGS. 6A-B: Specific lysis of target cells by TCR-transfected T cells. Cytotoxic activity of TCR clone #39 by Chromium release assay using Mel526 (HLA A2$^+$) and Mel888 (HLA A2$^-$) cells. To test cytotoxic activity of parental T cells, standard chromium release assay was performed and was compared between TCR-transfected T cells and parental T cell clones.
Figure 6B:
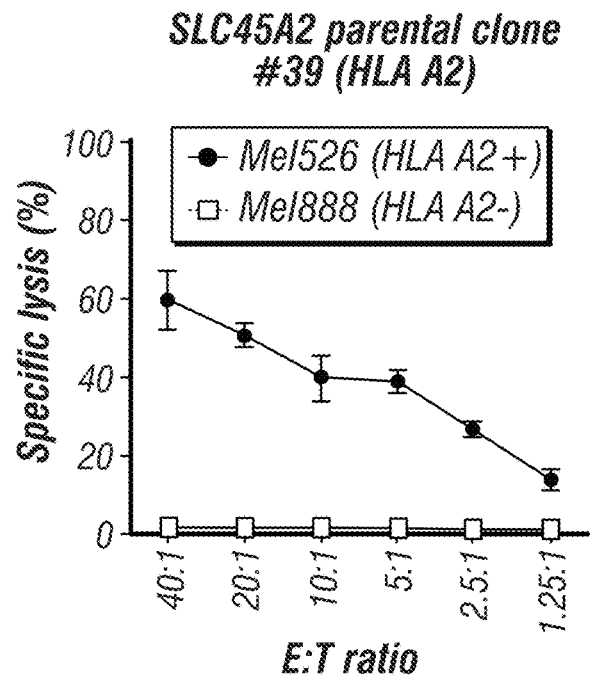
Figure 7A:
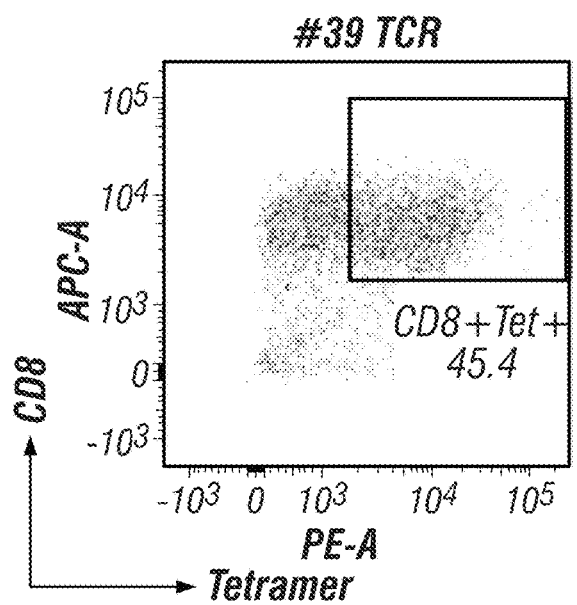
FIGS. 7A-B: Stable expression of TCR using TCR retrovirus. SLC45A2 tetramer and CD8 staining of TCR clone #39 and parental clone.
Figure 7B:
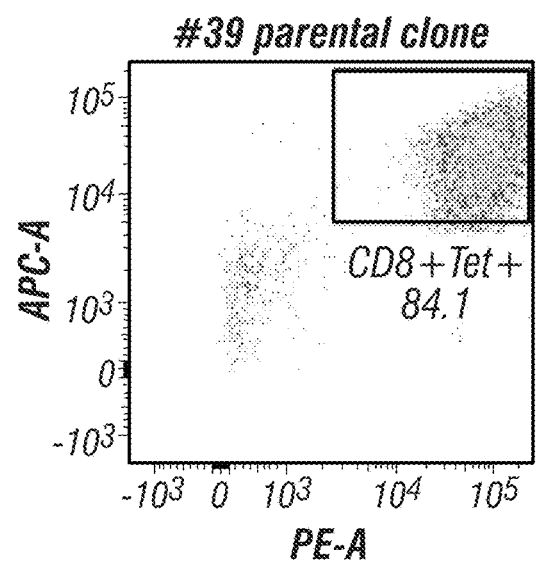

In various aspects, T cell receptors (TCR) that specifically bind the SLC45A2 or a SLC45A2 peptide of the present disclosure are provided herein (e.g., SEQ ID NOs: 1-50). The antigen binding region of the TCR may be included in a chimeric antigen receptor (CAR) as the extracellular domain comprising an antigen binding region. The TCR may be transfected into cells (e.g., autologous or allogeneic cells) that may be used in an adoptive cell transfer therapy. In some embodiments, the CAR is humanized to reduce immunogenicity (hCAR).

In some embodiments, host cells, such as T cells (e.g., CD4+ T cells, CD8+ T cells, γδ T cells, and Tregs), NK cells, invariant NK cells, NKT cells, mesenchymal stem cells (MSCs), induced pluripotent stem (iPS) cells of the present disclosure can be genetically engineered to express antigen receptors such as engineered TCRs and/or chimeric antigen receptors (CARs). For example, the autologous or allogeneic cells (e.g., isolated from an umbilical cord) are modified to express a T cell receptor (TCR) having antigenic specificity for a cancer antigen. In particular embodiments, the antigen receptors have antigenic specificity for SLC45A2, such as peptides SLC45A2$_{382-390}$ or SLC45A2$_{393-402}$ peptides. In certain embodiments, the engineered TCR has an alpha chain CDR3 with at least 90, 91, 92, 93, 94, 95, 96, 97, 98, 99, or 100% sequence identity to SEQ ID NO: 5, 15, 25, 35, or 45 and/or a beta chain CDR3 with at least 90, 91, 92, 93, 94, 95, 96, 97, 98, 99, or 100% sequence identity to SEQ ID NO: 10, 20, 30, 40, or 50. In some embodiments, the TCR has an alpha chain with at least 90, 91, 92, 93, 94, 95, 96, 97, 98, 99, or 100% sequence identity to SEQ ID NO: 1, 2, 11, 12, 21, 22, 31, 32, 41 or 42 and/or a beta chain with at least 90, 91, 92, 93, 94, 95, 96, 97, 98, 99, or 100% sequence identity to SEQ ID NO: 6, 7, 16, 17, 26, 27, 36, 37, 46, or 47. Suitable methods of modification are known in the art. See, for instance, Sambrook and Ausubel, supra. For example, the T cells may be transduced to express a T cell receptor (TCR) having antigenic specificity for a cancer antigen using transduction techniques described in Heemskerk et al. *Hum Gene Ther.* 19:496-510 (2008) and Johnson et al. *Blood* 114:535-46 (2009).

Electroporation of RNA coding for the full length TCR α and β (or γ and δ) chains can be used as alternative to overcome long-term problems with autoreactivity caused by pairing of retrovirally transduced and endogenous TCR chains. Even if such alternative pairing takes place in the transient transfection strategy, the possibly generated autoreactive T cells will normally lose this autoreactivity after some time, because the introduced TCR α and β chain are only transiently expressed. When the introduced TCR α and β chain expression is diminished, only normal autologous T cells are left. This is not the case when full length TCR chains are introduced by stable retroviral transduction, which do not lose the introduced TCR chains, causing a constantly present autoreactivity in the patient.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., *Cancer Discov.* 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer,* 2012 Mar. 18(2): 160-75. In some aspects, the genetically engineered antigen receptors include a CAR as described in U.S. Pat. No. 7,446,190, and those described in International Patent Application Publication No.: WO/2014055668 A1.

A. T Cell Receptor (TCR)

In some embodiments, the genetically engineered antigen receptors include recombinant T cell receptors (TCRs) and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form. In certain embodiments, the engineered TCR has an alpha chain CDR3 of SEQ ID NO: 5, 15, 25, 35, or 45 and/or a beta chain CDR3 of SEQ ID NO: 10, 20, 30, 40, or 50. In some embodiments, the TCR has an alpha chain of SEQ ID NO:1, 2, 11, 12, 21, 22, 31, 32, 41 or 42 and a beta chain of SEQ ID NO: 6, 7, 16, 17, 26, 27, 36, 37, 46, or 47, respectively.

Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, Immunobiology: The Immune System in Health and Disease, $3^{rd}$ Ed., Current Biology Publications, p. 433, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable a chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., *PNAS U.S.A.* 87:9138, 1990; Chothia et al., *EMBO J.* 7:3745, 1988; see also Lefranc et al., *Dev. Comp. Immunol.* 27:55, 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., a-chain, β-chain) can contain two immunoglobulin domains, a variable domain (e.g., $V_a$ or Vβ; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., a-chain constant domain or $C_a$, typically amino acids 117 to 259 based on Kabat, β-chain constant domain or Cβ, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T cell hybridomas or other publicly available source. In some embodiments, the T cells can be obtained from in vivo isolated cells. In some embodiments, a high-affinity T cell clone can be isolated from a patient, and the TCR isolated. In some embodiments, the T-cells can be a cultured T cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15: 169-180 and Cohen et al. (2005) *J Immunol.* 175:5799-5808). In some embodiments, phage display is used to isolate TCRs against a target antigen (see, e.g., Varela-Rohena et al. (2008) *Nat Med.* 14: 1390-1395 and Li (2005) *Nat Biotechnol.* 23:349-354). In some embodiments, the TCR or antigen-binding portion thereof can be synthetically generated from knowledge of the sequence of the TCR.

B. Chimeric T Cell Receptors

In some embodiments, the engineered antigen receptors include chimeric antigen receptors (CARs), including activating or stimulatory CARs, costimulatory CARs (see WO2014/055668), and/or inhibitory CARs (iCARs, see Fedorov et al., Sci. Transl. Medicine, 5(215) (December, 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

The arrangement of the antigen-binding domain of a CAR may be multimeric, such as a diabody or multimers. The multimers can be formed by cross pairing of the variable portions of the light and heavy chains into what may be referred to as a diabody. The hinge portion of the CAR may in some embodiments be shortened or excluded (i.e., generating a CAR that only includes an antigen binding domain, a transmembrane region and an intracellular signaling domain). A multiplicity of hinges may be used with the present invention, e.g., as shown in Table 1. In some embodiments, the hinge region may have the first cysteine maintained, or mutated by a proline or a serine substitution, or be truncated up to the first cysteine. The Fc portion may be deleted from scFv used to as an antigen-binding region to generate CARs according to the present invention. In some embodiments, an antigen-binding region may encode just one of the Fc domains, e.g., either the CH2 or CH3 domain from human immunoglobulin. One may also include the hinge, CH2, and CH3 region of a human immunoglobulin that has been modified to improve dimerization and oligermerization. In some embodiments, the hinge portion of may comprise or consist of a 8-14 amino acid peptide (e.g., a 12 AA peptide), a portion of CD8α, or the IgG4 Fc. In some embodiments, the antigen binding domain may be suspended from cell surface using a domain that promotes oligomerization, such as CD8 alpha. In some embodiments, the antigen binding domain may be suspended from cell surface using a domain that is recognized by monoclonal antibody (mAb) clone 2D3 (mAb clone 2D3 described, e.g., in Singh et al., 2008).

The endodomain or intracellular signaling domain of a CAR can generally cause or promote the activation of at least one of the normal effector functions of an immune cell comprising the CAR. For example, the endodomain may promote an effector function of a T cell such as, e.g., cytolytic activity or helper activity including the secretion of cytokines. The effector function in a naive, memory, or memory-type T cell may include antigen-dependent proliferation. The terms "intracellular signaling domain" or "endodomain" refers to the portion of a CAR that can transduce the effector function signal and/or direct the cell to perform a specialized function. While usually the entire intracellular signaling domain may be included in a CAR, in some cases a truncated portion of an endodomain may be included. Generally, endodomains include truncated endodomains, wherein the truncated endodomain retains the ability to transduce an effector function signal in a cell.

In some embodiments, an endodomain comprises the zeta chain of the T cell receptor or any of its homologs (e.g., eta, delta, gamma, or epsilon), MB1 chain, B29, Fc RIII, Fc RI, and combinations of signaling molecules, such as CD3C and CD28, CD27, 4-1BB, DAP-10, OX40, and combinations thereof, as well as other similar molecules and fragments. Intracellular signaling portions of other members of the families of activating proteins can be used, such as FcγRIII and FcεRI. Examples of these alternative transmembrane and intracellular domains can be found, e.g., Gross et al. (1992), Stancovski et al. (1993), Moritz et al. (1994), Hwu et al. (1995), Weijtens et al. (1996), and Hekele et al. (1996), which are incorporated herein be reference in their entirety. In some embodiments, an endodomain may comprise the human CD3ζ intracellular domain.

The antigen-specific extracellular domain and the intracellular signaling-domain are preferably linked by a transmembrane domain. Transmembrane domains that may be included in a CAR include, e.g., the human IgG4 Fc hinge and Fc regions, the human CD4 transmembrane domain, the human CD28 transmembrane domain, the transmembrane human CD3ζ domain, or a cysteine mutated human CD3ζ domain, or a transmembrane domains from a human transmembrane signaling protein such as, e.g., the CD16 and CD8 and erythropoietin receptor. Examples of transmembrane domains are provided, e.g., in Table 1.

In some embodiments, the endodomain comprises a sequence encoding a costimulatory receptor such as, e.g., a modified CD28 intracellular signaling domain, or a CD28, CD27, OX-40 (CD134), DAP10, or 4-1BB (CD137) costimulatory receptor. In some embodiments, both a primary signal initiated by CD3ζ, an additional signal provided by a human costimulatory receptor may be included in a CAR to more effectively activate a transformed T cells, which may help improve in vivo persistence and the therapeutic success of the adoptive immunotherapy. As noted in Table 1, the endodomain or intracellular receptor signaling domain may comprise the zeta chain of CD3 alone or in combination with an Fcγ RIII costimulatory signaling domains such as, e.g., CD28, CD27, DAP10, CD137, OX40, CD2, 4-1BB. In some embodiments, the endodomain comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, 1, 2, 3, 4 or more cytoplasmic domains may be included in an endodomain.

For example, in some CARs it has been observed that at least two or three signaling domains fused together can result in an additive or synergistic effect.

In some aspects, an isolated nucleic acid segment and expression cassette including DNA sequences that encode a CAR may be generated. A variety of vectors may be used. In some preferred embodiments, the vector may allow for delivery of the DNA encoding a CAR to immune such as T cells. CAR expression may be under the control of regulated eukaryotic promoter such as, e.g., the MNDU3 promoter, CMV promoter, EF1alpha promoter, or Ubiquitin promoter. Also, the vector may contain a selectable marker, if for no other reason, to facilitate their manipulation in vitro. In some embodiments, the CAR can be expressed from mRNA in vitro transcribed from a DNA template.

Chimeric antigen receptor molecules are recombinant and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they can bind native antigen on the target cell surface in an HLA-independent fashion. For example, a scFv constructs may be fused to sequences coding for the intracellular portion of the CD3 complex's zeta chain (ζ), the Fc receptor gamma chain, and sky tyrosine kinase (Eshhar et al., 1993; Fitzer-Attas et al., 1998). Re-directed T cell effector mechanisms including tumor recognition and lysis by CTL have been documented in several murine and human antigen-scFv: systems (Eshhar et al., 1997; Altenschmidt et al., 1997; Brocker et al., 1998).

In some embodiments, a TCR is included in a CAR as the antigen binding domain (e.g., as a scFv region) and the CAR further comprises a hinge region, a transmembrane region, and an endodomain. For example, the TCR (e.g., SEQ ID NOs: 51-70) may be included in a CAR with a hinge region, a transmembrane region, and an endodomain as described in Table 1 below.

TABLE 1

Regions that may be included in an anti-SLC45A2 targeting CAR

Hinge/Scaffold

12 AA (peptide)
t-20 AA (peptide)
CD8 α
IgG4 Fc
2D3
IgG4 Fc Δ EQ (IgG4Fc N40Q )
IgG4 Fc Δ Q (IgG4Fc L18E N40Q)
t-12AA + t-20AA
mKate
phiLov
dsRed
Venus
eGFP
CH3 HA
mTFP-1
CD8 α + t-20AA
Double t-20 AA
t-20AA + CD8α
CD8α + Leucine Zipper Basep1
CD8α + Leucine Zipper Acid1
Transmembrane domain

CD28
CD137 (4-1BB)
CD8α
CD3ζ

TABLE 1-continued

Regions that may be included in an anti-SLC45A2 targeting CAR

Endo-domain (signaling domain)

CD28 + CD3ζ
CD28 + CD27 + CD3ζ
CD28 + OX40 + CD3ζ
CD28 + 4-1BB + CD3ζ
CD28 + CD27 + OX40 + CD3ζ
CD28 + 4-1BB + CD27 + CD3ζ
CD28 + 4-1BB + OX40 + CD3ζ
4-1BB + CD3ζ
4-1BB + OX40 + CD3ζ
4-1BB + CD27 + CD3ζ
CD27 + CD3ζ
CD27 + OX 40 + CD3ζ
CD284 + CD3ζ
CD284 + CD27 + CD3ζ
CD284 + OX40 + CD3ζ
CD284 + 4-1BB + CD3ζ
CD284 + 4-1BB + OX40 + CD3ζ
CD284 + CD27 + OX40 + CD3ζ
CD284 + 4-1BB + CD27 + CD3ζ
4-1BB + ICOS + CD3ζ
CD28 + ICOS + CD3ζ
ICOS + CD3ζ
CD3ζ
CD28 only ζ—zeta;
Δ—mutant;
Note
4-1BB is also referred to as CD137;
"+" refers to the fusion of the different regions.

II. Soluble TCRs

In some embodiments, the present disclosure provides soluble TCRs, such as a SLC45A2 TCR provided herein. Soluble TCRs are useful, not only for the purpose of investigating specific TCR-pMHC interactions, but also potentially as a diagnostic tool to detect infection, or to detect autoimmune disease markers. Soluble TCRs also have applications in staining, for example to stain cells for the presence of a particular peptide antigen presented in the context of the MHC. Similarly, soluble TCRs can be used to deliver a therapeutic agent, for example a cytotoxic compound or an immunostimulating compound, to cells presenting a particular antigen. Soluble TCRs may also be used to inhibit T cells, for example, those reacting to an autoimmune peptide antigen.

In the context of this application, "solubility" is defined as the ability of the TCR to be purified as a mono disperse heterodimer in phosphate buffered saline (PBS) (KCL 2.7 mM, $KH_2PO_4$ 1.5 mM, NaCl 137 mM and $Na_2PO4$ 8 mM, pH 7.1-7.5. Life Technologies, Gibco BRL) at a concentration of 1 mg/ml and for more than 90% of said TCR to remain as a mono disperse heterodimer after incubation at 25° C. for 1 hour.

In some aspects, the present disclosure provides a soluble T cell receptor (sTCR), which comprises (i) all or part of a TCR α chain (e.g., SEQ ID NO: 1, 2, 11, 12, 21, 22, 31, 32, 41 or 42), except the transmembrane domain thereof, and (ii) all or part of a TCR β chain (e.g., SEQ ID NO: 6, 7, 16, 17, 26, 27, 36, 37, 46 or 47), except the transmembrane domain thereof, wherein (i) and (ii) each comprise a functional variable domain and at least a part of the constant domain of the TCR chain, and are linked by a disulfide bond between constant domain residues which is not present in native TCR.

In some aspects, the soluble TCR comprises a TCR α or γ chain extracellular domain dimerized to a TCR β or δ chain extracellular domain respectively, by means of a pair of C-terminal dimerization peptides, such as leucine zippers (International Patent Publication No. WO 99/60120; U.S. Pat. No. 7,666,604).

A soluble TCR (which is preferably human) of the present disclosure may be provided in substantially pure form, or as a purified or isolated preparation. For example, it may be provided in a form which is substantially free of other proteins.

A plurality of soluble TCRs of the present disclosure may be provided in a multivalent complex. Thus, the present disclosure provides, in one aspect, a multivalent T cell receptor (TCR) complex, which comprises a plurality of soluble T cell receptors as described herein. Each of the plurality of soluble TCRs is preferably identical.

In its simplest form, a multivalent TCR complex according to the invention comprises a multimer of two or three or four or more T cell receptor molecules associated (e.g. covalently or otherwise linked) with one another, preferably via a linker molecule. Suitable linker molecules include, but are not limited to, multivalent attachment molecules such as avidin, streptavidin, neutravidin and extravidin, each of which has four binding sites for biotin. Thus, biotinylated TCR molecules can be formed into multimers of T cell receptors having a plurality of TCR binding sites. The number of TCR molecules in the multimer will depend upon the quantity of TCR in relation to the quantity of linker molecule used to make the multimers, and also on the presence or absence of any other biotinylated molecules. Preferred multimers are dimeric, trimeric or tetrameric TCR complexes.

Suitable structures for use in the present methods include membrane structures such as liposomes and solid structures which are preferably particles such as beads, for example latex beads. Other structures which may be externally coated with T cell receptor molecules are also suitable. Preferably, the structures are coated with T cell receptor multimers rather than with individual T cell receptor molecules.

In the case of liposomes, the T cell receptor molecules or multimers thereof may be attached to or otherwise associated with the membrane. Techniques for this are well known to those skilled in the art.

A label or another moiety, such as a toxic or therapeutic moiety, may be included in a multivalent TCR complex of the present invention. For example, the label or other moiety may be included in a mixed molecule multimer. An example of such a multimeric molecule is a tetramer containing three TCR molecules and one peroxidase molecule. This may be achieved by mixing the TCR and the enzyme at a molar ratio of about 3:1 to generate tetrameric complexes, and isolating the desired complex from any complexes not containing the correct ratio of molecules. These mixed molecules may contain any combination of molecules, provided that steric hindrance does not compromise or does not significantly compromise the desired function of the molecules. The positioning of the binding sites on the streptavidin molecule is suitable for mixed tetramers since steric hindrance is not likely to occur.

The TCR (or multivalent complex thereof) of the present disclosure may alternatively or additionally be associated with (e.g. covalently or otherwise linked to) a therapeutic agent which may be, for example, a toxic moiety for use in cell killing, or an immunostimulating agent such as an interleukin or a cytokine. A multivalent TCR complex of the present invention may have enhanced binding capability for a TCR ligand compared to a non-multimeric T cell receptor heterodimer. Thus, the multivalent TCR complexes according to the invention are particularly useful for tracking or targeting cells presenting particular antigens in vitro or in vivo, and are also useful as intermediates for the production of further multivalent TCR complexes having such uses. The TCR or multivalent TCR complex may therefore be provided in a pharmaceutically acceptable formulation for use in vivo.

The present disclosure also provides a method for delivering a therapeutic agent to a target cell, which method comprises contacting potential target cells with a TCR or multivalent TCR complex in accordance with the present disclosure under conditions to allow attachment of the TCR or multivalent TCR complex to the target cell, said TCR or multivalent TCR complex being specific for the TCR ligand and having the therapeutic agent associated therewith.

In particular, the soluble TCR or multivalent TCR complex can be used to deliver therapeutic agents to the location of cells presenting a particular antigen. This would be useful in many situations and, in particular, against tumors. A therapeutic agent could be delivered such that it would exercise its effect locally but not only on the cell it binds to. Thus, one particular strategy envisages anti-tumor molecules linked to T cell receptors or multivalent TCR complexes specific for tumor antigens.

Many therapeutic agents could be employed for this use, for instance radioactive compounds, enzymes (e.g., perforin) or chemotherapeutic agents (e.g., cisplatin). To improve limiting toxic effects in the desired location the toxin may be provided inside a liposome linked to streptavidin so that the compound is released slowly. This may reduce damaging effects during the transport in the body and help to limit toxic effects until after binding of the TCR to the relevant antigen presenting cells.

Other suitable therapeutic agents include:
  small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;
  peptide cytotoxins, i.e. proteins or fragments thereof with the ability to kill mammalian cells. Examples include ricin, diphtheria toxin, pseudomonas bacterial exotoxin A, DNAase and RNAase;
  radio-nuclides, i.e. unstable isotopes of elements which decay with the concurrent emission of one or more of α or β particles, or γ rays. Examples include iodine 131, rhenium 186, indium 111, yttrium 90, bismuth 210 and 213, actinium 225 and astatine 213;
  prodrugs, such as antibody directed enzyme pro-drugs; and
  immuno-stimulants, i.e. moieties which stimulate immune response. Examples include cytokines such as IL-2, chemokines such as IL-8, platelet factor 4, melanoma growth stimulatory protein, etc, antibodies or fragments thereof such as anti-CD3 antibodies or fragments thereof, complement activators, xenogeneic protein domains, allogeneic protein domains, viral/bacterial protein domains and viral/bacterial peptides.

The soluble TCRs of the present disclosure may be used to modulate T cell activation by binding to specific TCR ligand and thereby inhibiting T cell activation. Autoimmune diseases involving T cell-mediated inflammation and/or tissue damage would be amenable to this approach, for example type I diabetes. Knowledge of the specific peptide epitope presented by the relevant pMHC is required for this use.

The use of the soluble TCRs and/or multivalent TCR complexes of the present disclosure in the preparation of a composition for the treatment of cancer or autoimmune disease is also envisaged.

Also provided is a method of treatment of cancer or autoimmune disease comprising administration to a patient in need thereof of an effective amount of the soluble TCRs and/or multivalent TCR complexes of the present invention.

As is common in anti-cancer and autoimmune therapy the sTCRs of the present disclosure may be used in combination with other agents for the treatment of cancer and autoimmune disease, and other related conditions found in similar patient groups.

III. Adoptive Cell Transfer Therapies

Provided herein are methods for treating or delaying progression of cancer in an individual comprising administering to the individual an effective amount an antigen-specific cell (e.g., autologous or allogeneic T cells (e.g., regulatory T cells, CD4+ T cells, CD8+ T cells, or gamma-delta T cells), NK cells, invariant NK cells, NKT cells, mesenchymal stem cell (MSC)s, or induced pluripotent stem (iPS) cells) therapy, such as a SLC45A2-specific cell therapy. Adoptive T cell therapies with genetically engineered TCR-transduced T cells (e.g., expressing a TCR comprising one of SEQ ID NOs: 51-70) are also provided herein. In further embodiments, methods are provided for the treatment of cancer (e.g., melanoma) comprising immunizing a subject with a purified tumor antigen or an immunodominant tumor antigen-specific peptide. In some embodiments, the adoptive cell transfer therapy is provided to a subject (e.g., a human patient) in combination with as second therapy, such as a chemotherapy, a radiotherapy, a surgery, or a second immunotherapy.

Embodiments of the present disclosure concern obtaining and administering TCR-engineered cells to a subject as an immunotherapy to target cancer cells. In particular, the TCR-engineered (e.g., autologous or allogeneic T cells (e.g., regulatory T cells, CD4+ T cells, CD8+ T cells, or gamma-delta T cells), NK cells, invariant NK cells, NKT cells, mesenchymal stem cell (MSC)s, or induced pluripotent stem (iPS) cells) cells are antigen-specific cells (e.g., SLC45A2-specific cells). Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

A. T Cell Preparation and Administration

In some embodiments, T cells are autologous. However the cells can be allogeneic. In some embodiments, the T cells are isolated from the patient, so that the cells are autologous. If the T cells are allogeneic, the T cells can be pooled from several donors. The cells are administered to the subject of interest in an amount sufficient to control, reduce, or eliminate symptoms and signs of the disease being treated.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4+ and/or CD8+ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ T cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) *Blood.* 1:72-82; Wang et al. (2012) *J Immunother.* 35(9): 689-701.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about $2\times10^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, such as from 10 days, 10.5 days, or 10.8 days to 14 days, 14.5 days, or 14.8 days.

The cultured T cells can be pooled and rapidly expanded. Rapid expansion provides an increase in the number of antigen-specific T cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T cell receptor stimulation in the presence of feeder lymphocytes and either interleukin-2 (IL-2) or interleukin-15 (IL-15), with IL-2 being preferred. The non-specific T cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T cell growth factor, such as 300 IU/ml IL-2 or IL-15, with IL-2 being preferred. The in vitro-induced T cells are rapidly expanded by re-stimulation with the same antigen(s) of the cancer pulsed onto HLA-A2-expressing antigen-presenting cells. Alternatively, the T cells can be re-stimulated with irradiated, autologous lymphocytes or with irradiated HLA-A2+ allogeneic lymphocytes and IL-2, for example.

The autologous T cells can be modified to express a T cell growth factor that promotes the growth and activation of the autologous T cells. Suitable T cell growth factors include, for example, interleukin (IL)-2, IL-7, IL-15, and IL-12. Suitable methods of modification are known in the art. See, for instance, Sambrook et al., *Molecular Cloning: A Laboratory Manual,* $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. In particular aspects, modified autologous T cells express the T cell growth factor at high levels. T cell growth factor coding sequences, such as that of IL-12, are readily available in the art, as are promoters, the operable linkage of which to a T cell growth factor coding sequence promote high-level expression.

In certain embodiments, a T cell growth factor that promotes the growth and activation of the autologous T cells is administered to the subject either concomitantly with the autologous T cells or subsequently to the autologous T cells. The T cell growth factor can be any suitable growth factor that promotes the growth and activation of the autologous T cells. Examples of suitable T cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T cell growth factor.

The T cell may be administered intravenously, intramuscularly, subcutaneously, transdermally, intraperitoneally, intrathecally, parenterally, intrathecally, intracavitary, intraventricularly, intra-arterially, or via the cerebrospinal fluid, or by any implantable or semi-implantable, permanent or degradable device. The appropriate dosage of the T cell therapy may be determined based on the type of disease to be treated, severity and course of the disease, the clinical condition of the individual, the individual's clinical history and response to the treatment, and the discretion of the attending physician.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes.

In some embodiments, naked DNA or a suitable vector encoding a CAR can be introduced into a subject's T cells (e.g., T cells obtained from a human patient with cancer or other disease). Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. In some embodiments, the use of naked DNA may reduce the time required to produce T cells expressing a CAR generated via methods of the present invention.

Alternatively, a viral vector (e.g., a retroviral vector, adenoviral vector, adeno-associated viral vector, or lentiviral vector) can be used to introduce the chimeric construct into T cells. Generally, a vector encoding a CAR that is used for transfecting a T cell from a subject should generally be non-replicating in the subject's T cells. A large number of vectors are known that are based on viruses, where the copy number of the virus maintained in the cell is low enough to maintain viability of the cell. Illustrative vectors include the pFB-neo vectors (STRATAGENE®) as well as vectors based on HIV, SV40, EBV, HSV, or BPV.

Once it is established that the transfected or transduced T cell is capable of expressing a CAR as a surface membrane protein with the desired regulation and at a desired level, it can be determined whether the chimeric receptor is functional in the host cell to provide for the desired signal induction. Subsequently, the transduced T cells may be reintroduced or administered to the subject to activate anti-tumor responses in the subject. To facilitate administration, the transduced T cells may be made into a pharmaceutical composition or made into an implant appropriate for administration in vivo, with appropriate carriers or diluents, which are preferably pharmaceutically acceptable. The means of making such a composition or an implant have been described in the art (see, for instance, Remington's Pharmaceutical Sciences, 16th Ed., Mack, ed. (1980)). Where appropriate, transduced T cells expressing a CAR can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Generally, a pharmaceutically acceptable form is preferably employed that does not ineffectuate the cells expressing the chimeric receptor. Thus, desirably the transduced T cells can be made into a pharmaceutical composition containing a balanced salt solution such as Hanks' balanced salt solution, or normal saline.

B. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, artificial antigen presenting cells (aAPCs) are useful in preparing CAR-based therapeutic compositions and cell therapy products. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009).

aAPCs may be used to expand T Cells expressing a CAR. During encounter with tumor antigen, the signals delivered to T cells by antigen-presenting cells can affect T cell programming and their subsequent therapeutic efficacy. This has stimulated efforts to develop artificial antigen-presenting cells that allow optimal control over the signals provided to T cells (Turtle et al., 2010). In addition to antibody or antigen of interest, the aAPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (also called B7 or CD80), which can bind to CD28 and/or CTLA-4 molecules on the surface of T cells, thereby affecting, e.g., T cell expansion, Th1 differentiation, short-term T cell survival, and cytokine secretion such as interleukin (IL)-2 (see Kim et al., 2004). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs) that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

C. Nucleic Acids

In an aspect, the present disclosure provides a nucleic acid encoding an isolated TCR, CAR, or soluble peptide that selectively binds SLC45A2 (e.g., at $SLC45A2_{382-390}$ or $SLC45A2_{393-402}$ immunogenic epitopes) and has at least about 90%, 91%, 92%, 93%, 94%, 95%, 96%, 97%, 98%, 99%, or 100% sequence identity to a TCR variable region disclosed herein (e.g., SEQ ID NO:1-50), or the peptide may have 1, 2, 3, or 4 point mutations (e.g., substitution mutations) as compared to SEQ ID NO:1-50. As stated above, peptide may be, e.g., from 8 to 35 amino acids in length, or any range derivable therein. In some embodiments, the tumor antigen-specific peptide corresponds to a portion of the tumor antigen protein such as SLC45A2. The term "nucleic acid" is intended to include DNA and RNA and can be either double stranded or single stranded.

Some embodiments of the present disclosure provide recombinantly-produced tumor antigen-specific peptides (e.g., a SLC45A2 peptide) which can specifically bind a HLA-A*0201. Accordingly, a nucleic acid encoding a tumor antigen-specific peptide may be operably linked to an expression vector and the peptide produced in the appropriate expression system using methods well known in the molecular biological arts. A nucleic acid encoding a tumor antigen-specific peptide disclosed herein may be incorporated into any expression vector which ensures good expression of the peptide. Possible expression vectors include but are not limited to cosmids, plasmids, or modified viruses (e.g. replication defective retroviruses, adenoviruses and adeno-associated viruses), so long as the vector is suitable for transformation of a host cell.

A recombinant expression vector being "suitable for transformation of a host cell" means that the expression vector contains a nucleic acid molecule of the invention and regulatory sequences selected on the basis of the host cells to be used for expression, which is operatively linked to the nucleic acid molecule. The terms, "operatively linked" or "operably linked" are used interchangeably, and are intended to mean that the nucleic acid is linked to regulatory sequences in a manner which allows expression of the nucleic acid.

Accordingly, the present invention provides a recombinant expression vector comprising nucleic acid encoding a tumor antigen-specific peptide, and the necessary regulatory sequences for the transcription and translation of the inserted protein-sequence. Suitable regulatory sequences may be derived from a variety of sources, including bacterial, fungal, or viral genes (e.g., see the regulatory sequences described in Goeddel (1990)).

Selection of appropriate regulatory sequences is generally dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

A recombinant expression vector may also contain a selectable marker gene which facilitates the selection of host cells transformed or transfected with a recombinant tumor antigen-specific peptides (e.g., a SLC45A2peptide) disclosed herein. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of a recombinant expression vector, and in particular, to determine the effect of a mutation on expression and phenotype. It will be appreciated that selectable markers can be introduced on a separate vector from the nucleic acid of interest Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Suitable host cells include a wide variety of prokaryotic and eukaryotic host cells. For example, the proteins of the invention may be expressed in bacterial cells such as *E. coli*, insect cells (using baculovirus), yeast cells or mammalian cells.

A nucleic acid molecule of the invention may also be chemically synthesized using standard techniques. Various methods of chemically synthesizing polydeoxy-nucleotides are known, including solid-phase synthesis which, like peptide synthesis, has been fully automated in commercially available DNA synthesizers (See e.g., U.S. Pat. Nos. 4,598, 049; 4,458,066; 4,401,796; and 4,373,071).

II. Pharmaceutical Preparations

In select embodiments, it is contemplated that a cell expressing a TCR as disclosed herein, a protein containing the variable regions of a TCR, or a DNA encoding the variable regions of a TCR of the present invention may be comprised in a vaccine composition and administered to a subject to induce a therapeutic immune response in the subject towards a cancer, such as a melanoma, that expresses SLC45A2. A therapeutic composition for pharmaceutical use in a subject may comprise a TCR composition disclosed herein, such as a soluble TCR (optionally attached to an imaging agent), and a pharmaceutically acceptable carrier.

The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington: The Science and Practice of Pharmacy, 21st edition, Pharmaceutical Press, 2011, incorporated herein by reference). Except insofar as any conventional carrier is incompatible with the active ingredient, its use in the vaccine compositions of the present invention is contemplated.

As used herein, a "protective immune response" refers to a response by the immune system of a mammalian host to a cancer. A protective immune response may provide a therapeutic effect for the treatment of a cancer, e.g., decreasing tumor size, increasing survival, etc.

A person having ordinary skill in the medical arts will appreciate that the actual dosage amount of a therapeutic composition administered to an animal or human patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

A therapeutic composition disclosed herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularly, orally, topically, locally, and by inhalation, injection, infusion, continuous infusion, lavage, and localized perfusion. A therapeutic composition may also be administered to a subject via a catheter, in cremes, in lipid compositions, by ballistic particulate delivery, or by other method or any combination of the forgoing as would be known to one of ordinary skill in the art (see, for example, Remington: The Science and Practice of Pharmacy, 21$^{st}$ Ed. Lippincott Williams and Wilkins, 2005, incorporated herein by reference).

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897, 268 and 5,075,109.

In some embodiments, the vaccine composition may be administered by microstructured transdermal or ballistic particulate delivery. Microstructures as carriers for vaccine formulation are a desirable configuration for vaccine applications and are widely known in the art (Gerstel and Place 1976 (U.S. Pat. No. 3,964,482); Ganderton and McAinsh 1974 (U.S. Pat. No. 3,814,097); U.S. Pat. Nos. 5,797,898, 5,770,219 and 5,783,208, and U.S. Patent Application 2005/ 0065463). Such a vaccine composition formulated for ballistic particulate delivery may comprise an isolated SLC45A2 peptide disclosed herein immobilized on a surface of a support substrate. In these embodiments, a support substrate can include, but is not limited to, a microcapsule, a microparticle, a microsphere, a nanocapsule, a nanoparticle, a nanosphere, or a combination thereof.

Microstructures or ballistic particles that serve as a support substrate for an TCR, such as a soluble TCR, disclosed herein may be comprised of biodegradable material and non-biodegradable material, and such support substrates may be comprised of synthetic polymers, silica, lipids, carbohydrates, proteins, lectins, ionic agents, crosslinkers, and other microstructure components available in the art. Protocols and reagents for the immobilization of a peptide of the invention to a support substrate composed of such materials are widely available commercially and in the art.

In other embodiments, a vaccine composition comprises an immobilized or encapsulated TCR or soluble TCR disclosed herein and a support substrate. In these embodiments, a support substrate can include, but is not limited to, a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides, have been reviewed (U.S. Pat. Nos. 5,567,434; 5,552,157; 5,565,213; 5,738,868 and 5,795,587, each of which is specifically incorporated in its entirety by reference).

In addition to the methods of delivery described herein, a number of alternative techniques are also contemplated for administering the disclosed vaccine compositions. By way of nonlimiting example, a vaccine composition may be administered by sonophoresis (i.e., ultrasound) which has been used and described in U.S. Pat. No. 5,656,016 for enhancing the rate and efficacy of drug permeation into and through the circulatory system; intraosseous injection (U.S. Pat. No. 5,779,708), or feedback-controlled delivery (U.S. Pat. No. 5,697,899), and each of the patents in this paragraph is specifically incorporated herein in its entirety by reference.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

A soluble TCR may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Sterile injectable solutions are prepared by incorporating the active peptides in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

A. Combination Therapies

In certain embodiments, the compositions and methods of the present embodiments involve an antigen-specific cell (e.g., autologous or allogeneic T cells (e.g., regulatory T cells, CD4+ T cells, CD8+ T cells, or gamma-delta T cells), NK cells, invariant NK cells, NKT cells, mesenchymal stem cell (MSC)s, or induced pluripotent stem (iPS) cells) population in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation.

In some embodiments, the additional therapy is a chemotherapy such as, e.g., dacarbazine, or temozolomide. The additional therapy may be one or more of the chemotherapeutic agents known in the art.

A T cell therapy may be administered before, during, after, or in various combinations relative to an additional cancer therapy, such as immune checkpoint therapy. The administrations may be in intervals ranging from concurrently to minutes to days to weeks. In embodiments where the T cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an antigen-specific T cell therapy, peptide, or TCR is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer*, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. U.S. Pat. Nos. 8,735,553, 8,354,509, and 8,008, 449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) *Proc Natl Acad Sci USA* 95(17): 10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments

Example 1

Human SLC45A2 T Cell Receptor (TCR) Cloning

Methods
Generation of T Cell Clones

TCR clones were generated by exposing cells to particular SLC45A2 peptides. SLC45A2 can be selectively expressed in melanomas, as compared to normal tissues. SLC45A2 peptides $SLC45A2_{382-390}$ and $SLC45A2_{393-402}$ are immunogenic epitopes that can selectively bind to HLA-A*0201 (HLA-A2) and HLA-A*2402 (HLA-A24), respectively, and cytotoxic T lymphocytes (CTL) proliferated using these peptides can efficiently kill a variety of melanoma cells, including multiple cutaneous melanomas, uveal melanomas, mucosal melanomas, and metastatic melanomas. The SLC45A2 peptides may display antigen specific and HLA-A*0201 or HLA A*2402-restricted responses of SLC45A2-specific CD8 T cells.

The whole length VCX3A RNA was transfected to matured dendritic cells (DC). The RNA transfected DC were co-cultured with autogenetic naïve T cell at the ratio of DC:T=1:10 in the presence of IL-21. After one week, the RNA-transfected DC were used to stimulate the T again. After two round of stimulation, the CD8+ and tetramer+ double positive T cell population were sorted and expanded with rapid expansion protocol (REP). The T cell clones were generated with limited dilution method. The high activity CTL clones were screened via tumor cells killing assay.

T Cell Receptor (TCR) Cloning and Retrovirus Expression Vector Construction

The TCR (including alpha chain and beta chain) were cloned using 5'-RACE method according to the manual of the kit. The TCR V-alpha and TCR V-beta usage were identified with IMGT/V-QUEST annotation tool. Furthermore, TCR V-beta usage was also identified with flow detection using TCR Vβ Repertoire Kit. TCR V-alpha usage was identified with PCR using a panel of special primers which are annealed to 5' terminal of different TCR V-alpha. For the TCR expression retrovirus vector construction, the forward primers were designed according the TCR V-alpha or beta usage. The reverse primers were designed according the sequence of TCR alpha or beta constant region. Expression cassettes containing the alpha- and beta-TCR chains separated by the P2A linker peptide were generated and the whole length of PCR products were cloned in to retrovirus vector pMSGV1. The cloned DNA sequences were verified with sequencing.

Retrovirus Generation and Infect Human Peripheral Blood Lymphocytes (PBL)

The pMSGV1 vector containing the TCR and the envelope vector RD114 were cotransfected to the package cell line GP2-293. After transfection for 6-8 hours, the medium were refreshed. The supernatant were harvested 24 hours later and was added to the 6 well plate which has been coated with 20 mg/mL RetroNectin followed by centrifugation (2000×g) at 32° C. for 2 hours. The supernatant was removed then and the PBL which were activated with 50 ng/ml OKT3 and 300 U/ml IL-2 for two days were added to the retrovirus loaded plate followed by centrifugation (1000×g) at 32° C. for 10 min. Cells were then incubated overnight at 32° C., and the procedure was repeated the following day (total of two transductions). After that, the cells were expanded at 37° C. in a 5% CO2 incubator and split as necessary.

TCR Engineered T Cell Clone Generation

After infection, the CD8+ and tetramer+ T cell population were sorted and T cell clones were generated with limited dilution method. The high activity CTL clone were screened via tumor cells killing assay. The high tumor killing activity T cell clone were further expanded with REP.

IFN-γ Release Assay

IFN-γ release from T cell was detected with ELISA method. The T cells were incubated with target cells at 10:1 ration in 96 well plate with 0.2 ml medium at 37° C. After co-culturing overnight, the supernatant was harvested and the IFN-γ concentration was detected using ELISA according to the manual of the kit.

Intracellular Cytokine Staining (ICS) Assay

The T cells were incubated with target cells at 10:1 ration in the presence of brefeldin A (BFA) at 37° C. overnight. After co-culturing, the T cells were harvested and washed. The cells were stained with flow antibody anti surface marker first. After that, the cells were washed and fixed with Fix Buffer and then were permeabilized using Permeabilizing Solution. Permeabilized cells are then stained with intracellular cytokine flow antibody. Finally, the level of cytokine producing in the cells was analyzed using FACS.

Peptide-MHC Tetramer Staining

SLC45A2-specific CD8 T cells were confirmed by staining with tetramer of $SLC45A2_{382-390}$ peptide/MHC complex for HLA A*0201 or $SLC45A2_{393-402}$ peptide/MHC complex for HLA A*2402. CD8 T cells were incubated with PE-conjugated tetramer for 20 mins, washed and then stained with APC-conjugated CD8 antibody for 15 mins in room temperature. After washing, cells were analyzed by flow cytometry (LSRFortessa X-20 Analyzer). Tetramers of HLA-A*A0201 and HLA-A*A2402 containing $SLSC45A2_{382-390}$ $SLC45A2_{393-402}$ respectively were purchased form Fred Hutchinson Cancer Research Center.

$^{51}$Chromium Release Assay

The killing ability of the TCR engineered T cell or CTL clone to lyse HLA-A2 tumor targets was measured using a standard $^{51}$Cr release assay. Tumor cells or normal cells were labeled for 2 h at 37° C. with 200 μCi of $^{51}$Cr, and after three times washing, the labeled targets plated triplicated well at a 2000 targets per well. Labeled target cells were washed and then incubated with effector cells at the different ratios for 4 h at 37° C. in 0.2 ml of complete medium. Harvested supernatants were counted using automatic gamma counter. Maximal and spontaneous $^{51}$Cr release was determined by incubating the labeled target cells in either trypan lysis buffer or medium for 4 h at 37° C. Each data point was determined as an average of quadruplicate wells. The percent specific lysis was calculated as follows: % killing=((specific release−spontaneous release)/(total release−spontaneous release))×100.

Results: The TCR sequences of several SLC45A2 CD8 T cell clones were determined. The CDR3 sequences of these TCR clones, including β3, β22, #24, #39, and #76, are shown in Table 2. T cells were transfected with each of these TCR clones and the cytotoxic activity was assessed by Chromium release assay using Mel526 (HLA A2$^+$) and Mel888 (HLA A2$^-$) cells and was compared to the activity of the parental T cell clones. TCR-transfected T cells were observed to lyse the HLA-A24-matched target, Mel888, but not the HLA-A24 mismatched target, Mel526, for all clones (FIGS. 2A-B, FIGS. 4A-B, and FIGS. 6A-B). The parental T cells showed similar cytotoxicity.

SLC45A2 tetramer and CD8 staining was also performed on all of the TCR clones and parental cells. Activated autologous PBMCs were transduced with retrovirus including the TCR gene. After 8 days, the T cells were stained with SLC45A2-PE conjugated tetramers. The SLC45A2 tetramer-positive T cells were sorted and subjected to REP (FIGS. 3A-B, 5A-B, and 7A-B).

TABLE 2

SLC45A2 TCR gene information.

| Clone Name | α gene | α-CDR3 | β gene | β-CDR3 |
|---|---|---|---|---|
| SLC45A2 HLA A24 | | | | |
| β3 | TRAV14/ DV4*01F TRAJ48*01F | CAMREGWG FGNEKLTF (SEQ ID NO: 35) | TRBV28*01F TRBJ2-3*01F TRBD2*01F TRBC2 | CASREKRG EDTDTQYF (SEQ ID NO: 40) |
| β22 | TRAV24*01F TRAJ39*01F | CAFDSYYN AGNMLTF (SEQ ID NO: 45) | TRBV2*01F TRBJ1-1*01F TRBD1*01F | CASSADTG TLNTEAFF (SEQ ID NO: 50) |
| SLC45A2 HLA A2 | | | | |
| #24 | TRAV24*01F TRAJ31*01F | AFLSNNN ARLM (SEQ ID NO: 5) | TRBV13*01F TRBJ1-6*02F TRBD1*01F TRBC1 | CASSLWGS HNSPL (SEQ ID NO: 10) |
| #39 | TRAV17*01F TRAJ39*01F | CATDDNAG NMLTF (SEQ ID NO: 15) | TRBV28*01F TRBJ2-3*01F TRBD-N/A TRBC2 | CASSFTPD TQYF (SEQ ID NO: 20) |
| #76 | TRAV21*01F TRAJ36*01F | CADNQTGA NNLFF (SEQ ID NO: 25) | TRBV13*01F TRBJ1-2*01F TRBD2*01F | CASSEGGY GNYGYTF (SEQ ID NO: 30) |

Example 2

Functionality of Human SLC45A2 T Cell Receptor (TCR) Clone #39

Tetramer Staining Detection of TCR Engineered T Cells.

Figure 8:
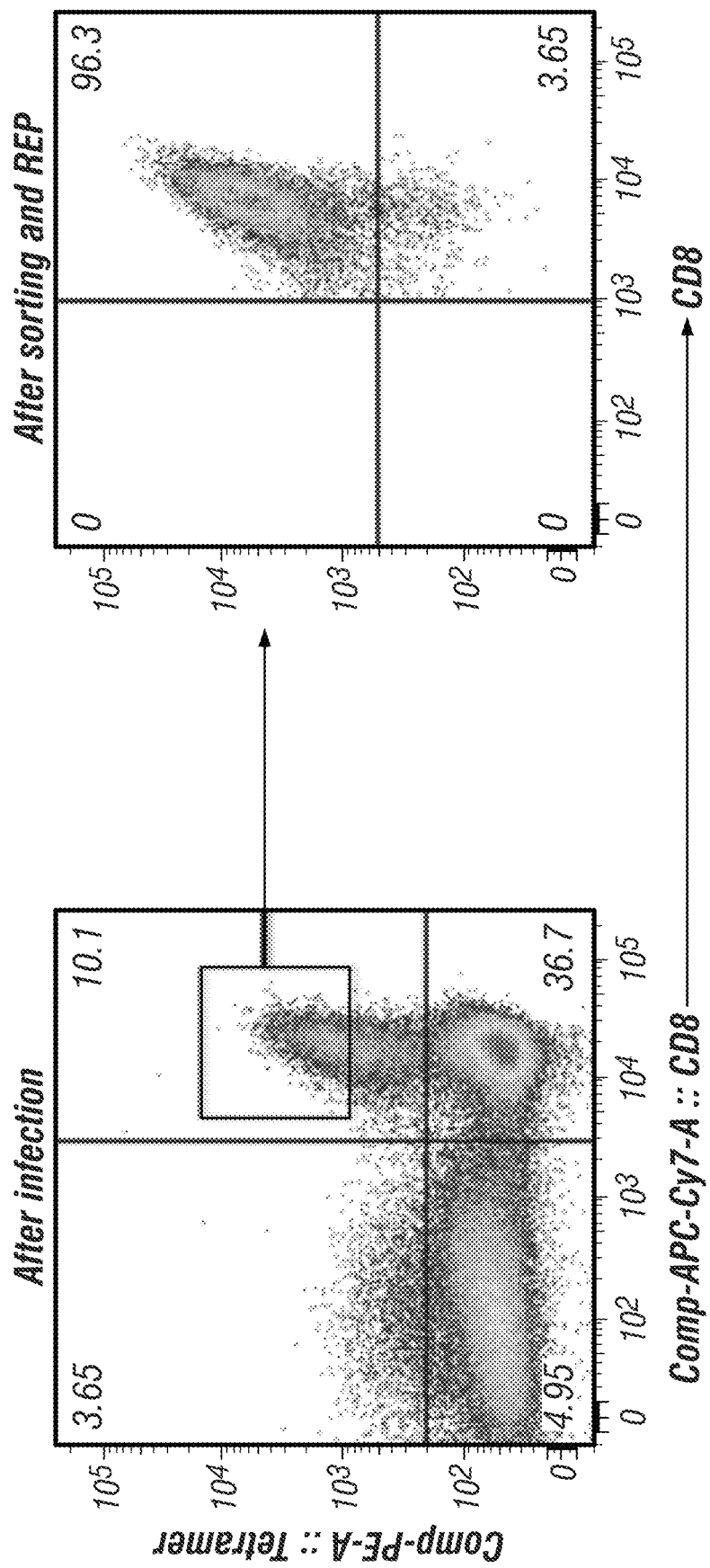
FIG. 8: Tetramer staining detection of TCR engineered T cells. The TCR from SLC45A2 CTL (#39 clone) was cloned into the retroviral expression vector pMSGV1 and recombinant retrovirus was generated for the infection of PBMC. After infection, a Tetramer+ population appeared for both CD8+ and CD4+ T cells. The CD8+Tetramer+ and CD4+ Tetramer+ populations were sorted and expanded with rapid expansion protocol (REP), after which they were tested for purity.
Figure 8:
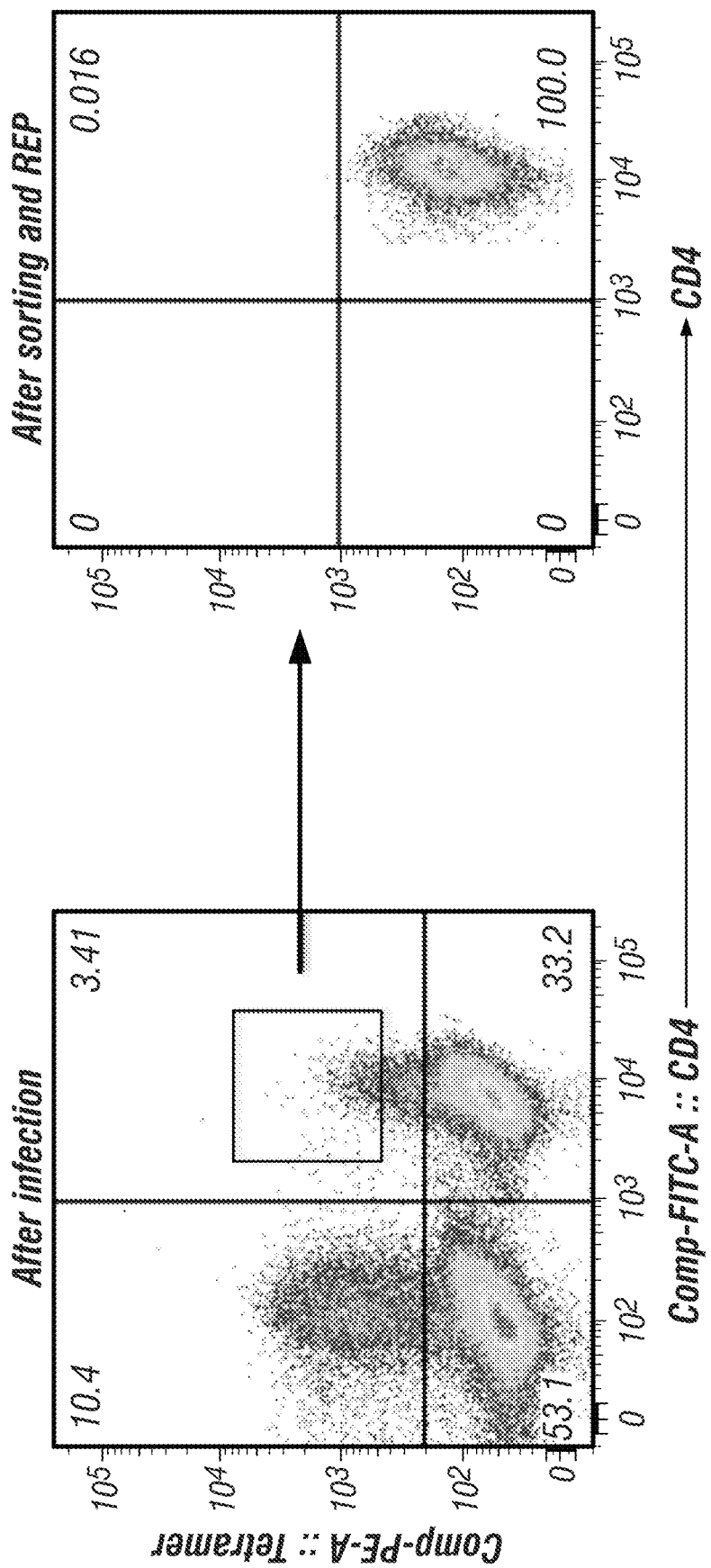

The TCR from SLC45A2 CTL (#39 clone) was cloned into the retroviral expression vector pMSGV1 and recombinant retrovirus was generated for the infection of PBMC. After infection, a Tetramer+ population appeared for both CD8+ and CD4+ T cells. The CD8+Tetramer+ and CD4+ Tetramer+ populations were sorted and expanded with rapid expansion protocol (REP). After expansion, the purity of CD8+Tetramer+ population reached 96% (FIG. 8). However, the Tetramer+ population of CD4+ T cells was lost after REP (FIG. 8).

Peptide Binding Titration Assay for TCR Engineered T Cells.

Figure 9:
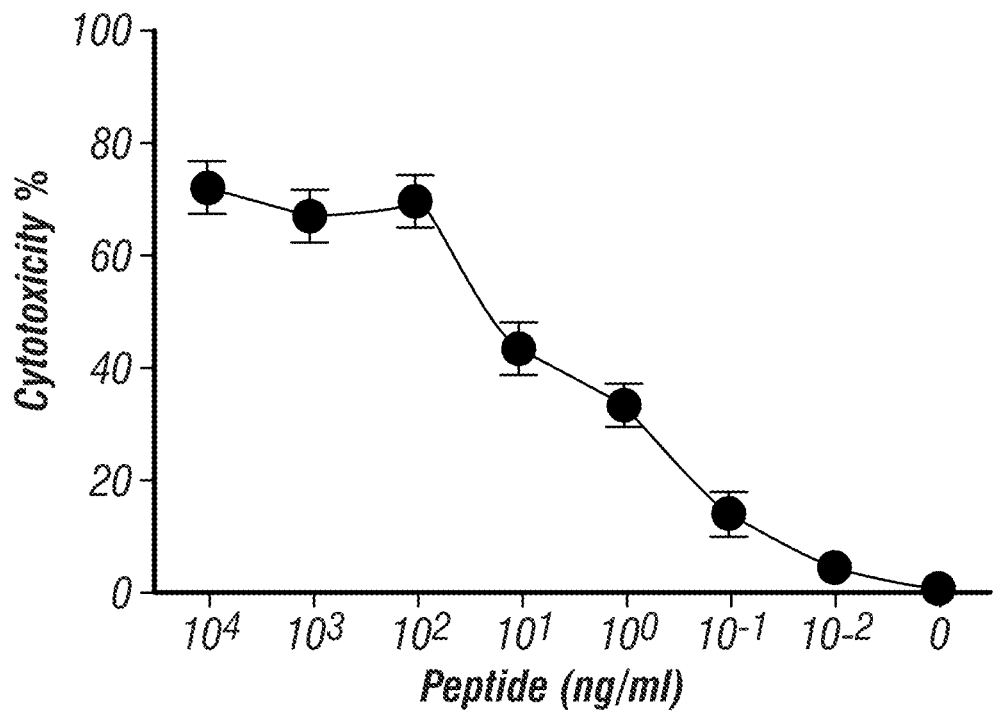
FIG. 9: Peptide binding titration assay for TCR engineered T cells. T2 cells were pulsed with different concentrations of SLC45A2 peptide (from 10 pg/mL to 10 μg/mL) and labeled with $^{51}$Cr. CD8+ or CD4+ TCR engineered T cells were used as effector cells and co-cultured with T2 cells (E:T=20:1). The $^{51}$Cr release was detected after four hours of co-culturing.
Figure 9:
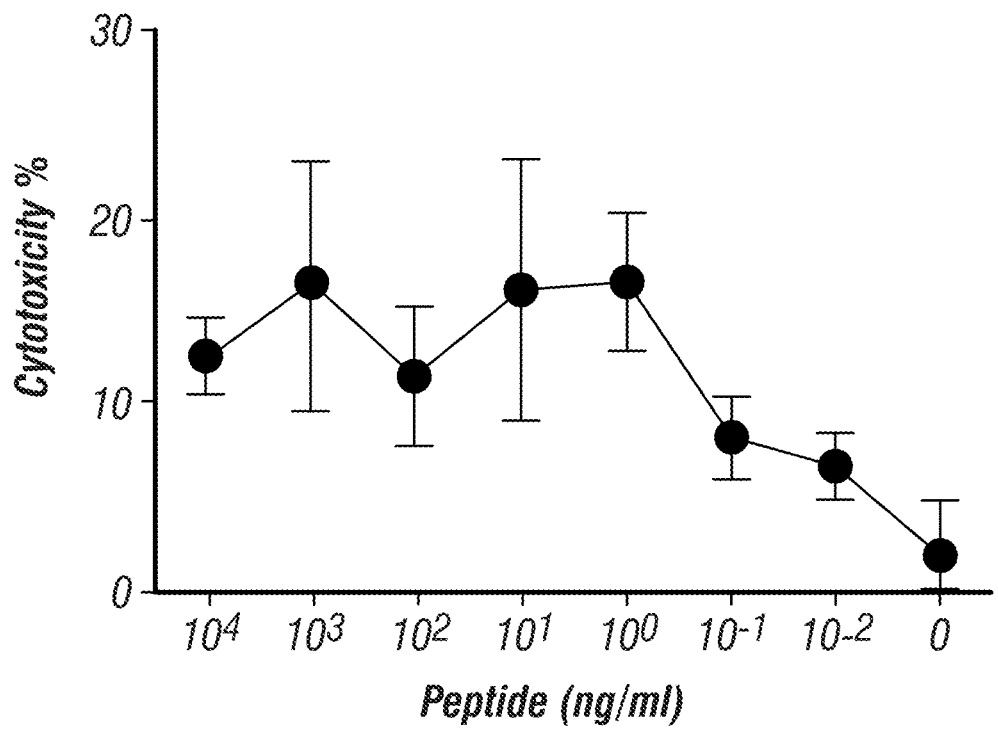

T2 cells were pulsed with different concentrations of SLC45A2 peptide (from 10 pg/mL to 10 μg/mL) and labeled with $^{51}$Cr. CD8+ or CD4+ TCR engineered T cells were used as effector cells and co-cultured with T2 cells. The $^{51}$Cr release was detected after four hours of co-culturing. The CD8+ TCR engineered T cells showed high affinity but CD4+ TCR engineered T cells did not (FIG. 9).

Endogenously Presented Epitope Recognition of CD8+ TCR Engineered T Cell.

Figure 10:
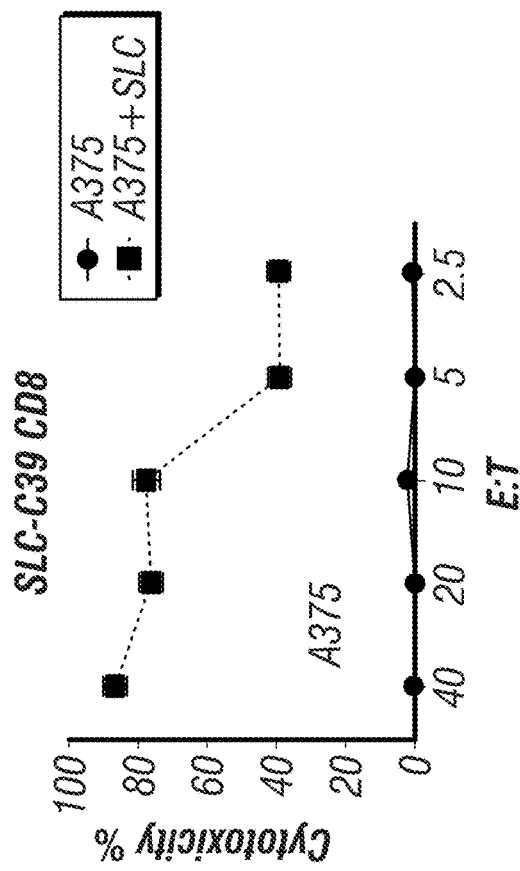
FIG. 10: Endogenously presented epitope recognition of CD8+ TCR engineered T cell. CD8+ TCR engineered T cells were able to kill the Mel526 (HLA-A2+, SLC45A2+) and Mel888-A2 (HLA-A2 forced expression, SLC45A2+) tumor cells lines, but not the A375 (HLA-A2+, SLC45A2-) or Mel624 (HLA-A2+, SLC45A2+) tumor cell lines (FIG. 10). However, T cells were able to kill A375 cells pulsed with SLC45A2 peptide.
Figure 10:
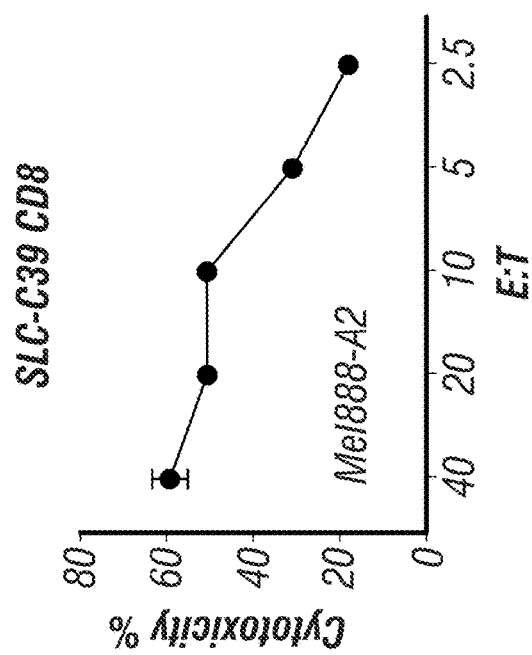
Figure 10:
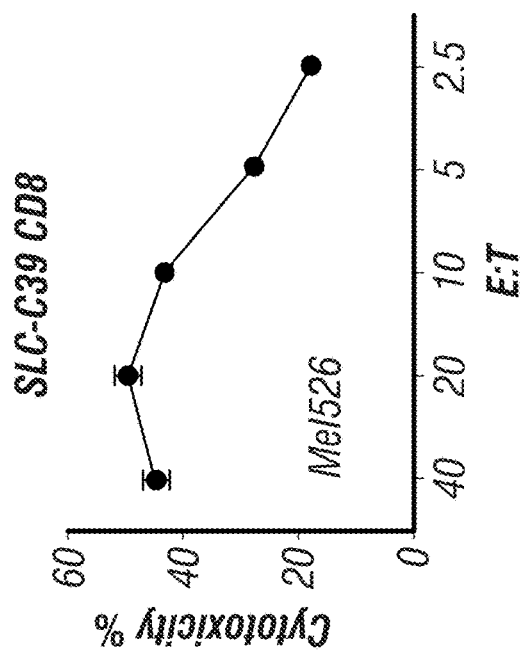
Figure 10:
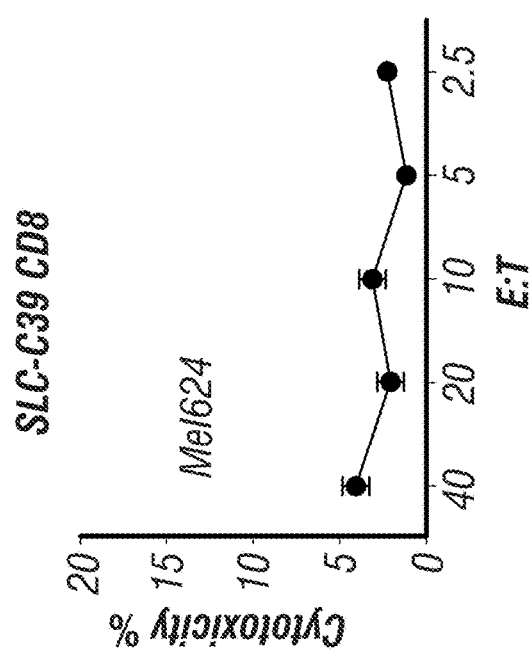

CD8+ TCR engineered T cells were able to kill the Mel526 (HLA-A2+, SLC45A2+) and Mel888-A2 (HLA-A2 forced expression, SLC45A2+) tumor cells lines, but not the A375 (HLA-A2+, SLC45A2-) or Mel624 (HLA-A2+, SLC45A2+) tumor cell lines (FIG. 10). However, T cells were able to kill A375 cells pulsed with SLC45A2 peptide, indicating that Mel526 and Mel888-A2 naturally present the endogenous epitope and the TCR-engineered T cells can recognize it. Mel624 might present low levels of epitope on the surface of the cells even though it expresses SLC45A2.

Endogenously Presented Epitope Recognition of CD4+ TCR Engineered T Cell.

Figure 11:
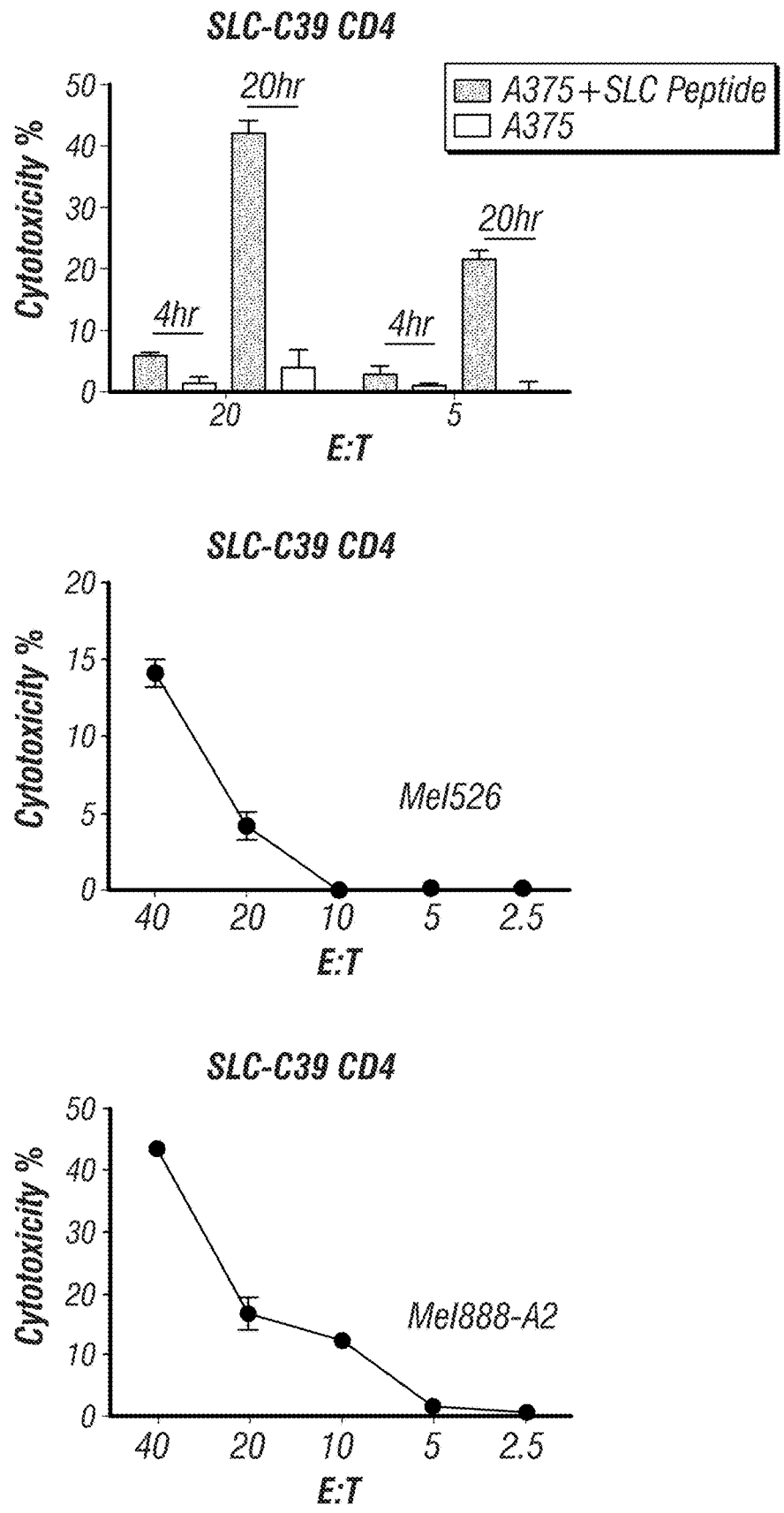
FIG. 11: Endogenously presented epitope recognition of CD4+ TCR engineered T cell. Although CD4+ TCR engineered T cells did not obviously produce a Tetramer+ population after REP, they still killed the tumor cells after long term co-culture (20 h).

Although CD4+ TCR engineered T cells did not obviously produce a Tetramer+ population after REP, they still killed the tumor cells after long term co-culture (20 h) (FIG. 11). Thus, they can recognize endogenous presented epitope at low level.

Figure 12A:
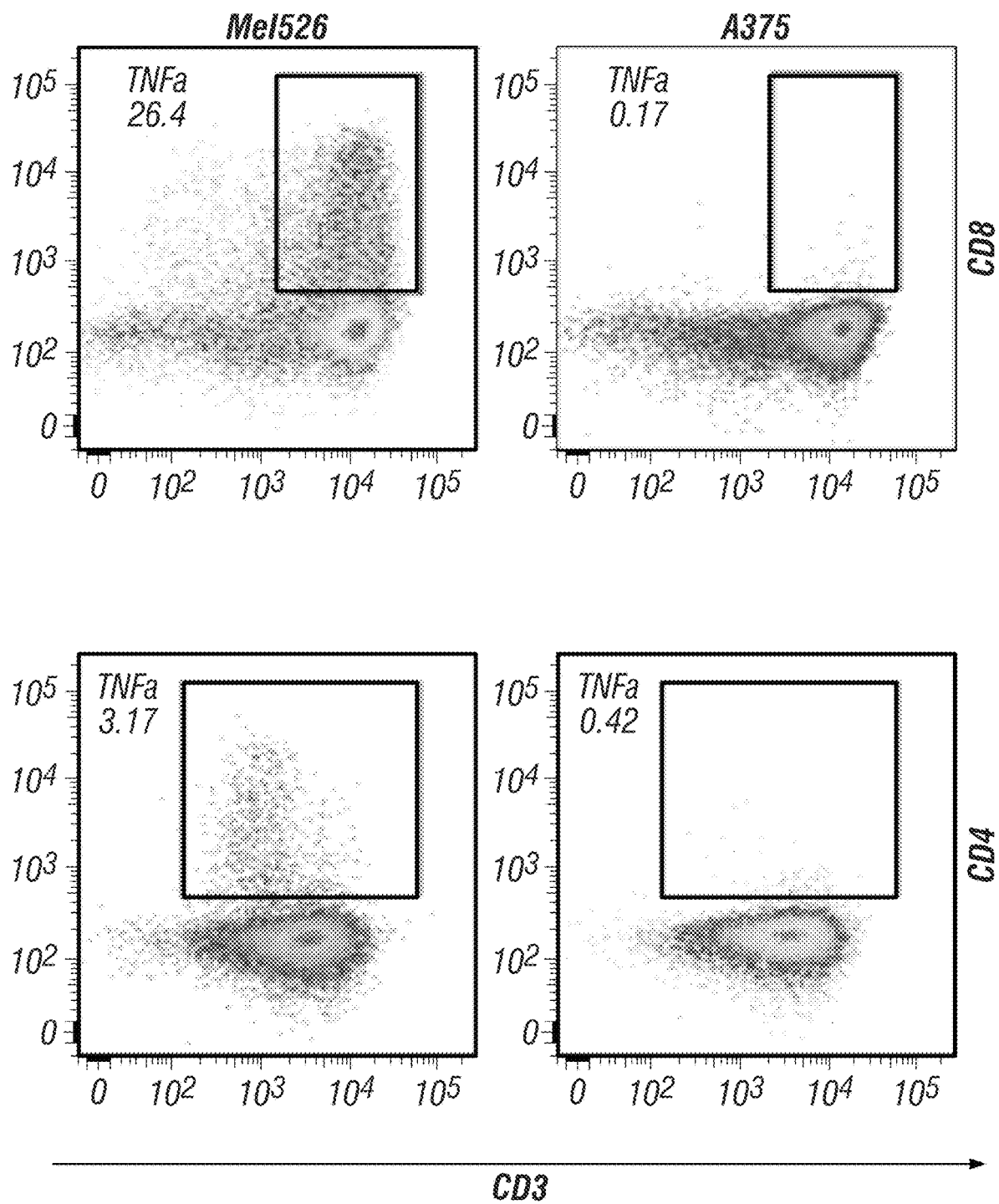
FIGS. 12A-E: TCR engineered T cells specifically respond when encountering target cells. Internal cytokine staining (ICS) assay were performed to detect the specific response of TCR engineered T cells when they encounter target cells. Mel526 (naturally present endogenous epitope of SLC45A2), A375 (negative for SLC45A2), T2 pulsed with SLC45A2 peptide, and T2 pulsed with M26 peptide (negative control) were co-cultured with TCR engineered T cells (CD8+ or CD4+, E:T=10:1). After overnight incubation, TNF-α (FIG. 12A), CD107a (FIG. 12B), IFN-γ (FIG. 12C), CD137 (FIG. 12D), and IL-2 (FIG. 12E) expression levels were detected with ICS.
Figure 12A:
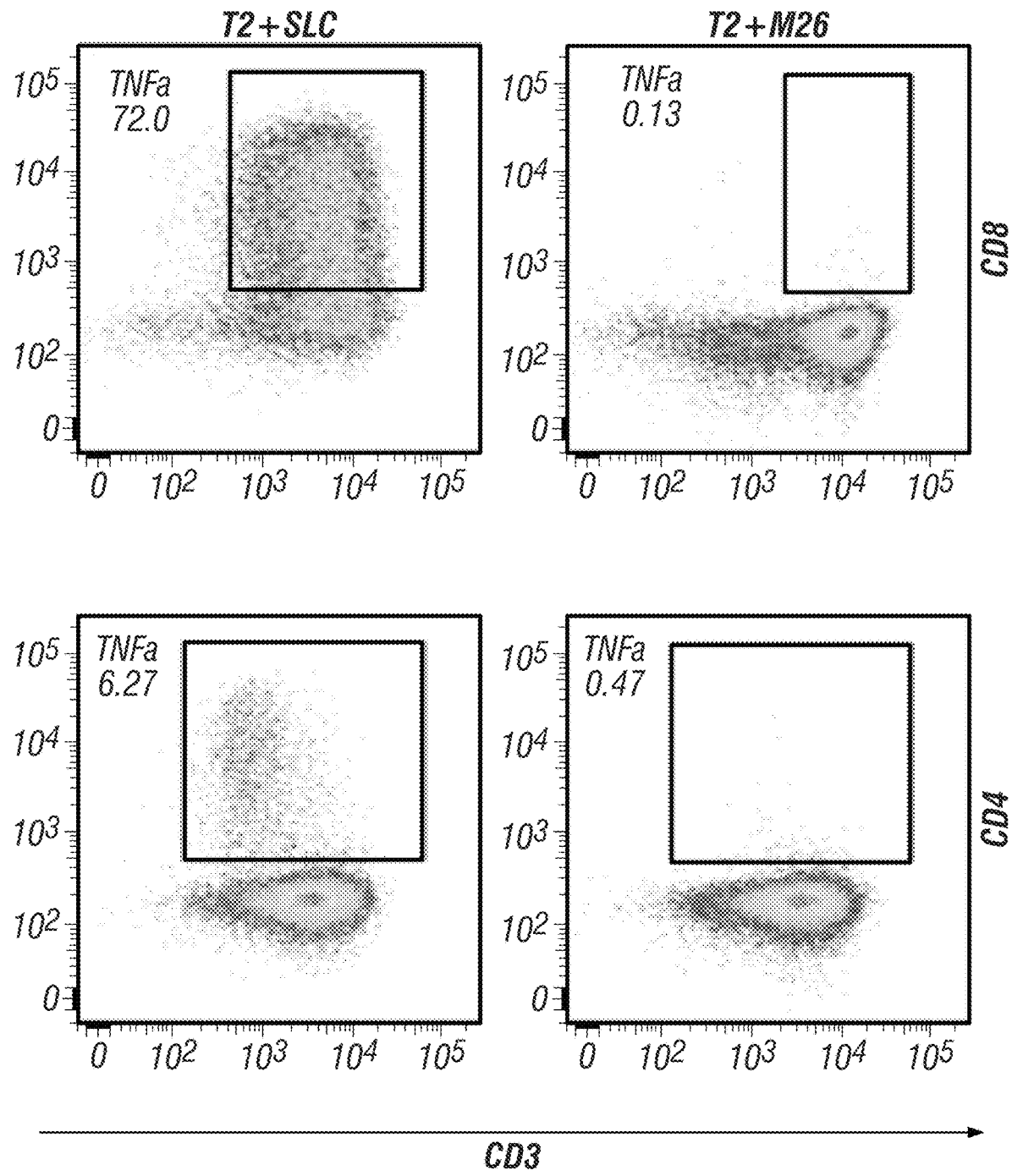
Figure 12B:
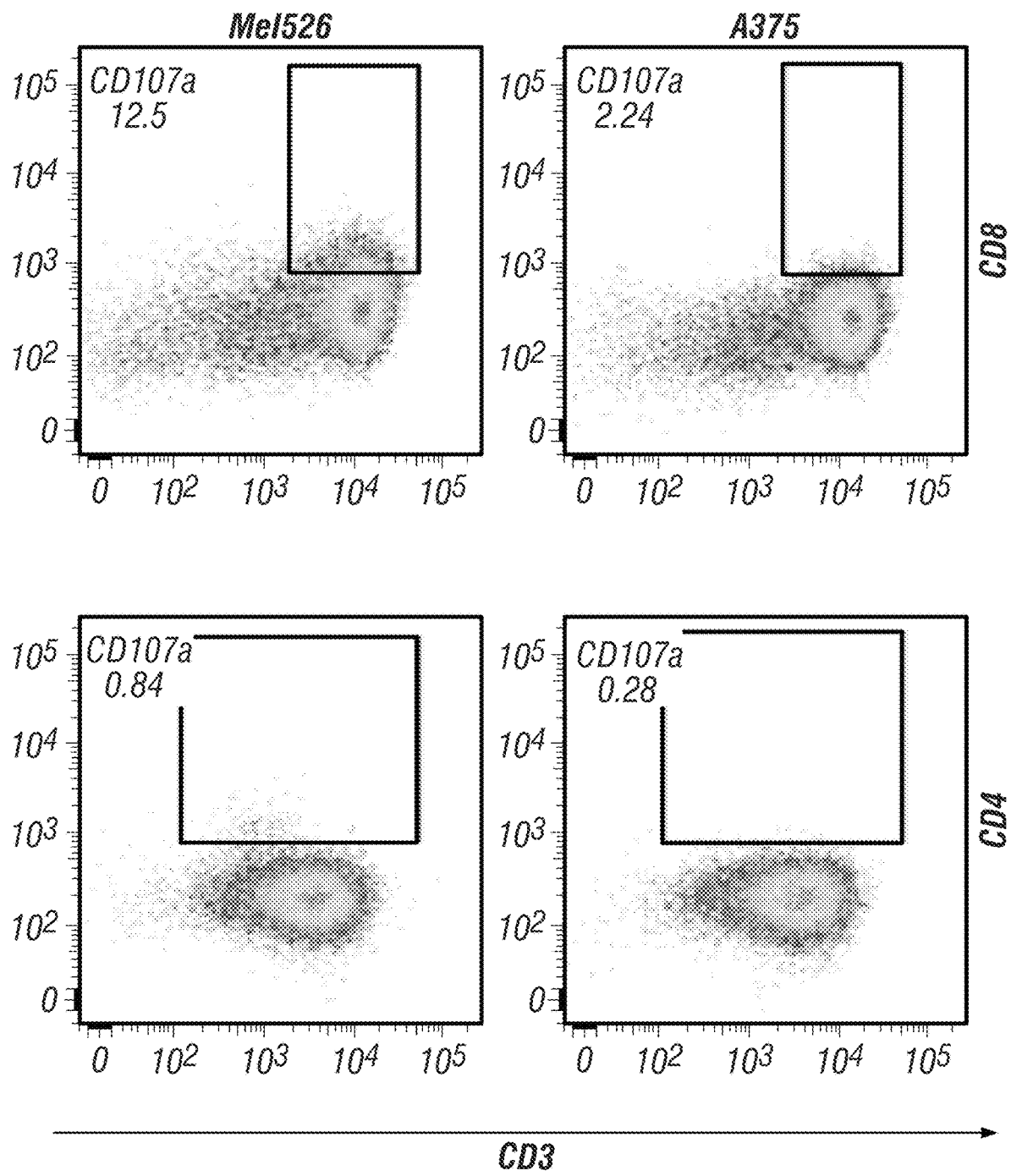
Figure 12B:
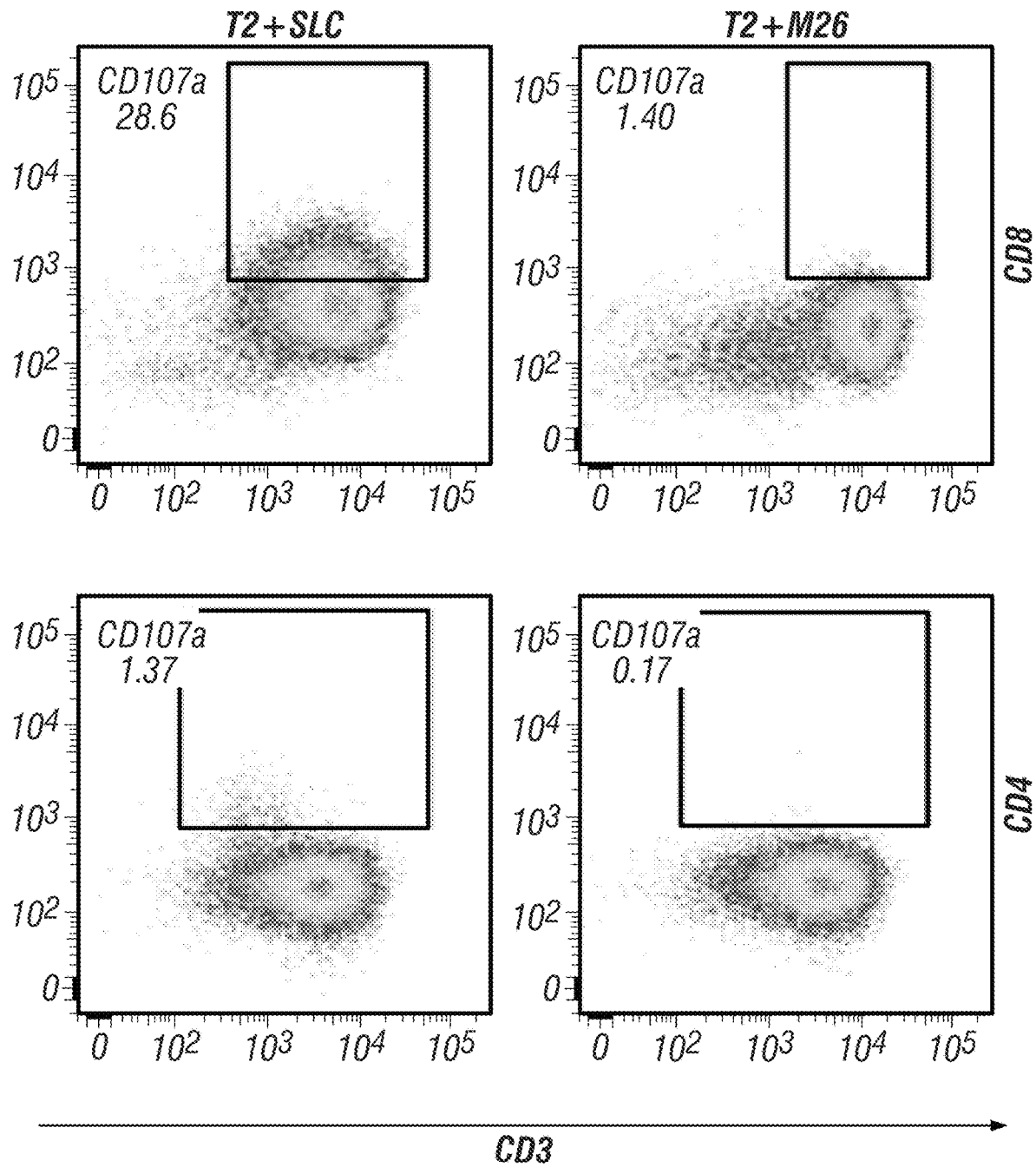
Figure 12C:
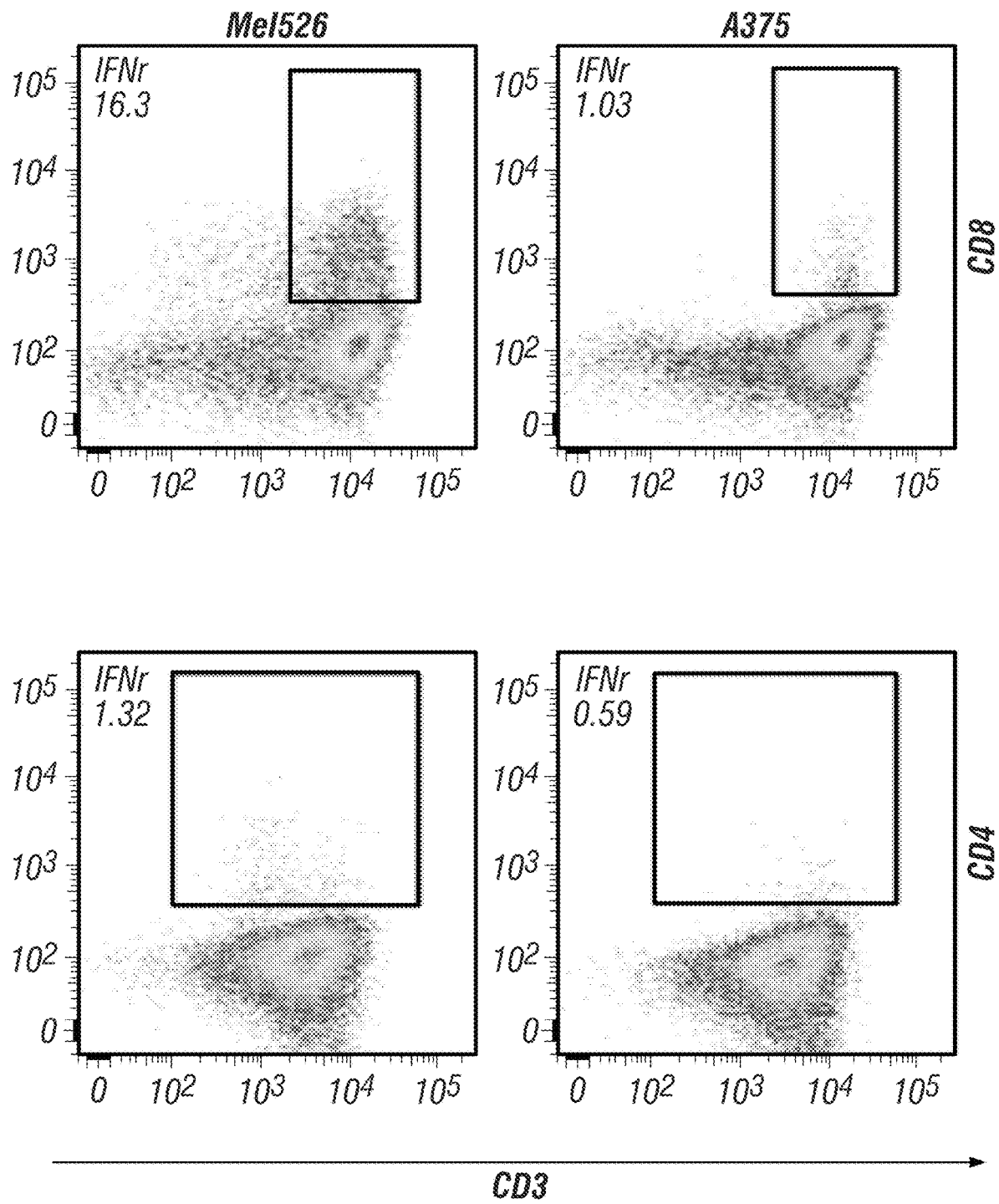
Figure 12C:
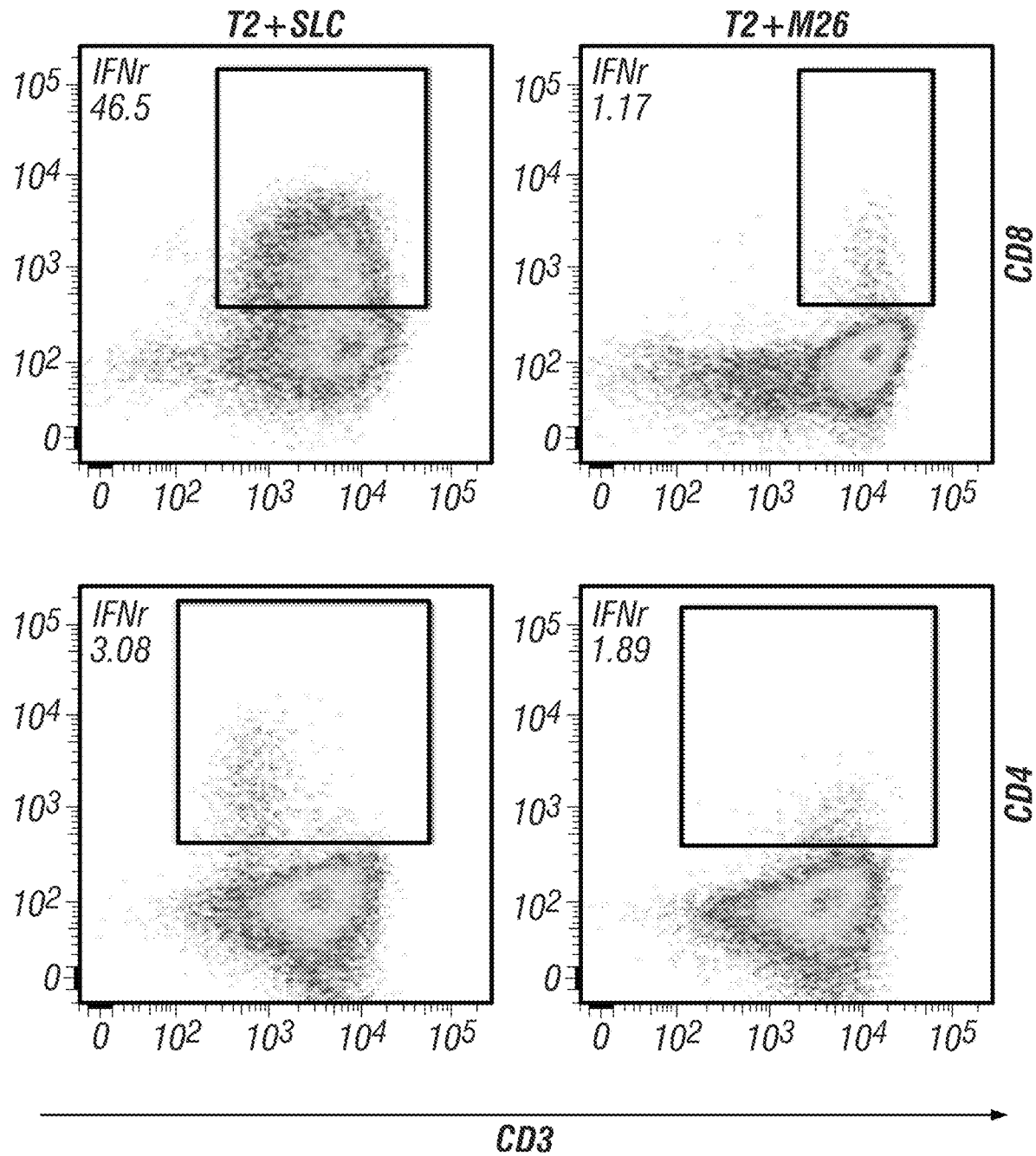
Figure 12D:
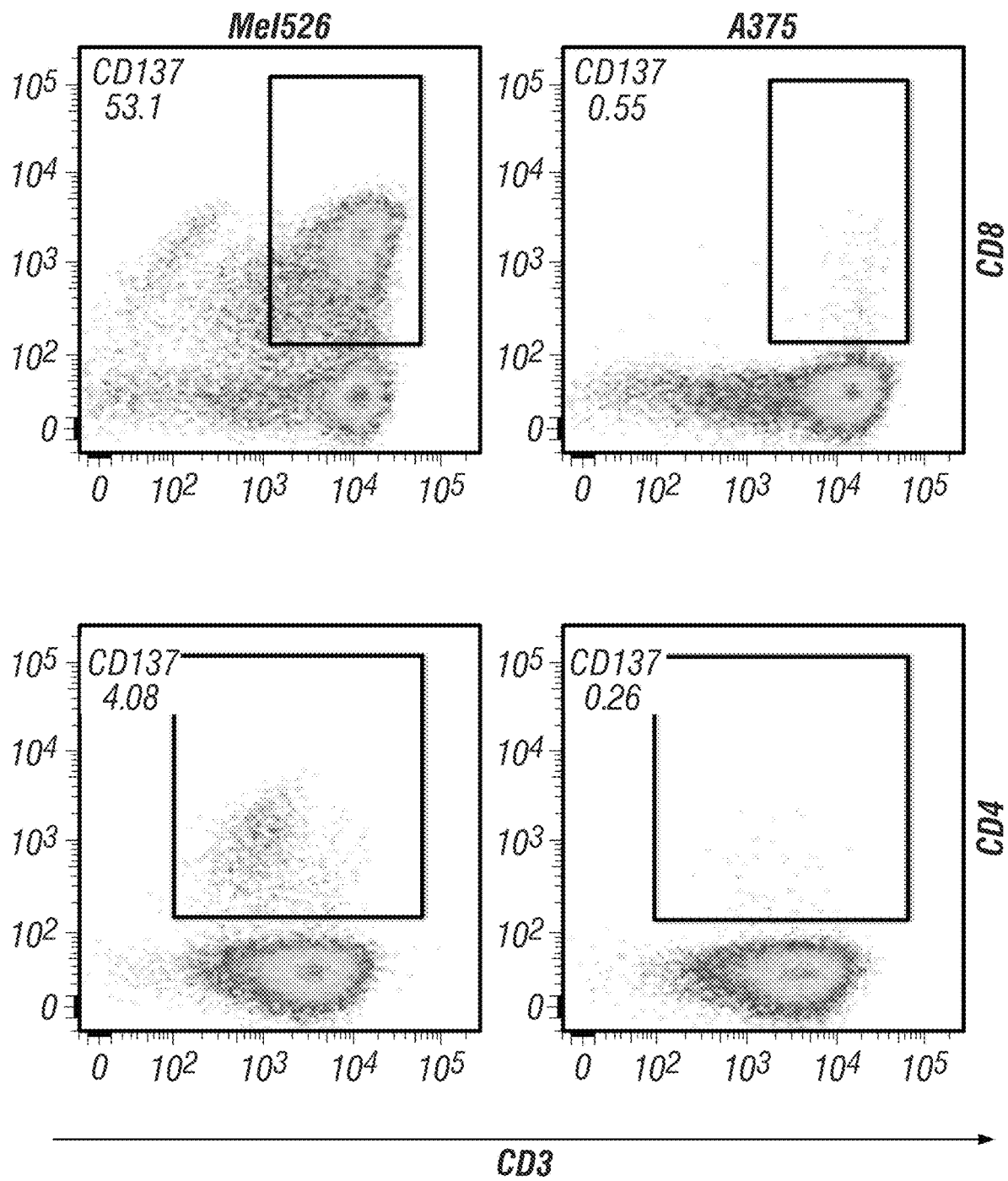
Figure 12D:
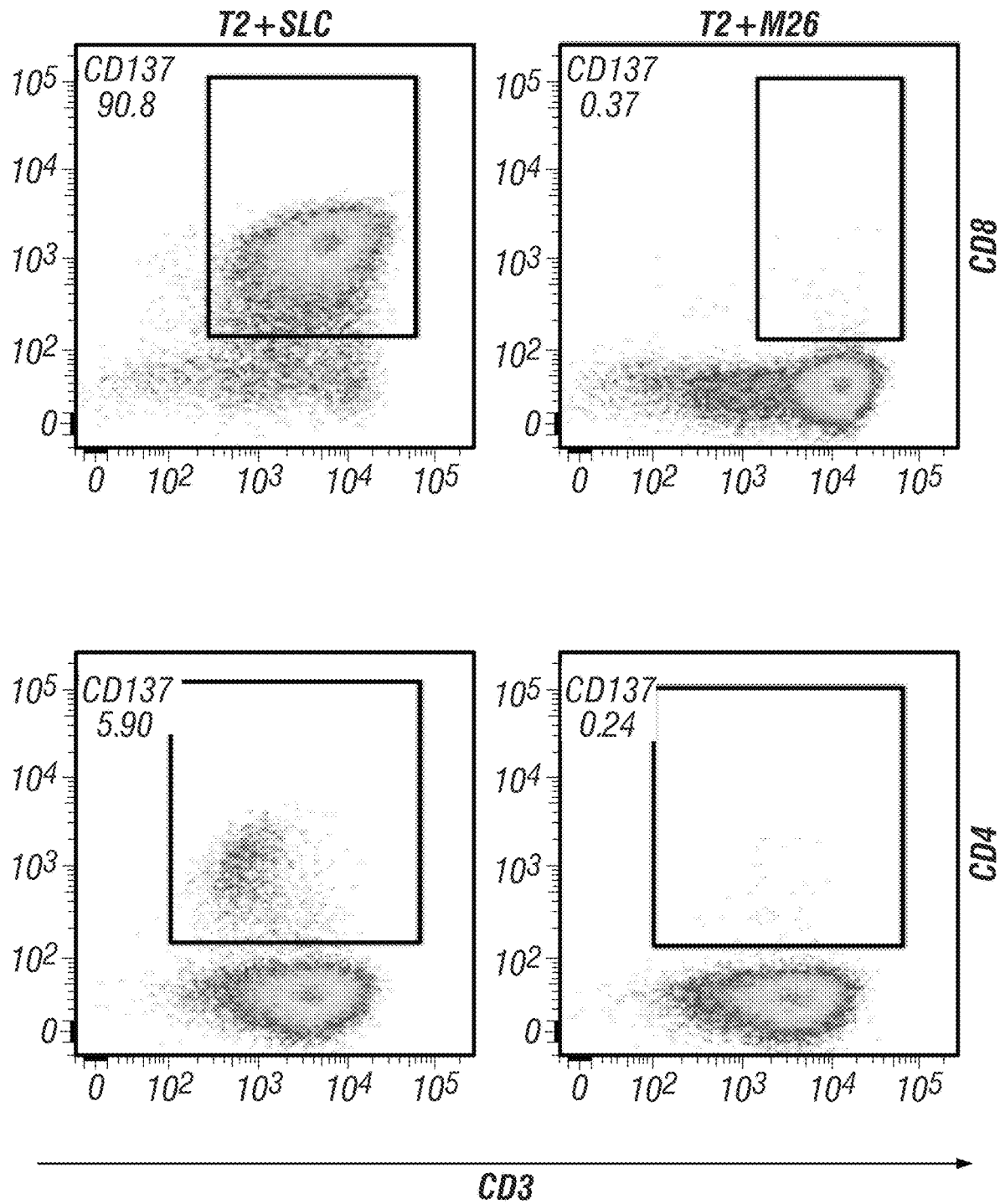
Figure 12E:
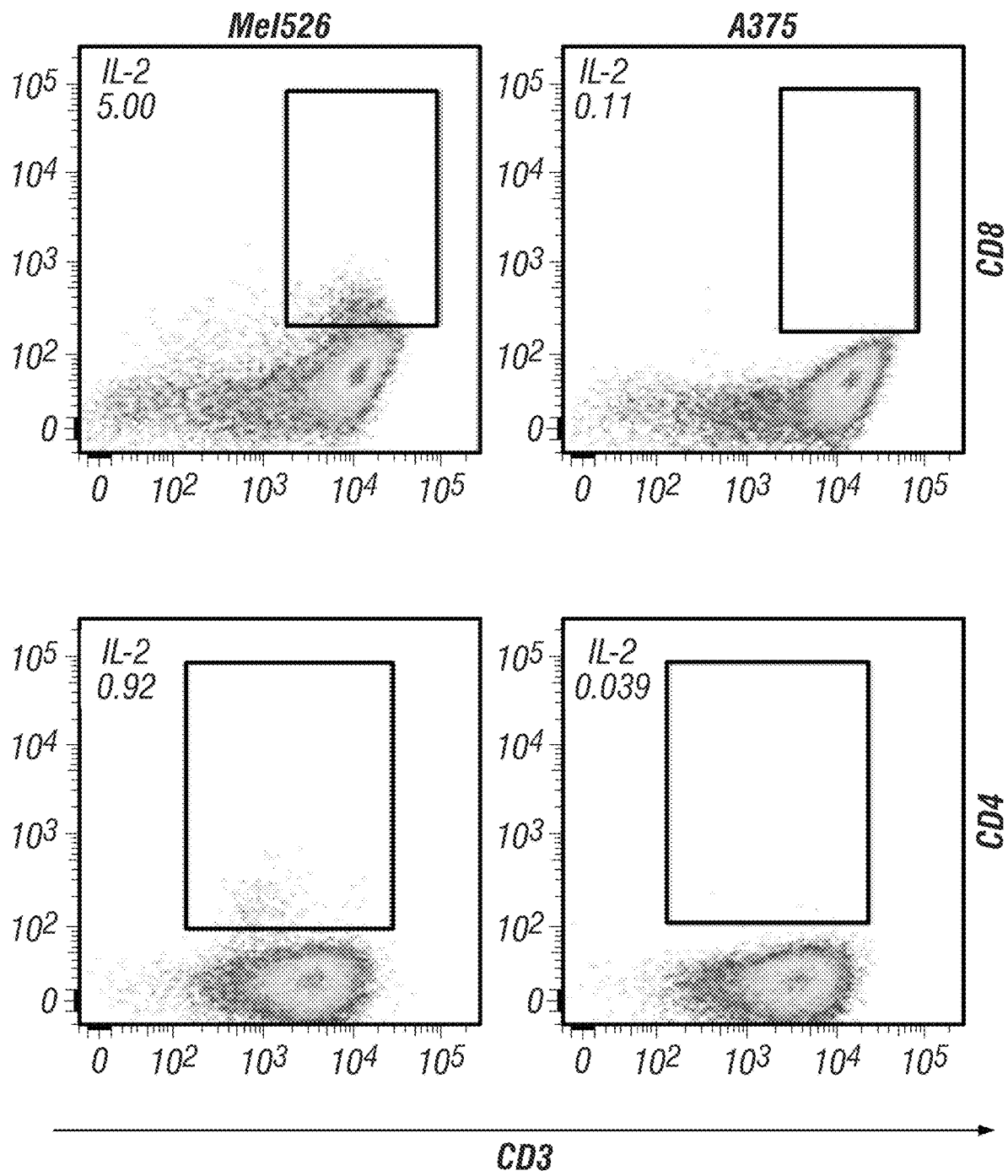
Figure 12E:
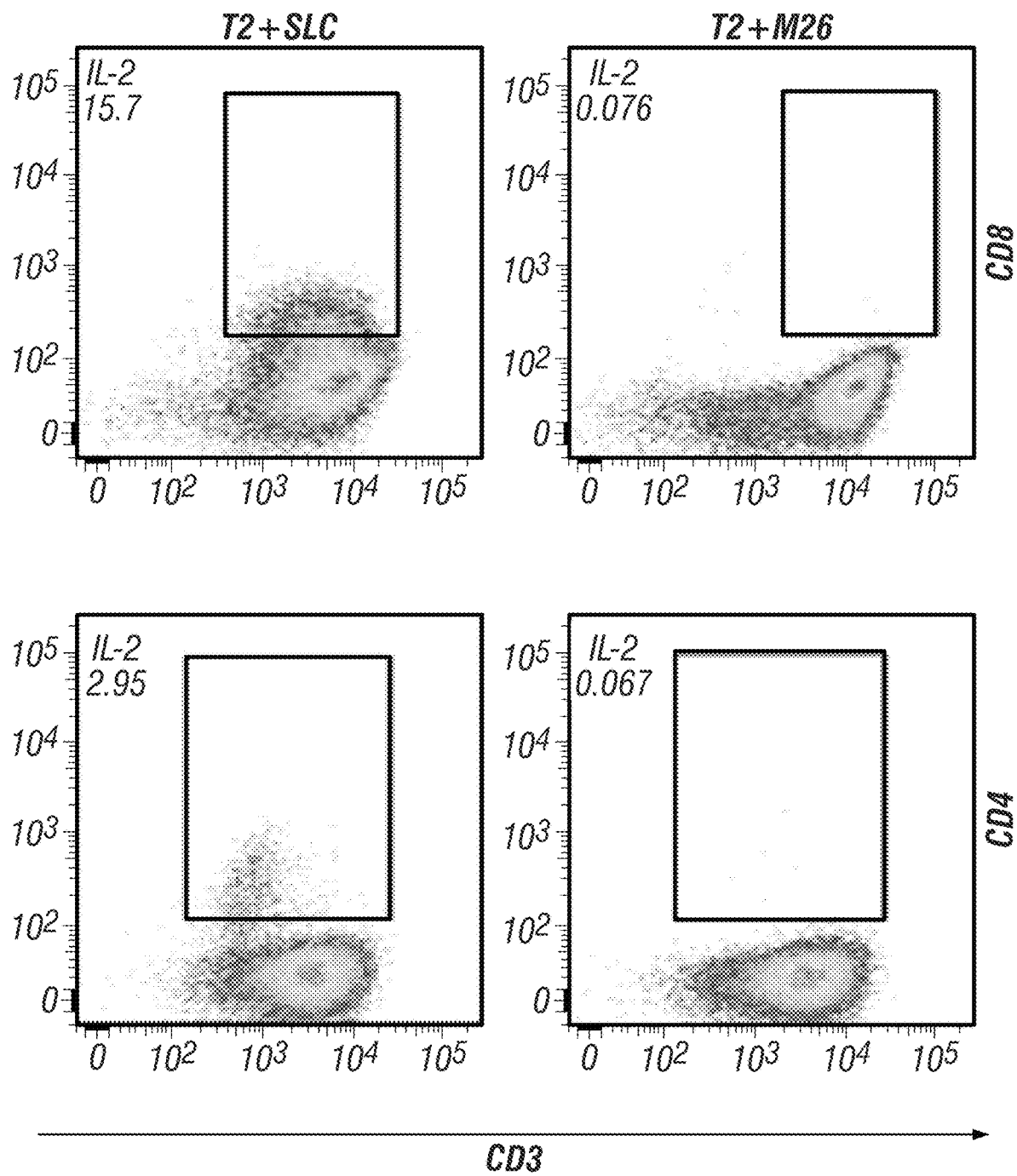

TCR engineered T cells specifically respond when encountering target cells. Internal cytokine staining (ICS) assay were performed to detect the specific response of TCR engineered T cells when they encounter target cells. Mel526 (naturally present endogenous epitope of SLC45A2), A375 (negative for SLC45A2), T2 pulsed with SLC45A2 peptide, and T2 pulsed with M26 peptide (negative control) were co-cultured with TCR engineered T cells (CD8+ or CD4+, E:T=10:1). After overnight incubation, TNF-α (FIG. 12A), CD107a (FIG. 12B), IFN-γ (FIG. 12C), CD137 (FIG. 12D), and IL-2 (FIG. 12E) expression levels were detected with ICS. Both CD8+ and CD4+ TCR engineered T cells express significantly higher levels of TNF-α, CD107a, IFN-γ, CD137, and IL-2 when they are co-cultured with Mel526 and T2 pulsed with SLC45A2 peptide, compared with A375 and T2 pulsed with M26 peptide, indicating that the TCR engineered T cells are functional and show the specific response when they encountered the target cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,814,097
U.S. Pat. No. 3,817,837
U.S. Pat. No. 3,850,752
U.S. Pat. No. 3,939,350
U.S. Pat. No. 3,964,482
U.S. Pat. No. 3,996,345
U.S. Pat. No. 4,196,265

U.S. Pat. No. 4,275,149
U.S. Pat. No. 4,277,437
U.S. Pat. No. 4,366,241
U.S. Pat. No. 4,373,071
U.S. Pat. No. 4,401,796
U.S. Pat. No. 4,458,066
U.S. Pat. No. 4,472,509
U.S. Pat. No. 4,598,049
U.S. Pat. No. 4,897,268
U.S. Pat. No. 4,938,948
U.S. Pat. No. 5,021,236
U.S. Pat. No. 5,075,109
U.S. Pat. No. 5,196,066
U.S. Pat. No. 5,262,357
U.S. Pat. No. 5,505,928
U.S. Pat. No. 5,552,157
U.S. Pat. No. 5,565,213
U.S. Pat. No. 5,567,434
U.S. Pat. No. 5,656,016
U.S. Pat. No. 5,690,807
U.S. Pat. No. 5,697,899
U.S. Pat. No. 5,738,868
U.S. Pat. No. 5,741,516
U.S. Pat. No. 5,741,957
U.S. Pat. No. 5,750,172
U.S. Pat. No. 5,756,687
U.S. Pat. No. 5,770,219
U.S. Pat. No. 5,770,219
U.S. Pat. No. 5,779,708
U.S. Pat. No. 5,783,208
U.S. Pat. No. 5,795,587
U.S. Pat. No. 5,797,898
U.S. Pat. No. 5,827,690
U.S. Pat. No. 5,990,479
U.S. Pat. No. 6,048,616
U.S. Pat. No. 6,091,001
U.S. Pat. No. 6,274,323
U.S. Pat. No. 6,630,307
U.S. Pat. No. 7,910,109
U.S. Patent Appln. 2005/0065463
Aggarwal et al., *Mod. Pathol.*, 22:206-215, 2008.
Altman et al. *Science* 274(5284):94-6, 1996.
Antibodies: A Laboratory Manual, Cold Spring Harbor Laboratory, 1988.
Atherton et al., *Biol. of Reproduction*, 32, 155-171, 1985.
Baird et al., *Scand. J Immunol.*, 60(4):363-71, 2004.
Baraldo et al., *Infect. Immun.*, 73(9):5835-41, 2005.
Bendandi et al., *Nat. Med.*, 5:1171-1177, 1999.
Berberian et al., *Science*, 261:1588-1591, 1993.
Bertinetti et al., *Cancer Res.*, 66:4496-4502, 2006.
Bijker et al., *J. Immunol.*, 179:5033-5040, 2007.
Blanchard and Shastri, *Curr. Opin. Immunol.*, 20:82-88, 2008.
Burrows et al., *Trends Immunol.*, 27:11-16, 2006.
Campbell, In: *Monoclonal Antibody Technology, Laboratory Tech. Biochem. Molec. Biol.*, Vol. 13, Burden and Von Knippenberg (Eds.), 75-83, Amsterdam, Elsevier, 1984.
Celluzzi et al., *J. Exp. Med.*, 183 283-287, 1996.
Cheson and Leonard, *N. Eng. J. Med.*, 359:613-626, 2008.
Cleary et al., *J. Biol. Chem.*, 269(29):18747-9, 1994.
Coiffier et al., *N. Eng. J Med.*, 346:235-242, 2002.
Collins et al., *Nature*, 371:626-629, 1994.
Cumber et al., *J. Immunol.*, 149B:120-126, 1992.
De Jager et al., *Semin. Nucl. Med.* 23(2), 165-179, 1993.
Dholakia et al., *J. Biol. Chem.*, 264, 20638-20642, 1989.
Di Nicola et al., *Blood*, 113:18-27, 2009.
Doolittle and Ben-Zeev, *Methods Mol. Biol.*, 109, 215-237, 1999.
Drin et al., *AAPS Pharm. Sci.*, 4(4):E26, 2002.
Du et al., *J. Pept. Res.*, 51:235-243, 1998.
Dudley et al., *J. Immunol.*, 26(4):332-342, 2003.
Elliott and O'Hare, *Cell*, 88:23-233, 1997.
European Patent 0 216 846
European Patent 0 256 055
European Patent 0 323 997
European Patent Appl. 89303964.4
Frankel and Pabo, *Cell*, 55:189-1193, 1988.
Gefter et al., *Somatic Cell Genet.*, 3:231-236, 1977.
Goding, In: *Monoclonal Antibodies: Principles and Practice*, 2d ed., Orlando, Fla., Academic Press, 60-61, 65-66, 71-74, 1986.
Goeddel, *Methods Enzymol.*, 185:3-7, 1990.
Gritti et al., *Blood*, 92:368-373, 1998.
Gulbis and Galand, *Hum. Pathol.* 24(12), 1271-1285, 1993.
Guo et al., *Nature*, 360:364-366, 1992.
Gupta et al., *Biomaterials*, 26:3995-4021, 2005.
Hawkins et al., *Hum. Gene Ther.*, 21(6):665-72, 2010.
Herling et al., *Am. J. Surg. Pathol.*, 31:1123-1129, 2007.
Herling et al., *Blood*, 114(21):4675-4686, 2009.
Hida et al., *Cancer Immunol. Immunotherapy*, 51:219-228, 2002.
Houot and Levy, *Blood Rev.*, 23:137-142, 2009.
Hoyer et al., *J. Immunol.*, 175:864-873, 2005.
Hoyer et al., *Proc. Natl. Acad. Sci. USA*, 99:14392-14397, 2002.
Inoges et al., *J. Natl. Cancer Inst.*, 98:1292-1301, 2006.
Irvine et al., *Nature*, 419:845-849, 2002.
Kang et al., *Blood*, 105:1288-1294, 2005.
Kang et al., *Science*, 240:1034-1036, 1988.
Khatoon et al., *Ann. of Neurology*, 26, 210-219, 1989.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Kohler et al., *Methods Enzymol.*, 178:3, 1989.
Kreier et al., In: *Infection, Resistance and Immunity*, Harper and Row, New York, 1991.
Kwak et al., *N. Eng. J. Med.*, 327:1209-1215, 1992.
Laine et al., *Molec. Cell*, 6:395-407, 2000.
Lee et al., *J. Immunol. Methods*, 331:13-26, 2008.
Lenert et al., *Science*, 248:1639-1643, 1990.
Lin et al., *Immunol. Cell Biol.*, 86:353-362, 2008.
Lin et al., *J. Biol. Chem.*, 270:4255-14258, 1995.
Liu et al., *Cell Mol. Biol.*, 49(2):209-216, 2003.
Malyguine et al., *J. Transl. Med.*, 2:9, 2004.
Marcus et al., *Blood*, 105:1417-1423, 2005.
Maus et al., *Nat. Biotech.*, 20:143-148, 2002.
McKee et al., *J Transl Med.* 3:35, 2005.
McLaughlin et al., *J. Clin. Oncol.*, 16:2825-2833, 1998.
Melief and van der Burg, *Nat. Rev. Cancer*, 8:351-360, 2008.
Moorthy et al., *PLoS Med.*, 1(2):e33, 2004.
Nakamura et al., In: *Enzyme Immunoassays: Heterogeneous and Homogeneous Systems*, Chapter 27, 1987.
Narducci et al., *Cancer Res.*, 57:5452-5456, 1997b.
Narducci et al., *Cancer Res.*, 60:2095-2100, 2000.
Narducci et al., *Oncogene*, 15:919-926, 1997a.
Narducci et al., *Proc. Natl. Acad. Sci. USA*, 99:11712-11717, 2002.
Navarrete et al., *Blood*, 117:1483-1491, 2011.
Neelapu et al., *Nat. Med.*, 11:986-991, 2005.
Neelapu et al., *Blood*, 15:109(12):5160-5163, 2007.
Nestle et al., *Nat. Med.*, 4:328, 1998.
O'Shannessy et al., *J. Immun. Meth.*, 99, 153-161, 1987.
Owens and Haley, *J. Biol. Chem.*, 259, 14843-14848, 1987.

Pack et al., *Biochem.*, 31:1579-1584, 1992.
Park and Neelapu, *Br. J. Haemat*, 142:179-191, 2008.
PCT Publn. WO 99/26299
Pekarsky et al., *Proc. Natl. Acad. Sci. USA*, 105:19643-19648, 2008.
Pollack, S. M., R. L. Jones, E. A. Farrar, S. R. Riddell, and C. Yee. 2014. Tetramer Guided Cell Sorter Assisted Production of Clinical Grade Autologous NY-ESO-1 Specific CD8+ T Cells. Journal of Immunotherapy of Cancer in press.
Popescu et al. *Blood*, 15:109(12):5407-5410, 2007.
Potter and Haley, *Meth. Enzymol.*, 91, 613-633, 1983.
Quintarelli et al., *Blood*, 117:3353-3362, 2011.
Ramuz et al., *Int. J Oncol.*, 26:151-157, 2005.
Remington, In: *The Science and Practice of Pharmacy*, 21st Ed., Lippincott Williams and Wilkins, 2005.
Remington, In: *The Science and Practice of Pharmacy*, 21st Ed., Pharmaceutical Press, 2011.
Ribas et al., *Trends Immunol.*, 24:58-61, 2003.
Riddell et al., *J. Immunol.*, 128(2):189-201, 1990.
Rojas et al., *J. Biol. Chem.*, 271:27456-27461, 1996.
Rojas et al., *Proc. West. Pharmacol. Soc.*, 41:55-56, 1998.
Said et al., *Lab. Invest.* 81:555-564, 2001.
Samino et al., *J. Biol. Chem.*, 281:6358-6365, 2006.
Sasso et al., *J. Immunol.*, 142:2778-2783, 1989.
Seaman B J, et al. Audiovestibular dysfunction associated with adoptive cell immunotherapy for melanoma. Otolaryngology—head and neck surgery; *Otolagngol Head Neck Surg* May 17, 2012.
Schuster et al., *J. Clin. Oncol.*, 29(20):2787-94, 2011.
Schwarze et al., *Trends in Cell Biol.*, 10:290-295, 2000.
Schwenzer et al., *J. Biol. Chem.*, 274:19368-19374, 1999.
Shorki et al., *J. Immunol.*, 146:936-940, 1991.
Silvermann et al., *J. Clin. Invest.*, 96:417-426, 1995.
Skull and Kemp, *Arch. Dis. Child.*, 74:527-530, 1996.
Stryhn et al., *Eur. J. Immunol.*, 30:3089-3099, 2000.
Teitell, *Nat. Rev. Cancer*, 5:640-648, 2005.
Timmerman et al., *Blood*, 99:1517-1526, 2002.
Virgilio et al., *Proc. Natl. Acad. Sci. USA*, 95:3885-3889, 1998.
Wakim et al., *Nature*, 471:629-632, 2011.
Wang and Wang, *Nat. Biotechnol.*, 20:149-154, 2002.
Yee et al., *J. Immunol. Methods*, 261(1-2):1-20, 2002.
Yee, C., et al., Adoptive T cell therapy using antigen-specific CD8+ T cell clones for the treatment of patients with metastatic melanoma: in vivo persistence, migration, and antitumor effect of transferred T cells. Proc Natl Acad Sci USA 99: 16168-16173, 2002b.
Yee et al. The use of endogenous T cells for adoptive transfer. *Immunological reviews* 257: 250-263. 2014.
Young et al., *J. Exp. Med.*, 183:11, 1996.
Zwaveling et al., *J. Immunol.*, 169:350-358, 2002.

What is claimed is:

1. An engineered T cell receptor (TCR) comprising
   (a) an alpha chain comprising a CDR1 having the amino acid of SEQ ID NO:3, a CDR2 having the amino acid sequence of SEQ ID NO:4, and a CDR3 having the amino acid sequence of SEQ ID NO: 5, and a beta chain comprising a CDR1 having the amino acid sequence of SEQ ID NO:8, a CDR2 having the amino acid sequence of SEQ ID NO:9, and a CDR3 having the amino acid sequence of SEQ ID NO:10;
   (b) an alpha chain comprising a CDR1 having the amino acid sequence of SEQ ID NO:13, a CDR2 having the amino acid sequence of SEQ ID NO:14, and a CDR3 having the amino acid sequence of SEQ ID NO:15, and a beta chain comprising a CDR1 having the amino acid sequence of SEQ ID NO:18, a CDR2 having the amino acid sequence of SEQ ID NO:19, and a CDR3 having the amino acid sequence of SEQ ID NO:20;
   (c) an alpha chain comprising a CDR1 having the amino acid sequence of SEQ ID NO:23, a CDR2 having the amino acid sequence of SEQ ID NO:24, and a CDR3 having the amino acid sequence of SEQ ID NO:25, and a beta chain comprising a CDR1 having the amino acid sequence of SEQ ID NO:28, a CDR2 having the amino acid sequence of SEQ ID NO:29, and a CDR3 having the amino acid sequence of SEQ ID NO:30;
   (d) an alpha chain comprising a CDR1 having the amino acid sequence of SEQ ID NO:33, a CDR2 having the amino acid sequence of SEQ ID NO:34, and a CDR3 having the amino acid sequence of SEQ ID NO:35, and a beta chain comprising a CDR1 having the amino acid sequence of SEQ ID NO:38, a CDR2 having the amino acid sequence of SEQ ID NO:39, and a CDR3 having the amino acid sequence of SEQ ID NO:40; or
   (e) an alpha chain comprising a CDR1 having the amino acid sequence of SEQ ID NO:43, a CDR2 having the amino acid sequence of SEQ ID NO:44, and a CDR3 having the amino acid sequence of SEQ ID NO:45, and a beta chain comprising a CDR1 having the amino acid sequence of SEQ ID NO:48, a CDR2 having the amino acid sequence of SEQ ID NO:49, and a CDR3 having the amino acid sequence of SEQ ID NO:50.

2. The TCR of claim 1, wherein the engineered TCR binds HLA-A2.

3. The TCR of claim 2, wherein the engineered TCR binds HLA-A*0201.

4. The TCR of claim 1, wherein the engineered TCR binds HLA-A24.

5. The TCR of claim 4, wherein the engineered TCR binds HLA-A*2402.

6. The TCR of claim 1, wherein the TCR comprises:
(a) for claim 1 (a), an alpha chain having at least 90%, 95%, or 99% identity to the amino acid sequence of SEQ ID NO: 2 and a beta chain having at least 90%, 95%, or 99% identity to the amino acid sequence of SEQ ID NO: 7;
(b) for claim 1 (b), an alpha chain having at least 90%, 95%, or 99% identity to the amino acid sequence of SEQ ID NO: 12 and a beta chain having at least 90%, 95%, or 99% identity to the amino acid sequence of SEQ ID NO:17;
(c) for claim 1 (c), an alpha chain having at least 90%, 95%, or 99% identity to the amino acid sequence of SEQ ID NO:22 and a beta chain having at least 90%, 95%, or 99% identity to the amino acid sequence of SEQ ID NO:27;
(d) for claim 1 (d), an alpha chain having at least 90%, 95%, or 99% identity to the amino acid sequence of SEQ ID NO:32 and a beta chain having at least 90%, 95%, or 99% identity to the amino acid sequence of SEQ ID NO:37; or (e) for claim 1 (e), an alpha chain having at least 90%, 95%, or 99% identity to the amino acid sequence of SEQ ID NO:42 and a beta chain having at least 90%, 95%, or 99% identity to the amino acid sequence of SEQ ID NO:47.

7. The TCR of claim 1, wherein the TCR comprises:
(a) for claim 1 (a), an alpha chain of SEQ ID NO: 2 and a beta chain of SEQ ID NO: 7;
(b) for claim 1 (b), an alpha chain of SEQ ID NO: 12 and a beta chain of SEQ ID NO:17;
(c) for claim 1 (c), an alpha chain of SEQ ID NO:22 and a beta chain of SEQ ID NO:27;
(d) for claim 1 (d), an alpha chain of SEQ ID NO:32 and a beta chain of SEQ ID NO:37; or
(e) for claim 1 (e), an alpha chain of SEQ ID NO:42 and a beta chain of SEQ ID NO:47.

8. The TCR of claim 6, wherein the TCR comprises:
(a) for claim 6 (a), an alpha chain encoded by a nucleotide sequence having at least 95% identity to the nucleotide sequence of SEQ ID NO: 1 and a beta chain encoded by a nucleotide sequence having at least 95% identity to the nucleotide sequence of SEQ ID NO: 6;
(b) for claim 6 (b), an alpha chain encoded by a nucleotide sequence having at least 95% identity to the nucleotide sequence of SEQ ID NO:11 and a beta chain encoded by a nucleotide sequence having at least 95% identity to the nucleotide sequence of SEQ ID NO: 16;
(c) for claim 6 (c), an alpha chain encoded by a nucleotide sequence having at least 95% identity to the nucleotide sequence of SEQ ID NO:21 and a beta chain encoded by a nucleotide sequence having at least 95% identity to the nucleotide sequence of SEQ ID NO: 26;
(d) for claim 6 (d), an alpha chain encoded by a nucleotide sequence having at least 95% identity to the nucleotide sequence of SEQ ID NO:31 and a beta chain encoded by a nucleotide sequence having at least 95% identity to the nucleotide sequence of SEQ ID NO: 36; or (e) for claim 6 (e), an alpha chain encoded by a nucleotide sequence having at least 95% identity to the nucleotide sequence of SEQ ID NO:41 and a beta chain encoded by a nucleotide sequence having at least 95% identity to the nucleotide sequence of SEQ ID NO: 46.

9. The TCR of claim 6, wherein the TCR comprises:
(a) for claim 6 (a), an alpha chain encoded by a nucleotide sequence comprising the nucleotide sequence of SEQ ID NO: 1 and a beta chain encoded by a nucleotide sequence comprising the nucleotide sequence of SEQ ID NO: 6;
(b) for claim 6 (b), an alpha chain encoded by a nucleotide sequence comprising the nucleotide sequence of SEQ ID NO:11 and a beta chain encoded by a nucleotide sequence comprising the nucleotide sequence of SEQ ID NO:16;
(c) for claim 6 (c), an alpha chain encoded by a nucleotide sequence comprising the nucleotide sequence of SEQ ID NO:21 and a beta chain encoded by a nucleotide sequence comprising the nucleotide sequence of SEQ ID NO:26;
(d) for claim 6 (d), an alpha chain encoded by a nucleotide sequence comprising the nucleotide sequence of SEQ ID NO:31 and a beta chain encoded by a nucleotide sequence comprising the nucleotide sequence of SEQ ID NO:36; or (e) for claim 6 (e), an alpha chain encoded by a nucleotide sequence comprising the nucleotide sequence of SEQ ID NO:41 and a beta chain encoded by a nucleotide sequence comprising the nucleotide sequence of SEQ ID NO:46.

10. The TCR of claim 1, wherein the TCR is further defined as a soluble TCR, wherein the soluble TCR does not comprise a transmembrane domain.

11. The TCR of claim 1, further comprising a detectable label.

12. The TCR of claim 1, wherein the TCR is covalently bound to a therapeutic agent.

13. A multivalent TCR complex comprising a plurality of TCRs according to claim 1.

14. The complex of claim 13, wherein the multivalent TCR comprises 2, 3, 4 or more TCRs associated with one another.

15. A method of treating cancer in a subject comprising administering an effective amount of a host cell engineered to express the TCR of claim 1 to the subject.

16. The method of claim 15, wherein the subject is identified to have an HLA-A*0201 allele or an HLA-A*2402 allele.

17. The method of claim 15, wherein the host cell is a TCR-engineered T cell or peripheral blood lymphocyte.

18. The method of claim 15, wherein the cancer is a melanoma.

19. The method of claim 15, further comprising lymphodepletion of the subject prior to administration of the cells.

20. The method of claim 15, wherein the subject is determined to have cancer cells which overexpress SLC45A2.

* * * * *